United States Patent
Dahl et al.

(10) Patent No.: US 8,039,214 B2
(45) Date of Patent: Oct. 18, 2011

(54) SYNTHESIS OF TAGGED NUCLEIC ACIDS

(75) Inventors: Gary Dahl, Madison, WI (US); Roy Rabindranauth Sooknanan, Beaconsfield (CA)

(73) Assignee: CellScript, Inc., Madison, WI (US)

( * ) Notice: Subject to any disclaimer, the term of this patent is extended or adjusted under 35 U.S.C. 154(b) by 445 days.

(21) Appl. No.: 12/165,324

(22) Filed: Jun. 30, 2008

(65) Prior Publication Data

US 2009/0053775 A1 Feb. 26, 2009

Related U.S. Application Data

(60) Provisional application No. 60/937,666, filed on Jun. 29, 2007.

(51) Int. Cl.
*C12Q 1/68* (2006.01)
*C12P 19/34* (2006.01)

(52) U.S. Cl. ............ 435/6.11; 435/6.12; 435/91.1; 435/91.2

(58) Field of Classification Search ............ 435/6, 91.1, 435/91.2
See application file for complete search history.

(56) References Cited

U.S. PATENT DOCUMENTS

| | | |
|---|---|---|
| 5,021,335 A | 6/1991 | Tecott |
| 5,130,238 A | 7/1992 | Malek |
| 5,168,038 A | 12/1992 | Tecott |
| 5,169,766 A | 12/1992 | Schuster |
| 5,194,370 A | 3/1993 | Berninger |
| 5,399,491 A | 3/1995 | Kacian |
| 5,409,818 A | 4/1995 | Davey |
| 5,437,990 A | 8/1995 | Burg |
| 5,466,586 A | 11/1995 | Davey |
| 5,514,545 A | 5/1996 | Eberwine |
| 5,545,522 A | 8/1996 | Van Gelder |
| 5,554,517 A | 9/1996 | Davey |
| 5,665,545 A | 9/1997 | Malek |
| 5,679,512 A | 10/1997 | Laney |

(Continued)

FOREIGN PATENT DOCUMENTS

EP 0427073 5/1991

(Continued)

OTHER PUBLICATIONS

Butler and Chamberlain, "Bacteriophage SP6-specific RNA polymerase. I. Isolation and characterization of the enzyme" 1982 J. Biol. Chem. 257:5772-5778.

(Continued)

*Primary Examiner* — Kenneth R. Horlick
(74) *Attorney, Agent, or Firm* — Casimir Jones, S.C.

(57) ABSTRACT

The present invention relates generally to methods, compositions and kits for synthesizing sense RNA molecules from one or more RNA molecules of interest in a sample. In exemplary embodiments, the methods use a terminal tagging oligoribonucleotide (rTTO) to join a DNA sequence tag to the 3'-termini of first-strand cDNA molecules. The use of an rTTO comprising ribonucleotides results in decreased oligonucleotide-derived background synthesis of RNA in the absence of sample RNA and, surprisingly and unexpectedly, also results in significantly increased yields of sense RNA molecules that exhibit sequences that are substantially identical to those of the RNA molecules of interest in the sample. The sense RNA molecules also have an RNA sequence tag on their 5'-termini that is useful for fixing the lengths of sense RNA molecules that are synthesized in a second or subsequent round.

14 Claims, 15 Drawing Sheets

U.S. PATENT DOCUMENTS

| | | | |
|---|---|---|---|
| 5,712,127 | A | 1/1998 | Malek |
| 5,716,785 | A | 2/1998 | Van Gelder |
| 5,849,546 | A | 12/1998 | Sousa |
| 5,891,636 | A | 4/1999 | Van Gelder |
| 5,958,688 | A | 9/1999 | Eberwine |
| 5,962,271 | A | 10/1999 | Chenchik |
| 5,962,272 | A | 10/1999 | Chenchik |
| 6,057,494 | A | 5/2000 | Koops et al. |
| 6,063,603 | A | 5/2000 | Davey |
| 6,090,591 | A | 7/2000 | Burg |
| 6,096,503 | A | 8/2000 | Sutcliffe et al. |
| 6,100,024 | A | 8/2000 | Hudson |
| 6,291,170 | B1 | 9/2001 | Van Gelder |
| 6,410,276 | B1 | 6/2002 | Burg |
| 6,528,262 | B1 | 3/2003 | Gilad et al. |
| 6,808,888 | B2 | 10/2004 | Zhang |
| 6,818,421 | B2 | 11/2004 | Kossman et al. |
| 7,335,471 | B2 | 2/2008 | Guillerez |
| 7,354,742 | B2 | 4/2008 | Kamme |
| 7,550,264 | B2 | 6/2009 | Getts |
| 2002/0127592 | A1 | 9/2002 | Ichihara |
| 2003/0186237 | A1 | 10/2003 | Ginsberg |
| 2004/0110191 | A1* | 6/2004 | Winkler et al. .............. 435/6 |
| 2004/0171041 | A1 | 9/2004 | Dahl |
| 2004/0197802 | A1 | 10/2004 | Dahl |
| 2005/0153333 | A1 | 7/2005 | Sooknanan |
| 2006/0035226 | A1 | 2/2006 | Scheinert |
| 2007/0048741 | A1 | 3/2007 | Getts |
| 2007/0105124 | A1 | 5/2007 | Getts |
| 2008/0020431 | A1 | 1/2008 | Getts |

FOREIGN PATENT DOCUMENTS

| | | |
|---|---|---|
| EP | 0427074 | 5/1991 |
| WO | 8906700 | 7/1989 |
| WO | 9118155 | 11/1991 |
| WO | 9942618 | 8/1999 |
| WO | 0075356 | 12/2000 |
| WO | 02065093 | 8/2002 |
| WO | 2007062495 | 7/2007 |

OTHER PUBLICATIONS

Dunn et al., "Different template specificities of phage T3 and T7 RNA polymerases" 1971 Nature New Biology 230:94-96.

Eberwine et al., "Analysis of gene expression in single live neurons" 1992 Proc. Natl. Acad. Sci. USA 89:3010-3014.

Edmonds et al., "Polyadenylate polymerases" 1990 Methods Enzymol., 181; 161-180.

Fahy et al., "Self-sustained sequence replication (3SR): an isothermal transcription-based amplification system alternative to PCR" 1991 PCR Methods and Applications, pp. 25-33.

Gershon et al., "(A)-tail of two polymerase structures" 2000 Nature Structural Biol. 7: 819-821.

Ginsberg et al., "Expression profile of transcripts in Alzheimer's disease tangle-bearing CA1 neurons" 2000 Ann. Neurol. 48:77-87.

Ginsberg et al., "Predominance of neuronal mRNAs in individual Alzheimer's disease senile plaques" 1999 Ann. Neurol. 45:174-181.

Harris et al., "An improved RNA amplification procedure results in increased yield of autologous RNA transfected dendritic cell-based vaccine" 2005 Biochimica Biophysica Acta—General Subjects 1724: 127-136.

Hausmann, "Bacteriophage T7 genetics" 1976 Current Topics in Microbiology and Immunology 75:77-109.

Kazmierczak et al., "The phage N4 virion RNA polymerase catalytic domain is related to single-subunit RNA polymerases" 2002 EMBO J., 21: 5815-5823.

Korsten et al., J. Gen. Virol. 43:57-73, 1975.

Kwoh et al., "Transcription-based amplification system and detection of amplified human immunodeficiency virus type 1 with a bead-based sandwich hybridization format" 1989 Proc. Natl. Acad. Sci. USA 86:1173.

Mueller et al., "CapSelect: a highly sensitive method for 5' CAP-dependent enrichment of full-length cDNA in PCR-mediated analysis of mRNAs" 1999 Nucleic Acids Res., 27: e31.

Murakawa et al., "Direct detection of HIV-1 RNA from AIDS and ARC patient samples" 1988 DNA 7:287-295.

Ohmichi et al. "Efficient bacterial transcription of DNA nanocircle vectors with optimized single-stranded promoters" 2002 Proc. Natl. Acad. Sci. USA 99:54-59.

Ozawa, T et al. "Amplification and analysis of cDNA generated from a single cell by 5'-RACE: application to isolation of antibody heavy and light chain variable gene sequences from single B cells" 2006 Biotechniques 40: 469-478.

Padilla and Sousa, "A Y639F/H784A T7 RNA polymerase double mutant displays superior properties for synthesizing RNAs with non-canonical NTPs" 2002 Nucleic Acids Res., 15: e138.

Phillips and Eberwine, "Antisense RNA Amplification: A Linear Amplification Method for Analyzing the mRNA Population from Single Living Cells" 1996 Methods in Enzymol. Suppl. 10:283-288.

Sousa and Mukherjee, "T7 RNA polymerase" 2003 Prog Nucleic Acid Res Mol Biol., 73: 1-41.

Studier, FW et al., "Use of T7 RNA polymerase to direct expression of cloned genes" pp. 60-89 in Methods in Enzymology, vol. 185, ed. by Goeddel, DV, Academic Press, 1990.

Towle, et al., "Purification and characterization of bacteriophage gh-I-induced deoxyribonucleic acid-dependent ribonucleic acid polymerase from *Pseudomonas putida*" 1975 J. Biol. Chem. 250:1723-1733.

Vangelder et al., Proc. Natl. Acad. Sci. USA 87:1663-1667, 1990.

Wilusz and Shenk, Cell 52: 221, 1988.

International Search Report mailed Jan. 7, 2009 for PCT/US2008/068844.

* cited by examiner

Joining the DNA sequence tag to the 3'-termini of first-strand cDNA molecules using a terminal tagging oligoribonucleotide (rTTO)

Synthesis of double-stranded cDNA molecules that have an RNA polymerase promoter Synthesis of sense RNA molecules that have an RNA sequence tag joined to their 5'-termini by transcription of double-stranded cDNA molecules that have an RNA polymerase promoter Second-round synthesis of first-strand cDNA molecules that have a DNA sequence tag on their 3'-termini and double-stranded cDNA molecules that have an RNA polymerase promoter

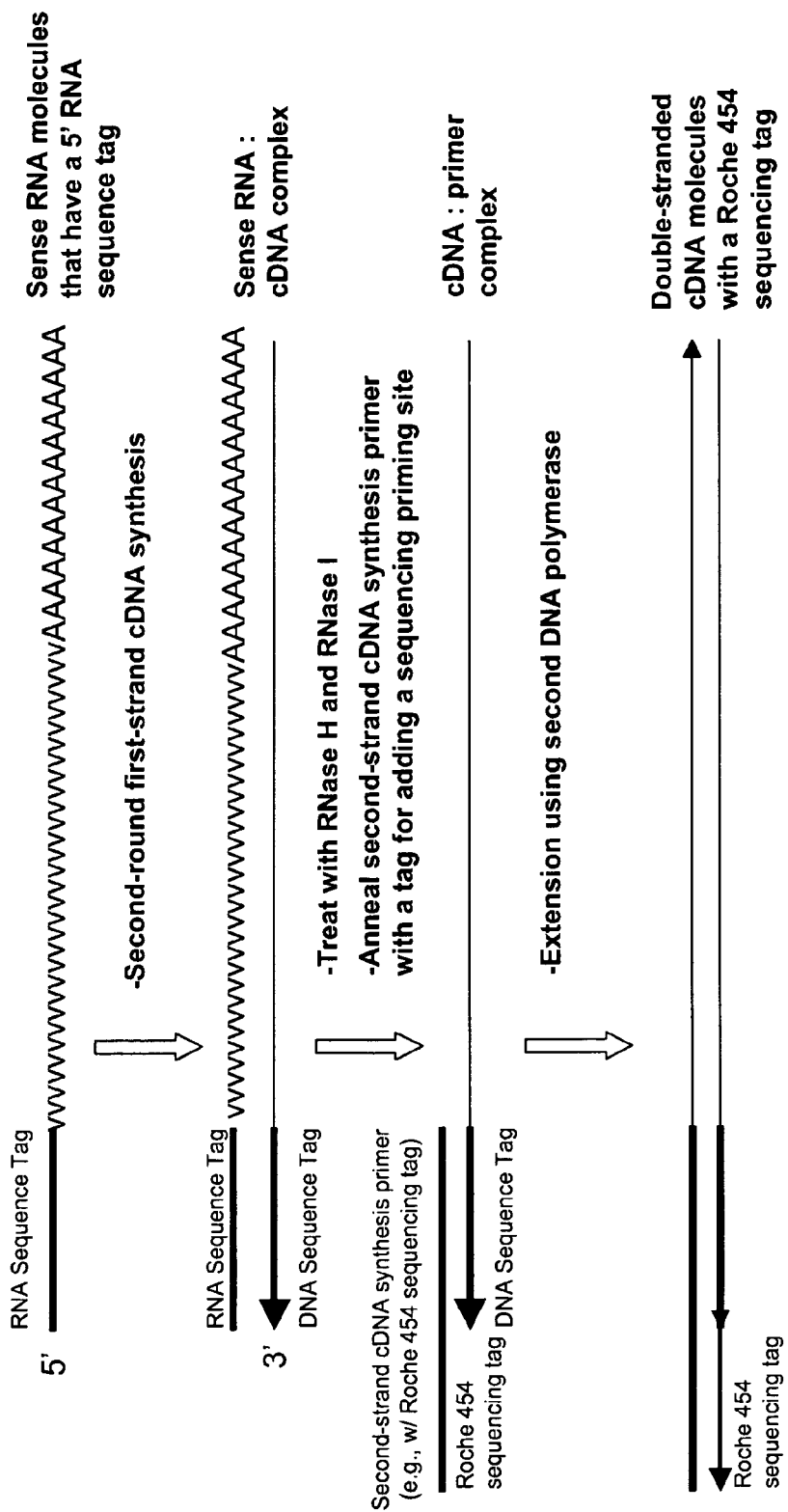

FIG. 7

Amplified RNA produced using an oligo(dT)$_n$ first-strand cDNA synthesis primer and a deoxy Terminal Tagging Oligonucleotide (dTTO) with and without purification steps prior to first-round IVT

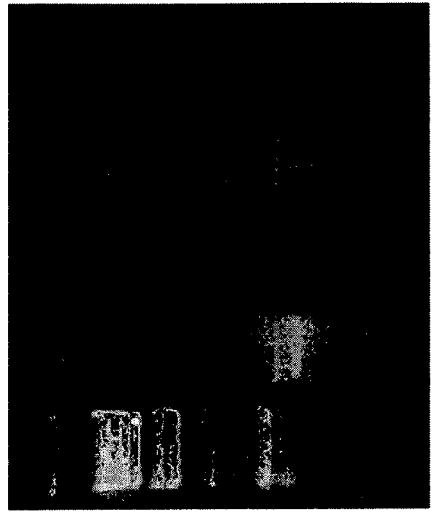

low molecular weight products

1 – 10 μL of 1-round amplified RNA from the 100 ng HeLa RNA template reaction with two purification steps prior to IVT
2 – 10 μL of 1-round amplified RNA from the no template reaction with two purification steps prior to IVT
3 – 10 μL of 1-round amplified RNA from the 100 ng HeLa RNA template reaction with no purification step prior to IVT
4 – 10 μL of 1-round amplified RNA from the no template reaction with no purification step prior to IVT
M – dsDNA molecular weight marker

FIG. 8

Amplified RNA produced after 2-rounds using an oligo(dT)$_n$ first-strand cDNA synthesis primer and a deoxy Terminal Tagging Oligonucleotide (dTTO) for first-round RNA with purification steps prior to IVT

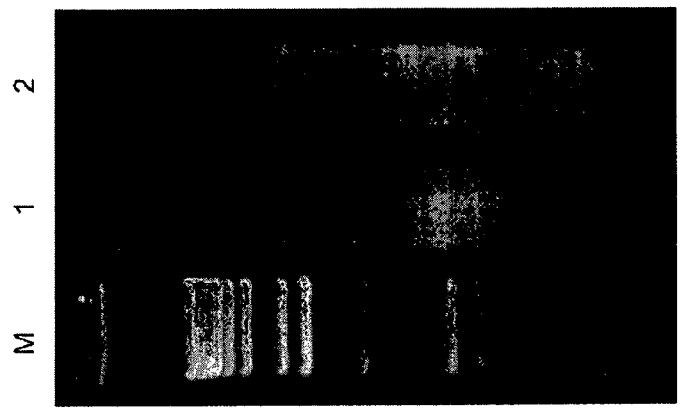

1 – 300 ng of second-round amplified RNA from the first-round template reaction with two purification steps prior to IVT
2 – 300 ng of second-round amplified RNA from the first-round no template reaction with two purification steps prior to IVT
M – dsDNA molecular weight marker

FIG. 9

Amplified RNA produced after 2-rounds using an oligo(dT)n first-strand cDNA synthesis primer and a ribo Terminal Tagging Oligonucleotide (rTTO) for first-round RNA with either 1 or 2 purification steps prior to IVT

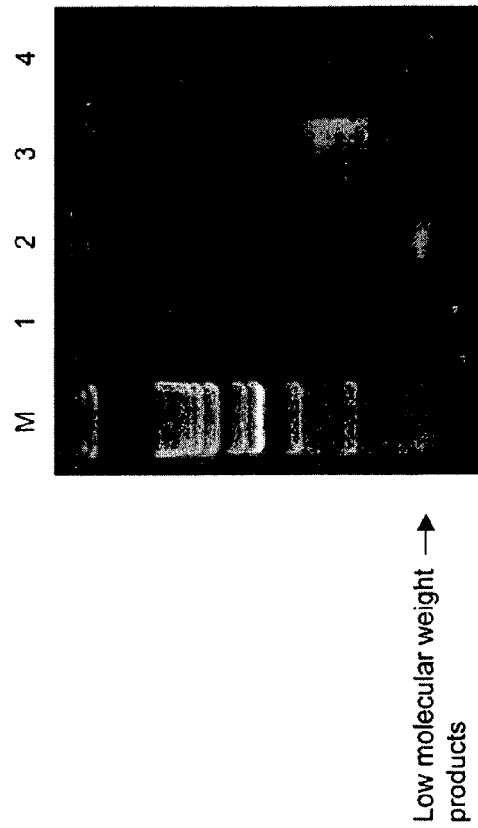

Low molecular weight products

1 – 300 ng of 2-round amplified RNA from the 5 ng HeLa RNA template reaction with one purification step prior to IVT in the first-round 2 – 300 ng of 2-round amplified RNA from the no template reaction with one purification step prior to IVT in the first-round 3 – 300 ng of 2-round amplified RNA from the 5 ng HeLa RNA template reaction with two purification steps prior to IVT in the first-round 4 – 300 ng of 2-round amplified RNA from the no template reaction with two purification step prior to IVT in the first-round M – dsDNA molecular weight marker

FIG. 10

Comparing different combinations of ribo [oligo(U)$_n$ and rTTO] and deoxy [oligo(dT)$_n$ and dTTO] First-strand cDNA Synthesis Primers and Terminal Tagging Oligonucleotides to eliminate or reduce non-specific background in the absence of purification steps prior to first-round IVT

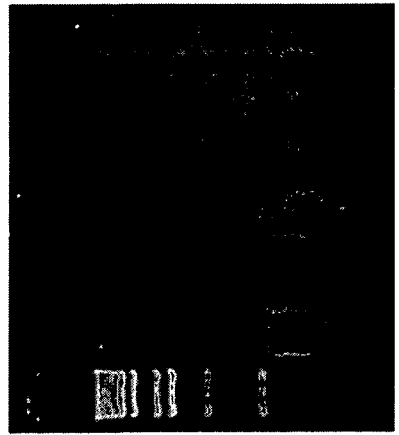

A.

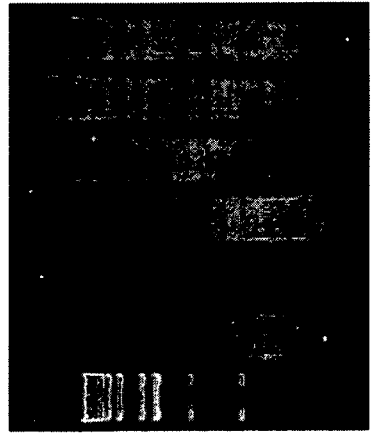

B.

1 – Amplified RNA produced using oligo(U)n/rTTO with 100 ng total RNA input
2 – Amplified RNA produced using oligo(U)n/rTTO with no total RNA input
3 – Amplified RNA produced using oligo(dT)n/rTTO with 100 ng total RNA input
4 – Amplified RNA produced using oligo(dT)n/rTTO with no total RNA input
5 – Amplified RNA produced using oligo(dT)n/dTTO with 100 ng total RNA input
6 – Amplified RNA produced using oligo(dT)n/dTTO with no total RNA input A – 250 pmoles rTTO or dTTO per reaction
B – 750 pmoles rTTO or dTTO per reaction
M – dsDNA molecular weight marker Synthesis of double-stranded cDNA, and then labeled sense RNA target for gene expression analysis on microarray chips spotted with anti-sense probes

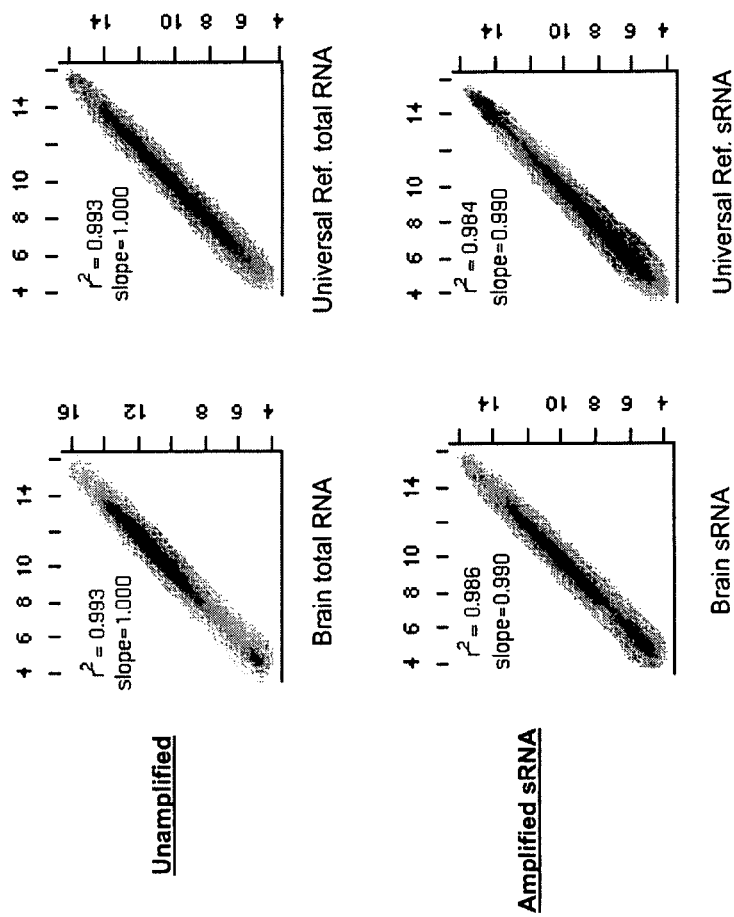

Correlation between log2 expression ratios for amplified sense RNA and unamplified total RNA Correlation of log2 expression ratios for amplified sense RNA and unamplified total RNA with MAQC TaqMan assays (~1000 Genes)

Full-length RT-PCR amplification results obtained comparing first- and second-round amplified 5'-tagged sense RNA

```
                        SEQUENCE LISTING

<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
tttttttttt tttttttttt v                                                 21

<210> SEQ ID NO 2
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(24)
<223> OTHER INFORMATION: n is a, c, g, or t

<400> SEQUENCE: 2
gacgaagaca gtagacannn nnnn                                              24

<210> SEQ ID NO 3
<211> LENGTH: 43
<212> TYPE: DNA
<213> ORGANISM: Artificial Sequence
<220> FEATURE:
<223> OTHER INFORMATION: Synthetic

<400> SEQUENCE: 3
aattctaata cgactcacta tagggagacg aagacagtag aca                         43

<210> SEQ ID NO 4
<211> LENGTH: 23
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(23)
<223> OTHER INFORMATION: n is a, c, g, or u

<400> SEQUENCE: 4
gacgaagaca guagacannn nnn                                               23
```

```
<210> SEQ ID NO 5
<211> LENGTH: 21
<212> TYPE: RNA
<213> ORGANISM: Artificial Sequence
<220> FEATURE:
<223> OTHER INFORMATION: Synthetic

<400> SEQUENCE: 5
uuuuuuuuuu uuuuuuuuuu v                                              21

<210> SEQ ID NO 6
<211> LENGTH: 18
<212> TYPE: DNA
<213> ORGANISM: Artificial Sequence
<220> FEATURE:
<223> OTHER INFORMATION: Synthetic

<400> SEQUENCE: 6
taatacgact cactatag                                                  18

<210> SEQ ID NO 7
<211> LENGTH: 18
<212> TYPE: DNA
<213> ORGANISM: Artificial Sequence
<220> FEATURE:
<223> OTHER INFORMATION: Synthetic

<400> SEQUENCE: 7
ctatagtgag tcgtatta                                                  18
```

SYNTHESIS OF TAGGED NUCLEIC ACIDS

CROSS-REFERENCE TO RELATED APPLICATION

This application claims priority to U.S. Provisional patent application 60/937,666, filed Jun. 29, 2007, the disclosure of which is herein incorporated by reference in its entirety.

FIELD OF THE INVENTION

The present invention relates generally to methods, compositions and kits for synthesizing first-strand cDNA, double-stranded cDNA and multiple copies of sense RNA from one or more RNA molecules of interest in a sample.

BACKGROUND OF THE INVENTION

A number of methods are known in the art that use an oligonucleotide that exhibits a proto-promoter sequence to synthesize first-strand cDNA and then double-stranded cDNA that contains an RNA polymerase promoter (e.g., in order to amplify RNA molecules in a sample for gene expression analysis and other purposes). A "proto-promoter sequence" is a single-stranded DNA or RNA sequence region which, in double-stranded DNA form, is capable of mediating RNA transcription by serving as an RNA polymerase promoter.

One of the most common methods for evaluating the expression of mRNA transcripts in a small biological sample comprises: synthesizing first-strand cDNA using an oligo (dT) promoter primer; synthesizing second-strand cDNA using the fragments of the mRNA or a first-strand cDNA hairpin as a primer and the first-strand cDNA as a template; and transcribing the double-stranded cDNA containing an RNA polymerase promoter using RNA polymerase, as described by Van Gelder et al. in U.S. Pat. Nos. 5,545,522; 5,716,785; and 5,891,636. Thus, the second-strand cDNA is the template strand and the RNA synthesized is complementary to (or "anti-sense" to) the mRNA in the sample. The single-stranded promoter sequence exhibited by the promoter primer of Van Gelder et al., which is one strand of a functional double-stranded promoter, is referred to herein as an "anti-sense promoter sequence" and the corresponding promoter primer is referred to herein as an "anti-sense promoter primer." Similarly, the promoter sequence of a double-stranded promoter that is operably joined to the template strand is referred to herein as a "sense promoter sequence." For example, but without limiting the invention with respect to the promoter sequence or the respective RNA polymerase used for transcription, whereas one T7 RNA polymerase anti-sense promoter sequence and +1 base exhibited by a promoter primer in U.S. Pat. Nos. 5,545,522; 5,716,785; and 5,891,636 is:

```
(5' TAATACGACTCACTATAG, 3        SEQ ID NO: 6');
``` the corresponding T7 RNA polymerase sense promoter sequence and +1 base is:

```
(5' CTATAGTGAGTCGTATTA, 3'       SEQ ID NO: 7).
```

A number of methods are known in the art for using RNA in a sample as a template and an oligonucleotide with a proto-promoter sequence to synthesize double-stranded cDNA and then labeled anti-sense RNA ("aRNA") (e.g., for gene expression profiling and other applications), including, for example, methods described in: Murakawa et al., DNA 7:287-295, 1988; Phillips and Eberwine, Methods in Enzymol. Suppl. 10:283-288, 1996; Ginsberg et al., Ann. Neurol. 45:174-181, 1999; Ginsberg et al., Ann. Neurol. 48:77-87, 2000; VanGelder et al., Proc. Natl. Acad. Sci. USA 87:1663-1667, 1990; Eberwine et al., Proc. Natl. Acad. Sci. USA 89:3010-3014, 1992; U.S. Pat. Nos. 5,021,335; 5,130,238; 5,168,038; 5,399,491; 5,437,990; 5,545,522; 5,514,545; 5,665,545; 5,716,785; 5,891,636; 5,958,688; 6,291,170; PCT Patent Applications WO 00/75356 and WO 02/065093; and U.S. Patent Application Nos. 20020127592; Kamme: 20030175714; and Scheinert: 20060035226.

Other methods use in vitro transcription as part of a process for amplifying and detecting one or more nucleic acid sequences, including, for example, methods described in U.S. Pat. Nos. 5,194,370; 5,409,818; 5,466,586; 5,554,517; 6,063,603; 6,090,591; 6,100,024; 6,410,276; Kwoh et al., Proc. Natl. Acad. Sci. USA 86:1173, 1989; Fahy et al, In: PCR Methods and Applications, pp. 25-33, 1991; PCT Patent Application Nos. WO 89/06700 and WO 91/18155; and European Patent Application Nos. 0427073 A2 and 0427074 A2.

Although much less used, methods for synthesizing sense RNA molecules corresponding to RNA in a sample are also known in the art. For example, in U.S. Pat. No. 5,169,766, Schuster and Berninger disclosed a method for using a proto-promoter-containing nucleic acid molecule having a blocked 3'-terminus to add DNA that exhibited a sense promoter sequence to the 3'-termini of first-strand cDNA molecules. In U.S. Pat. Nos. 5,962,271 and 5,962,272, Chenchik et al. disclosed a method for using a template switching oligonucleotide to add an arbitrary sequence to the 3'-termini of first-strand cDNA molecules, which method has been coupled to the use of a PCR primer that exhibits an anti-sense-promoter sequence in its 5'-portion and a sequence that is complementary to the arbitrary sequence in its 3'-terminal portion to make double-stranded cDNA that is transcribed with an RNA polymerase to make multiple copies of sense RNA (Harris, J et al., Biochimica Biophysica Acta—General Subjects 1724: 127-136, 2005). In U.S. Patent Application No. 20030073112, Zhang et al. disclose use of a second-strand cDNA synthesis primer that is promoter primer with a random 3'-terminal sequence for synthesis of cDNA that can be transcribed. In U.S. Patent Application No. 20030186237 and PCT Patent Application No. WO 02/065093, Ginsberg al. disclosed a method to make sense RNA molecules by first using a method similar to Chenchik et al. to add a sequence tag, and then to generate double-stranded cDNA with an RNA polymerase promoter. In U.S. Patent Application No. 20040171041, Dahl et al. disclosed methods for joining DNA that exhibits a sense promoter sequence for an RNA polymerase promoter to the 3'-termini of first-strand cDNA molecules. In U.S. Patent Application No. 20050153333 and PCT Patent Application No. WO 2007062495, Sooknanan disclosed methods for selective terminal tagging of nucleic acids, which can be used for joining an RNA polymerase promoter for synthesis of sense RNA molecules. In U.S. Patent Application Nos. 20060281153; 20070048741; 20070105124; and 20080020431, Getts et al. disclosed methods to synthesize sense RNA after making cDNA molecules with an RNA polymerase promoter using terminal transferase and a single-stranded promoter template.

Although several methods have been disclosed for amplifying sense RNA molecules that correspond to RNA in a sample, none of these methods is widely used in the art. This is unfortunate because methods that synthesize multiple copies of sense RNA molecules corresponding to RNA molecules of interest in a sample provide several advantages over methods that synthesize anti-sense RNA molecules. For example, since the sense RNA molecules synthesized using some of these methods have an RNA sequence tag joined to their 5'-termini, they can be used for subsequent rounds of synthesis of more first-strand cDNA molecules that have a DNA sequence tag joined to their 3'-termini and more sense RNA molecules that have the RNA sequence tag joined to their 5'-termini. The RNA sequence tag thereby fixes the length of the cDNA product and of the sense RNA product synthesized in the subsequent rounds. Thus, although the methods that use an anti-sense promoter primer (e.g., the methods described in U.S. Pat. Nos. 5,545,522; 5,716,785; and 5,891,636) result in anti-sense RNA products that have a 3'-bias (i.e., the anti-sense RNA molecules synthesized using the method exhibit sequences derived from the 3'-portions of the RNA molecules of interest to a greater extent than they exhibit sequences derived from the 5'-portions of the RNA molecules of interest), and which, moreover, become shorter and more 3'-biased during each round of amplification, the methods that synthesize sense RNA have less 3'-bias and, due to the presence of the DNA and RNA sequence tags, the lengths of the products are generally maintained during each round of amplification. Sense RNA molecules are also advantageous over anti-sense RNA molecules because they exhibit substantially the same sequences as the RNA molecules of interest in the sample. Thus, for example, sense RNA molecules synthesized using mRNA molecules of interest can be used for in vitro or in vivo translation of proteins that exhibit substantially the same amino acid sequences as those which are present in the sample.

One reason the methods for synthesis of sense RNA are not widely used in the art in spite of their advantages is that they generally result in synthesis of significant quantities of non-specific background RNA that is not related to the RNA molecules of interest in the sample. In general, excess primers and primer-induced artifacts (e.g., primers which are tagged with a sequence tag and with an RNA polymerase promoter) are key sources of the non-specific background. Thus, the methods in the art typically require time-consuming and tedious steps, such as use of mini-columns, in order to try to remove the sources of the background. Often, significant background remains even after these purification steps because not all of the nucleic acid molecules that contribute to the background are removed. At the same time, the purification steps can result in significant losses of nucleic acid molecules that are derived from the RNA molecules of interest, which can potentially decrease the sensitivity, or even affect the interpretation of the results obtained.

What is needed in the art are methods for synthesis of first-strand cDNA molecules, double-stranded cDNA molecules, and sense RNA molecules that provide the benefits of using the respective sequence tags (e.g., less 3'-sequence bias and fixed product lengths during multiple rounds of synthesis), but which do not result in synthesis of significant quantities of non-specific background RNA that is not related to the RNA molecules of interest in the sample. What is needed are methods for synthesizing first-strand cDNA molecules, double-stranded cDNA molecules, and sense RNA molecules wherein tedious and time-consuming mini-column or other purification steps, particularly purification steps that result in losses of nucleic acid molecules derived from the RNA molecules of interest, are minimized or avoided. What is needed are methods that are more efficient for obtaining first-strand cDNA molecules that have a DNA sequence tag joined to their 3'-termini and sense RNA molecules that have an RNA sequence tag joined to their 5'-termini. What is needed are methods to obtain such amplified sense RNA molecules that exhibit substantially the same sequences and that are present in substantially the same abundances as the RNA molecules of interest in the sample, including mRNA or miRNA or ncRNA molecules of interest from small biological samples, for applications such as expression analysis, and for preparing sense RNA molecules for transfection into a eukaryotic or prokaryotic cell to study or cause a biological effect, for in vivo translation into protein in prokaryotic or eukaryotic cells, or for in vitro translation in a cell-free system. What is needed are methods that enable generation of complete libraries of cDNA molecules and complete libraries of sense RNA molecules, which represent all of the RNA molecules of interest in a sample, including even a sample consisting of approximately 1000 to 10,000, 100 to 1000, 10 to 100, or even 1 to 10 cells.

SUMMARY OF THE INVENTION

A primary aim of the work that led to embodiments of the present invention was to find methods to reduce primer- and oligonucleotide-related background amplification that occurs in the absence of sample RNA using the terminal tagging method of Sooknanan (U.S. Patent Application No. 2005015333; PCT Patent Application No. WO 2007062495). This method is useful for synthesizing 3'-tagged first-strand cDNA, double-stranded cDNA that contains an RNA polymerase promoter, and 5'-tagged sense RNA molecules (also called "sense RNA molecules that have the RNA sequence tag on their 5'-termini" herein) from RNA molecules of interest from small biological samples.

In that earlier work, Sooknanan demonstrated, for example, (e.g., see EXAMPLE 1 of U.S. Patent Application No. 2005015333; PCT Patent Application No. WO 2007062495) that amplified 5'-tagged sense RNA could be obtained by: first, isolating total RNA from cells, then synthesizing first-strand cDNA by reverse transcription of the mRNA in the total RNA using a reverse transcriptase and an oligo $(dT)_{20}V$ first-strand cDNA synthesis primer; then using RNase A and RNase H to digest the RNA; then purifying the first-strand cDNA using a Qiagen mini-column; then adding a terminal sequence tag to the 3'-end of the first-strand cDNA using exo-minus Klenow DNA polymerase and a oligonucleotide sequence tag template; then extracting with phenol; then purifying the 3'-tagged first-strand cDNA by size selection using an Amersham mini-column; then priming synthesis of double-stranded cDNA that contained a T7 RNA polymerase promoter using a second oligonucleotide DNA primer and Advantage™ 2 DNA polymerase to extend the 3'-ends of both the 3'-tagged first-strand cDNA and the second oligonucleotide DNA primer; then purifying the double-stranded cDNA that contained a T7 RNA polymerase promoter by size selection using an Amersham mini-column; then synthesizing RNA by in vitro transcription of the double-stranded cDNA that contained a T7 RNA polymerase promoter using T7 RNA polymerase; then extracting with phenol; and then purifying the 5'-tagged RNA.

To overcome problems associated with the above processes, experiments conducted during the development of embodiments of the present invention identified compositions and methods to reduce the number of mini-column and other purification steps and the number of reagents used by using a terminal tagging oligonucleotide comprising ribonucleotides ("terminal tagging oligoribonucleotide" or "rTTO") instead of the equivalent DNA "oligonucleotide sequence tag template" used by Sooknanan. It was discovered that, after using the rTTO as a template to join a DNA sequence tag to the 3'-ends of the first-strand cDNA molecules, the rTTO could be easily and effectively removed by digesting with RNase H and a single-strand-specific RNase or with alkali, without further column or other purification prior to the next step, and that this, not only was easier and faster, but provided an unexpected and surprising increase the yields of the 5'-tagged sense RNA. It was also discovered that such methods produced little to no background. The unexpected high yield and low background observed with these methods establishes new and useful techniques for generating first-strand cDNA, double-stranded cDNA and multiple copies of sense RNA for a variety of applications.

In some embodiments, first-strand cDNA synthesis primers composed of ribonucleotides rather than deoxyribonucleotides are employed. Such embodiments decrease the number of purification steps, thereby making the method faster, easier and better in terms of yield, because such RNA first-strand cDNA synthesis primers can be degraded in the same step in which the RNA in the sample is degraded following synthesis of first-strand cDNA (e.g., by digesting them with RNase H and a single-strand-specific RNase or with alkali). Still further, when the RNA first-strand cDNA synthesis primers are completely digested, background synthesis of 5'-tagged sense RNA that could occur due to undesired tagging of DNA first-strand cDNA synthesis primers is avoided.

As described below, experiments demonstrated that the RNA first-strand cDNA synthesis primers and terminal tagging oligoribonucleotides, used according to the methods disclosed herein, reduced synthesis of background RNA in reactions to which no sample RNA was added to an undetectable level.

In conducting experiments during the development of the present invention, it was hoped that the yields of 5'-tagged sense RNA molecules would be increased somewhat. However, surprisingly and unexpectedly, the yields using the methods of the present invention were increased much more than expected.

Prior to the work described below, the applicants believed that the yields of 5'-tagged sense RNA molecules would be increased somewhat. However, surprisingly and unexpectedly, the yields using the methods of the present invention were increased much more than expected. In fact, the yields of 5'-tagged sense RNA using methods described herein were approximately as high after only one round of amplification as they had previously been after two rounds of amplification using the methods previously described by Sooknanan. For example, as described in Example 6 and shown in Table 2 of U.S. Patent Application No. 20050153333, Sooknanan obtained 5.9 micrograms of amplified 5'-tagged sense RNA from about 140 nanograms of total RNA from mouse osteoclast cells after two rounds of amplification. By comparison, as described in Example 4 and shown in Table 1 herein, about 58 micrograms of amplified 5'-tagged sense RNA was obtained from 100 nanograms of total RNA from HeLa human cells after only one round of amplification using r(U)$_{20}$V as the first-strand cDNA synthesis primer and a terminal tagging oligoribonucleotide (rTTO) in the method of the present invention. No background RNA was detectable after one round of amplification using the r(U)$_{20}$V first-strand cDNA synthesis primer and the rTTO in the absence of a HeLa cell input RNA. Also as shown in Table 1 herein, when the same amounts of a dT$_{20}$V first-strand cDNA synthesis primer and of the equivalent-sequence terminal tagging oligodeoxyribonucleotide (dTTO) were used in the method of the present invention, only about one microgram of amplified 5'-tagged sense RNA was obtained from 100 nanograms of total RNA from the HeLa cells after one round of amplification, and nearly the same amount of background RNA was synthesized even in the absence of input HeLa RNA. Thus, the methods disclosed herein, by substantially increasing the yields, have also substantially increased the sensitivity and range of detection and analysis of RNA molecules of interest in a sample, and have enabled synthesis of 5'-tagged sense RNA molecules from samples comprising only a small number of cells, as shown in Table 4. Since more amplified 5'-tagged sense RNA can be obtained in one round of amplification than in two rounds using the previous methods, time and work have been decreased by greater than two-fold, and throughput is substantially increased.

Thus, in some embodiments, the present invention provides methods for synthesizing first-strand cDNA, double-stranded cDNA and multiple copies of 5'-tagged sense RNA molecules from one or more RNA molecules of interest in a sample, including a sample consisting of approximately 1000 to 10,000, 100 to 1000, 10 to 100, or even 1 to 10 cells, wherein the methods do not synthesize substantial amounts of background nucleic acids that are derived from the primers or oligonucleotides used in the methods.

The methods also have greatly reduced the need to purify the products of each step of the synthesis of tagged first-strand cDNA, double-stranded cDNA, and sense RNA molecules using mini-columns or other purification methods, thus increasing yields by decreasing losses of respective product nucleic acids derived from the RNA molecules of interest in the sample.

The methods are also simpler and require less hands-on time than the methods presently in the art. Synthesis of one round of amplified 5'-tagged sense RNA molecules from one or more RNA molecules of interest in a sample is easily completed within one day, and multiple samples can be amplified simultaneously.

Another advantage of the methods of the present invention is that the first-strand cDNA molecules that have the DNA sequence tag joined to their 3'-termini, after being converted to double-stranded cDNA molecules that have an RNA polymerase promoter, serve as templates for synthesis of sense RNA molecules that have an RNA sequence tag joined to their 5'-termini, thereby providing a way to fix or maintain the length of the respective nucleic acid molecules synthesized during multiple rounds of synthesis of tagged first-strand cDNA, double-stranded cDNA and sense RNA molecules. Thus, when a method of the invention involves two or more rounds of synthesis, there is less bias for first-strand cDNA, double-stranded cDNA and sense RNA molecule products that exhibit sequences corresponding to predominantly the 3' portions of the RNA molecules of interest than would be obtained from the same number of rounds of synthesis using the methods described in the art (e.g., using the methods in U.S. Pat. Nos. 5,545,522; 5,716,785; and 5,891,636). Sense RNA molecules that have the RNA sequence tag joined to their 5'-termini obtained using the methods of the invention can be used for a variety of applications. For example, they can be used to prepare sense RNA molecules (e.g., that are capped and polyadenylated) for in vitro or in vivo translation into protein. In some embodiments, the 5'-tagged sense RNA molecules are used for gene expression analysis by RT-PCR. In some embodiments, the 5'-tagged sense RNA molecules synthesized using the method are used to prepare labeled 5'-tagged sense RNA molecules or labeled single-stranded or double-stranded cDNA molecules for use as target RNA or target DNA for microarray analysis (e.g., FIG. 11). For example, after using the methods comprising steps (A) through (F), described below, of the present invention to synthesize 5'-tagged sense RNA molecules from samples consisting of, respectively, human total reference RNA (AGILENT/Stratagene, CA, USA), and human brain reference RNA (Applied Biosystems/Ambion); followed by conversion of the 5'-tagged sense RNA molecules to labeled double-stranded DNA using a reverse transcriptase, and then performing relative gene expression analysis using NimbleGen Systems' (Roche/NimbleGen, Madison, Wis., USA) microarray chips, the correlation coefficient of the microarray results for relative expression versus the TaqMan real-time qPCR results for approximately one thousand genes in the MAQC Consortium database was 0.92 (r=0.92), which was equal to the highest correlation values published by the MAQC Consortium. These results show that the relative amounts of the amplified 5'-tagged sense molecules correlates very well with the relative amounts of the RNA molecules of interest in the samples from which they were derived. Thus, in some embodiments, the present invention provides methods that permit greater than 0.85 (e.g., greater than 0.90) correlation with values published by the MAQC Consortium. Such values may be calculated using the experimental parameters (e.g., amplification amounts, concentrations of reagents) described herein.

The methods also can be used to prepare first-strand cDNA molecules that have a DNA sequence tag on their 3'-termini and tagged double-stranded cDNA for use as templates for DNA sequencing or other analysis. For example, tagged first-strand and second-strand cDNA molecules made using the method can be used to prepare templates for next generation (NexGen) sequencing using NexGen DNA sequencers from companies such as 454/Roche (e.g., FIG. 10), Solexa/Illumina, Applied Biosystems, and Helicos. For example, tagged first-strand cDNA or double-stranded cDNA molecules can be prepared for use as NexGen sequencing templates by using one or more rounds of the methods of the invention to make amplified sense RNA molecules that have an RNA sequence tag on their 5'-termini from RNA molecules of interest in a sample containing RNA molecules (e.g., mRNA from a small number of eukaryotic or prokaryotic cells), and then converting the tagged sense RNA molecules to tagged cDNA sequencing templates. Thus, the methods permit sequencing of RNA molecules obtained from small samples, including samples comprising less than or equal to approximately ten thousand, one thousand, one hundred, or even one to ten cells.

Thus, the present invention provides methods that solve many of the problems related to the methods in the art for synthesizing nucleic acid molecules (e.g., first-strand cDNA, double-stranded cDNA and sense RNA molecules) from one or more RNA molecules of interest in a sample. Additional aspects of the invention will be understood from the specification below.

One preferred embodiment of the invention is a method for synthesizing multiple copies of sense RNA molecules that exhibit substantially the same sequences as the RNA molecules of interest in a sample, each of which sense RNA molecules has an RNA sequence tag that exhibits a desired arbitrary sequence joined to its 5'-terminus, the method comprising the steps (e.g., see FIG. 1 through FIG. 4) of:
(A) providing:
a sample containing one or more RNA molecules of interest;
at least one RNA-dependent DNA polymerase (e.g., AMV reverse transcriptase, or MMLV reverse transcriptase, or a mixture thereof);
a terminal tagging oligoribonucleotide comprising ribonucleotides (rTTO), which terminal tagging oligoribonucleotide comprises or consists of a 5'-portion and a 3'-portion, wherein the 5'-portion exhibits a sequence that is complementary to the sequence of the DNA sequence tag that it is desired to join to the 3'-termini of first-strand cDNA molecules, and wherein the 3'-portion comprises or consists of at least three random nucleotides (e.g., 3 to 8 random nucleotides; e.g., 7 random nucleotides), of which the 3'-terminal nucleotide is blocked so that it is not capable of being extended by a DNA polymerase;
a second-strand cDNA synthesis primer, comprising or consisting of an oligodeoxyribonucleotide that comprises or consists of a 5'-portion and a 3'-portion, wherein the 5'-portion exhibits at least a portion of an anti-sense promoter sequence for a double-stranded RNA polymerase promoter, and the 3'-portion has a 3'-hydroxyl group and exhibits a sequence that is complementary to the DNA sequence tag that it is desired to be joined to the 3'-termini of the first-strand cDNA molecules;
optionally, a DNA-template-specific DNA polymerase (e.g., MMLV reverse transcriptase, AMV reverse transcriptase or FailSafe™ DNA polymerase); and
an RNA polymerase (e.g., a T7-type RNA polymerase; e.g., T7, T3 or SP6 RNA polymerase) that is capable of synthesizing RNA using a DNA template that is joined to a double-stranded RNA polymerase promoter, wherein the 3'-terminus of the template strand exhibits a sequence that is complementary to the anti-sense promoter sequence exhibited by the 5'-portion of the second-strand cDNA synthesis primer;

(B) incubating a solution containing the sample with the one or more RNA molecules of interest, plus at least one of the at least one RNA-dependent DNA polymerases, under conditions and for sufficient time wherein first-strand cDNA molecules that are complementary to the RNA molecules of interest are synthesized;

(C) incubating the solution from step (B) under conditions and for sufficient time wherein RNA that is annealed to DNA and single-stranded RNA are degraded (e.g., in the presence of RNase H and a single-strand-specific RNase (e.g., RNase I), after which the RNase H and the single-strand-specific RNase are inactivated (e.g., by heating to 95 degrees centigrade for 3 to 10 minutes);

(D) incubating the solution from step (C) containing the first-strand cDNA molecules, plus the terminal tagging oligoribonucleotide and at least one of the at least one RNA-dependent DNA polymerases, under conditions and for sufficient time wherein the terminal tagging oligoribonucleotide anneals to the first-strand cDNA molecules and the 3'-termini of the first-strand cDNA molecules are extended using the terminal tagging oligoribonucleotide as a template, wherein first-strand cDNA molecules that have the DNA sequence tag joined to their 3'-termini are synthesized, and then incubating the solution under conditions and for sufficient time wherein RNA that is annealed to DNA and single-stranded RNA are degraded (e.g., in the presence of RNase H and a single-strand-specific RNase (e.g., RNase I), after which the RNase H and the single-strand-specific RNase are inactivated (e.g., by heating to 95 degrees centigrade for 3 to 10 minutes));

(E) incubating the solution from step (D) containing the first-strand cDNA molecules that have the DNA sequence tag joined to their 3'-termini, plus the second-strand cDNA synthesis primer and either at least one of the at least one RNA-dependent DNA polymerases or the DNA-template-specific DNA polymerase, under conditions and for sufficient time wherein double-stranded cDNA molecules that contain a double-stranded RNA polymerase promoter that is recognized by the RNA polymerase are synthesized;

(F) incubating the solution from step (E) containing double-stranded cDNA molecules, plus the RNA polymerase that recognizes and binds the double-stranded RNA polymerase promoter, under conditions and for sufficient time wherein multiple copies of sense RNA molecules are synthesized, each of which exhibits substantially the same sequence as one of the one or more RNA molecules of interest in the sample and has an RNA sequence tag joined to its 5'-terminus.

In some embodiments of any of the methods comprising steps (A) through (F), the sample containing the RNA molecules of interest that is provided in step (A) and used in step (B) comprises RNA that is substantially free of DNA.

In some preferred embodiments of the method comprising steps (A) through (F), the "at least one RNA-dependent DNA polymerase" provided in step (A) consists of only one RNA-dependent DNA polymerase, which RNA-dependent DNA polymerase is used in steps (B), and in step (D), and optionally, also in step (E). In some preferred embodiments, the RNA-dependent DNA polymerase used in both step (B) and in step (D), and optionally also in step (E), is AMV reverse transcriptase or RNase H-minus AMV reverse transcriptase.

In some other embodiments of the method comprising steps (A) through (F), the at least one RNA-dependent DNA polymerase provided in step (A) comprises or consists of two different RNA-dependent DNA polymerases, and the RNA-dependent DNA polymerase that is used in step (D) is different from the RNA-dependent DNA polymerase used in step (B), and, optionally, either one of the two RNA-dependent DNA polymerases or the DNA-template-specific DNA polymerase is used in step (E).

In some embodiments of any of the methods comprising all or a subset of steps (A) through (F), one or more first-strand cDNA synthesis primers comprising ribonucleotides (i.e., RNA first-strand cDNA synthesis primers), at least one of which is complementary to each of the RNA molecules of interest in the sample, is provided in step (A) and is used in step (B).

In some embodiments of any of the methods comprising all or a subset of steps (A) through (F), no first-strand cDNA synthesis primers are provided in step (A); and step (B) comprises: incubating the RNA molecules of interest in the solution with the RNA-dependent DNA polymerase, in the absence of added first-strand cDNA synthesis primers, under conditions and for sufficient time wherein first-strand cDNA molecules are synthesized.

In some embodiments of any of the methods comprising all or a subset of steps (A) through (F), one or more first-strand cDNA synthesis primers comprising deoxyribonucleotides, at least one of which is complementary to each of the RNA molecules of interest in the sample, is provided in step (A) and is used in step (B). In some embodiments wherein one or more first-strand cDNA synthesis primers comprising deoxyribonucleotides are used, following synthesis of first-strand cDNA molecules that are complementary to the RNA molecules of interest, step (C) additionally comprises the substep of: incubating the solution under conditions and for sufficient time wherein the one or more first-strand cDNA synthesis primers are degraded.

One preferred embodiment of the method comprising steps (A) through (F) further comprises an additional round of synthesizing multiple copies of sense RNA molecules, each of which exhibits substantially the same sequence as one of the one or more RNA molecules of interest in the sample and has the RNA sequence tag joined to its 5'-terminus, wherein the method further comprises the steps of:

(G) providing:
the sense RNA molecules that have the RNA sequence tag joined to their 5'-termini from step (F);
a second-round first-strand cDNA synthesis primers comprising or consisting of one or more oligonucleotides, at least one of which is complementary to each of the sense RNA molecules that have the RNA sequence tag joined to their 5'-termini that are provided in step (G) (e.g., in some embodiments, wherein the second-round first-strand cDNA synthesis primers are identical in sequence and composition to the first-strand cDNA synthesis primers provided in step (A));
at least one RNA-dependent DNA polymerase (e.g., AMV reverse transcriptase, or MMLV reverse transcriptase, or a mixture thereof);
a second-round second-strand cDNA synthesis primer, comprising or consisting of an oligodeoxyribonucleotide that has a 5'-portion and a 3'-portion, wherein the 5'-portion exhibits at least a portion of an anti-sense promoter sequence for a double-stranded RNA polymerase promoter, and the 3'-portion has a 3'-hydroxyl group and exhibits a sequence that is complementary to the DNA sequence tag that is joined to the 3'-termini of the first-strand cDNA molecules from step (D);
optionally, a DNA-template-specific DNA polymerase (e.g., MMLV reverse transcriptase, AMV reverse transcriptase or FailSafe™ DNA polymerase);
an RNA polymerase (e.g., a T7-type RNA polymerase; e.g., T7, T3 or SP6 RNA polymerase) that is capable of synthesizing RNA using a DNA template that is joined to a double-stranded RNA polymerase promoter that exhibits, on the 3'-terminus of the template strand, the sense promoter sequence of the double-stranded RNA polymerase promoter that, at least a portion of which, is complementary to the anti-sense promoter sequence exhibited by the 5'-portion of the second-round second-strand cDNA synthesis primer;

(H) incubating a solution containing the sense RNA molecules that have the RNA sequence tag joined to their 5'-termini, plus the second-round first-strand cDNA synthesis primers and at least one of the at least one RNA-dependent DNA polymerases, under conditions and for sufficient time wherein the second-round first-strand cDNA synthesis primers anneal to the sense RNA molecules that have the RNA sequence tag joined to their 5'-termini and second-round first-strand cDNA molecules that have the DNA sequence tag joined to their 3'-termini are synthesized;

(I) incubating the solution from step (H) under conditions and for sufficient time wherein RNA that is annealed to DNA is degraded (e.g., by incubating with RNase H or in an alkaline solution, after which the RNase H is inactivated or the alkaline solution is neutralized, respectively);

(J) incubating a solution containing the second-round first-strand cDNA molecules that have the DNA sequence tag joined to their 3'-termini, plus the second-round second-strand cDNA synthesis primer and either at least one of the at least one the RNA-dependent DNA polymerases or the DNA-template-specific DNA polymerase, under conditions and for sufficient time wherein second-round double-stranded cDNA molecules that contain a double-stranded RNA polymerase promoter are synthesized; and (K) incubating the solution from step (J), containing second-round double-stranded cDNA molecules, plus the second-round RNA polymerase, under conditions and for sufficient time wherein multiple copies of sense RNA molecules are synthesized, each of which, exhibits substantially the same sequence as one of the one or more RNA molecules of interest in the sample and has the RNA sequence tag joined to its 5'-terminus.

In some preferred embodiments of the method further comprising steps (G) through (K), the at least one RNA-dependent DNA polymerase used in step (H) and, optionally, in step (J), is the same at least one RNA-dependent DNA polymerase that is used in step (B) or in step (D). In some preferred embodiments, the at least one RNA-dependent DNA polymerase used in step (H) and, optionally, in step (J), is AMV reverse transcriptase or RNase H-minus AMV reverse transcriptase. In some embodiments wherein the DNA-template-specific DNA polymerase is used in step (J), it is a thermostable DNA polymerase.

In some preferred embodiments of the method comprising steps (A) through (F) or steps (A) through (K), the relative amounts (or abundance) of each of the sense RNA molecules that are synthesized, each of which has the RNA sequence tag joined to its 5'-terminus and which exhibits substantially the same sequence as one of the one or more RNA molecules of interest in the sample, are substantially the same in the solution of step (F) or step (K), respectively, as in the sample that contains the one or more RNA molecules of interest that is provided in step (A).

In some preferred embodiments of the method comprising steps (A) through (F) or steps (A) through (K), substantially no RNA molecules are synthesized in the absence of the sample containing the one or more RNA molecules of interest. By "substantially no RNA molecules are synthesized in the absence of the sample containing the one or more RNA molecules of interest," we mean that, when using the method, the amount RNA that is synthesized in the absence of a sample that contains the one or more RNA molecules of interest is less than about 10%, less than about 5%, or even more preferably, less than about 2% or less than about 1% of the amount of RNA synthesized in the presence of a sample that contains the one or more RNA molecules of interest. One way to quantify the amount of RNA synthesized is to remove the nucleotides from the RNA from each reaction (e.g., using a mini-column; e.g., a Qiagen mini-column), and then quantify the RNA based on the UV absorption at 260 nm. Alternatively, the products obtained in step (F) in the presence and the absence of the sample can be analyzed by agarose gel electrophoresis and quantified as described and illustrated in the Examples herein.

In some preferred embodiments of the method comprising all or a subset of steps (A) through (F) or steps (A) through (K), the one or more RNA molecules of interest comprise a multiplicity of RNA molecules. In some embodiments wherein the one or more RNA molecules of interest comprise a multiplicity of RNA molecules, the method may also result in synthesis of first-strand cDNA molecules that are complementary to one or more RNA molecules that are not of interest in addition to synthesizing first-strand cDNA molecules that are complementary to the one or more RNA molecules of interest in the sample. However, in preferred embodiments, the method results in synthesis of first-strand cDNA molecules that are complementary to only or predominantly the RNA molecules of interest in the sample. For example, in some embodiments, the one or more RNA molecules of interest comprise substantially all polyadenylated mRNA molecules in the sample, wherein a first-strand cDNA synthesis primer that anneals to the poly(A) tails of the mRNA molecules of interest is used in step (B) of the method. For example, in some other embodiments, the one or more RNA molecules of interest in the sample comprise substantially all miRNA molecules, or miRNA molecules to which a poly(A) tail or another tail has been added as described herein. For example, in some embodiments, the sample provided in step (A) contains a multiplicity of RNA molecules that have been separated by size and that are of a desired size range (e.g., miRNA).

In some preferred embodiments of the method comprising all or a subset of steps (A) through (F) or steps (A) through (K), one or more RNA first-strand cDNA synthesis primers (i.e., which comprises ribonucleotides), at least one of which is complementary to each RNA molecule of interest in the sample, is provided in step (A) and is used in step (B) for synthesis of first-strand cDNA molecules that are complementary to the RNA molecules of interest. In some preferred embodiments of the method comprising all or a subset of steps (A) through (F) or steps (A) through (K), an oligoribonucleotide is provided in step A, and is included in the solution as a first-strand cDNA synthesis primer in step (B) and/or step (H). In some of these embodiments, the 5'-portion of the oligoribonucleotide exhibits an anti-sense promoter sequence for the RNA polymerase provided in step (A).

In some embodiments of the method comprising all or a subset of steps (A) through (F) or steps (A) through (K), an oligodeoxyribonucleotide is provided in step A, and is included in the solution as a first-strand cDNA synthesis primer in step (B) and/or step (H). In some embodiments, the 5'-portion of the oligodeoxyribonucleotide first-strand cDNA synthesis primer exhibits an anti-sense promoter sequence for the RNA polymerase provided in step (A). In some embodiments, the 5'-portion of the oligodeoxyribonucleotide first-strand cDNA synthesis primer exhibits an anti-sense promoter sequence for a second RNA polymerase that is different from the RNA polymerase provided in step (A). In some preferred embodiments wherein an oligodeoxyribonucleotide is provided in step A and is included in the solution as a first-strand cDNA synthesis primer in step (B), step (C) additionally comprises the sub-steps of: providing one or more ssDNA exonucleases selected from the group consisting of exonuclease I; exonuclease VII; and Rec J exonuclease; and incubating in the solution with the one or more ssDNA exonucleases under conditions and for sufficient time wherein the one or more first-strand cDNA synthesis primers are degraded.

In some embodiments of the method comprising all or a subset of steps (A) through (F) or steps (A) through (K), no oligonucleotide is provided and first-strand cDNA molecules are synthesized in step (B) in the absence of an added oligonucleotide for use as a first-strand cDNA synthesis primer.

In some preferred embodiments of the method comprising all or a subset of steps (A) through (F) or steps (A) through (K), the 5'-portion of the terminal tagging oligoribonucleotide does not exhibit a sense promoter sequence or an anti-sense promoter sequence for an RNA polymerase promoter. In some other embodiments of the method comprising all or a subset of steps (A) through (F) or steps (A) through (K), the 5'-portion of the terminal tagging oligoribonucleotide exhibits an anti-sense sequence for an RNA polymerase promoter.

The invention also includes embodiments comprising a method comprising or consisting of one or more of any of the individual steps of a method disclosed herein (e.g., a subset consisting of one or more individual steps of the methods comprising steps (A) through (F), or steps (A) through (K); e.g., to synthesize only those molecules that are desired for an intended purpose), in which embodiments, only those components required therein are provided (e.g, in step (A) or step (G), respectively).

For example, one preferred method is a subset of the method comprising all or a subset of steps (A) through (F) that is used for synthesizing first-strand cDNA molecules that are complementary to one or more RNA molecules of interest in the sample and that have a desired arbitrary DNA sequence tag joined to their 3'-termini (e.g., FIG. 1 and FIG. 2), the method comprising the steps of:

(A) providing:

the sample containing one or more RNA molecules of interest;

the least one RNA-dependent DNA polymerase; and the terminal tagging oligoribonucleotide comprising ribonucleotides (rTTO), which terminal tagging oligoribonucleotide comprises or consists of a 5'-portion and 3'-portion, wherein the 5'-portion exhibits a sequence that is complementary to the sequence of the DNA sequence tag that it is desired to join to the 3'-termini of first-strand cDNA molecules, and wherein the 3'-portion comprises or consists of at least three random nucleotides (e.g., 3 to 8 random nucleotides; e.g., 7 random nucleotides), of which the 3'-terminal nucleotide is blocked so that it is not capable of being extended by a DNA polymerase;

(B) incubating a solution containing the sample with the one or more RNA molecules of interest, plus the at least one RNA-dependent DNA polymerase, under conditions and for sufficient time wherein first-strand cDNA molecules that are complementary to the RNA molecules of interest are synthesized;

(C) incubating the solution from step (B) under conditions and for sufficient time wherein RNA that is annealed to DNA and single-stranded RNA are degraded; and (D) incubating the solution from step (C) containing the first-strand cDNA molecules, plus the terminal tagging oligoribonucleotide and the at least one RNA-dependent DNA polymerase, under conditions and for sufficient time wherein the terminal tagging oligoribonucleotide anneals to the first-strand cDNA molecules and the 3'-termini of the first-strand cDNA molecules are extended using the terminal tagging oligoribonucleotide as a template, wherein first-strand cDNA molecules that have the DNA sequence tag joined to their 3'-termini are synthesized.

For example, another preferred method is a subset of the method comprising steps (A) through (F) that is used for synthesizing double-stranded cDNA molecules, which double-stranded cDNA molecules optionally contain an RNA polymerase promoter (e.g., see FIG. 3), wherein the method additionally comprises the steps of:

(A) additionally providing:

first-strand cDNA molecules that have the DNA sequence tag joined to their 3'-termini from step (D);

optionally, the at least one RNA-dependent DNA polymerase or the DNA-template-specific DNA polymerase provided in step (A); and a second-strand cDNA synthesis primer comprising or consisting of an oligodeoxyribonucleotide that comprises a 5'-portion and a 3'-portion, wherein the 5'-portion exhibits an arbitrary sequence or, optionally, wherein the 5'-portion exhibits at least a portion of an anti-sense promoter sequence for a double-stranded RNA polymerase promoter, and the 3'-portion has a 3'-hydroxyl group and exhibits a sequence that is complementary to the DNA sequence tag that is joined to the 3'-termini of the first-strand cDNA molecules; and (E) incubating a solution containing the first-strand cDNA molecules that have the DNA sequence tag joined to their 3'-termini, plus the second-strand cDNA synthesis primer and the at least one RNA-dependent DNA polymerase or the DNA-template-specific DNA polymerase, under conditions and for sufficient time wherein double-stranded cDNA molecules are synthesized.

In some embodiments of the method comprising steps (A) through (F) or steps (A) through (K), the method additionally comprises using the double-stranded cDNA molecules that contain the double-stranded RNA polymerase promoter to synthesize multiple copies of sense RNA molecules that exhibit substantially the same sequences as the RNA molecules of interest in the sample, each of which has the RNA sequence tag that exhibits the desired arbitrary sequence joined to its 5'-terminus (e.g., see FIG. 4).

In some preferred embodiments, following synthesis of the first-strand cDNA molecules that have the DNA sequence tag joined to their 3'-termini, step (D) additionally comprises the sub-step of incubating the reaction mixture under conditions and for sufficient time wherein RNA that is annealed to DNA and single-stranded RNA are degraded.

In some preferred embodiments, RNase H and a single-strand-specific RNase are additionally provided in step (A); and are used in step (C) and/or in the sub-step of step (D) comprising incubating the reaction mixture under conditions and for sufficient time wherein RNA that is annealed to DNA and single-stranded RNA are degraded. In these embodiments, the reaction mixture is incubated with the RNase H and the single-strand-specific RNase under conditions and for sufficient time wherein RNA that is annealed to DNA and single-stranded RNA are degraded. In some preferred embodiments, the RNase H that is provided in step (A) is *E. coli* RNase H and the single-strand-specific RNase that is provided in step (A) is *E. coli* RNase I.

In some preferred embodiments, step (C) and/or step (D) additionally comprises: additionally providing RNase H and a single-strand-specific RNase (e.g., RNase I); contacting the reaction mixture with the RNase H and single-strand-specific RNase under conditions and for sufficient time wherein RNA that is annealed to DNA and single-stranded RNA are digested; and then inactivating the RNase H and single-strand-specific RNase.

In some other embodiments, an alkaline solution is additionally provided in step (A), and step (C) and/or the sub-step of step (D) comprises incubating the reaction mixture with the alkaline solution under conditions and for sufficient time wherein RNA that is annealed to DNA and single-stranded RNA are degraded. In some embodiments, the alkaline solution is neutralized after degrading the RNA that is annealed to DNA and the single-stranded RNA.

In some preferred embodiments, the RNA-dependent DNA polymerase is not inactivated following step (B). However, in some embodiments, step (B) additionally comprises the sub-step of inactivating the RNA-dependent DNA polymerase. In embodiments wherein the RNA-dependent DNA polymerase is inactivated in step (B), additional RNA-dependent DNA polymerase is provided, and is used in step (D), which additional RNA-dependent DNA polymerase can be the same as or different from the RNA-dependent DNA polymerase used in step (B). In some preferred embodiments, the RNA-dependent DNA polymerase is not inactivated following synthesis of the first-strand cDNA molecules that have the DNA sequence tag joined to their 3'-termini in step (D). However, in some embodiments, step (D) additionally comprises the sub-step of inactivating the RNA-dependent DNA polymerase.

In embodiments wherein the RNA-dependent DNA polymerase is inactivated in step (D), the DNA-template-specific DNA polymerase is provided, and is used in step (E), which DNA-template-specific DNA polymerase can be the same as or different from the RNA-dependent DNA polymerase used in steps (B) or (D). In some other embodiments wherein the RNA-dependent DNA polymerase is not inactivated in step (D), the RNA-dependent DNA polymerase is also used as the DNA-template-specific DNA polymerase in step (E). In some preferred embodiments, step (E) of the method further comprises the sub-step of inactivating the DNA-template-specific DNA polymerase.

Using AMV reverse transcriptase as the RNA-dependent DNA polymerase in step (B), the applicants found that the quantity and size range of the sense RNA molecules that have an RNA sequence tag joined to their 5'-termini that were synthesized in step (F) were similar both when the RNA-dependent DNA polymerase was inactivated and when it was not inactivated following step (B). Therefore, in some preferred embodiments, the RNA-dependent DNA polymerase is not inactivated following synthesis of the first-strand cDNA molecules in step (B). In some other embodiments, the RNA-dependent DNA polymerase is inactivated after synthesis of the first-strand cDNA molecules in step (B). Using AMV reverse transcriptase as the RNA-dependent DNA polymerase in step (D), the applicants found that the quantity and size range of the sense RNA molecules that have an RNA sequence tag joined to their 5'-termini that were synthesized in step (F) were similar both when the RNA-dependent DNA polymerase was inactivated and when it was not inactivated following synthesis of the first-strand cDNA molecules that have a DNA sequence tag on their 3' termini in step (D). Thus, in some preferred embodiments, the RNA-dependent DNA polymerase is not inactivated after synthesis of the first-strand cDNA molecules that have the DNA sequence tag on their 3'-termini in step (D). In some other embodiments, the RNA-dependent DNA polymerase is inactivated after synthesis of the first-strand cDNA molecules that have the DNA sequence tag on their 3'-termini in step (D). Using AMV reverse transcriptase as the DNA-template-specific DNA polymerase in step (E), the applicants found that the quantity of the sense RNA molecules that have an RNA sequence tag joined to their 5'-termini that were synthesized in step (F) was reduced and the size range of the products was shorter when the DNA-template-specific DNA polymerase was not inactivated after step (E) than when it was inactivated following step (E). Thus, in some preferred embodiments, the DNA-template-specific DNA polymerase is inactivated following synthesis of the double-stranded cDNA molecules that contain a double-stranded RNA polymerase promoter in step (E) of the method.

In some preferred embodiments comprising steps (A) through (F) of the method, the first-strand cDNA molecules that have the DNA sequence tag joined to their 3'-termini obtained in step (D) of the method are further used in step (E) as templates for synthesizing multiple copies of the double-stranded cDNA molecules that contain a double-stranded RNA polymerase promoter using the polymerase chain reaction (PCR). Thus, in one preferred embodiment of the method, the DNA-template-specific DNA polymerase provided in step (A) is a thermostable DNA polymerase or a blend of thermostable DNA polymerases (e.g., Taq DNA polymerase or FailSafe™ DNA Polymerase from EPICENTRE Biotechnologies, Madison, Wis., USA) that is capable of being used in the polymerase chain reaction (PCR), the second-strand cDNA synthesis primer that is provided in step (A) is used as a first PCR primer and is capable of annealing to the first-strand cDNA molecules that have DNA sequence tag joined to their 3'-termini, and step (E) of the method additionally comprises the sub-steps of:

(1) providing a second PCR primer consisting of an oligodeoxyribonucleotide that comprises a 5'-portion and a 3'-portion, wherein the 5'-portion exhibits an arbitrary sequence, and the 3'-portion has a 3'-terminal nucleotide that has a 3'-hydroxyl group and exhibits a sequence that is complementary to a portion of the second-strand cDNA molecules, which in turn are complementary to the first-strand cDNA molecules that have DNA sequence tag joined to their 3'-termini; and (2) incubating the first-strand cDNA molecules that have the DNA sequence tag joined to their 3'-termini with the second-strand cDNA synthesis primer, the second PCR primer, and the DNA-template-specific DNA polymerase in a solution under PCR reaction conditions and for sufficient time, wherein multiple copies of double-stranded cDNA molecules that contain the double-stranded RNA polymerase promoter are synthesized.

In some embodiments, the method comprises synthesizing an additional round of additional first-strand cDNA molecules that have the DNA sequence tag on their 3'-termini, the method additionally comprising the steps of:

(G) providing:
the sense RNA molecules that have the RNA sequence tag joined to their 5'-termini from step (F) of the first round of the method;
second-round first-strand cDNA synthesis primers comprising or consisting of one or more oligonucleotides, at least one of which is complementary to each of the sense RNA molecules that have the RNA sequence tag joined to their 5'-termini that are provided in step (G);
a second-round RNA-dependent DNA polymerase; and (H) incubating the sense RNA molecules that have the RNA sequence tag joined to their 5'-termini with the second-round first-strand cDNA synthesis primers and the second-round RNA-dependent DNA polymerase in a solution under conditions and for sufficient time wherein the second-round first-strand cDNA synthesis primers anneal to the sense RNA molecules that have the RNA sequence tag joined to their 5'-termini and additional first-strand cDNA molecules that have the DNA sequence tag joined to their 3'-termini are synthesized.

In some embodiments, the method additionally comprises the step of:

(I) incubating the solution from step (H) under conditions and for sufficient time wherein RNA that is annealed to DNA is degraded (e.g., by incubating with RNase H or in an alkaline solution, after which the RNase H is inactivated or the alkaline solution is neutralized, respectively).

In some embodiments, the method comprises synthesizing an additional round of double-stranded cDNA molecules that have a double-stranded RNA polymerase promoter, the method additionally comprising the steps of:

(G) providing:
a second-round second-strand cDNA synthesis primer, comprising or consisting of an oligodeoxyribonucleotide that has a 5'-portion and a 3'-portion, wherein the 5'-portion exhibits at least a portion of an anti-sense promoter sequence for a double-stranded RNA polymerase promoter, and the 3'-portion has a 3'-hydroxyl group and exhibits a sequence that is complementary to the DNA sequence tag that is joined to the 3'-termini of the first-strand cDNA molecules from step (D);
a second-round DNA-template-specific DNA polymerase that is capable of synthesizing DNA by extension of a primer using DNA as a template; and (J) incubating the solution containing the second-round first-strand cDNA molecules that have the DNA sequence tag joined to their 3'-termini with the second-round second-strand cDNA synthesis primer and the second-round DNA-template-specific DNA polymerase under conditions and for sufficient time wherein additional double-stranded cDNA molecules that contain a double-stranded RNA polymerase promoter are synthesized.

In some embodiments, step (G) of the method additionally comprises: providing an enzyme that is capable of joining a 3'-tag to the 3'-termini of the sense RNA molecules that have the RNA sequence tag joined to their 5'-termini and, prior to step (H), the method additionally comprises the step of contacting the sense RNA molecules that have the RNA sequence tag joined to their 5'-termini with the enzyme in a solution under conditions and for sufficient time wherein the 3'-tag, to which at least one of the second-round first-strand cDNA synthesis primers is capable of annealing, is joined to their 3'-termini. In some preferred embodiments of this aspect of the method, the enzyme that is capable of joining a 3'-tag to the 3'-termini of the sense RNA molecules is poly(A) polymerase, and step (G) additionally comprises the sub-step of: contacting the sense RNA molecules that have the RNA sequence tag joined to their 5'-termini with the poly(A) polymerase and ATP in a solution under conditions and for sufficient time wherein a poly(A) tail is added to the 3'-termini of the sense RNA molecules that have the RNA sequence tag joined to their 5'-termini, thereby providing in step (G), sense RNA molecules that have an RNA sequence tag joined to their 5'-termini and a poly(A) tail joined to their 3'-termini.

In some preferred embodiments, step (H) of the method further comprises the sub-step of: inactivating the second-round RNA-dependent DNA polymerase.

In some preferred embodiments, step (J) of the method further comprises the sub-step of: inactivating the second-round DNA-template-specific DNA polymerase.

In some preferred embodiments, the method further comprises performing one or more additional rounds of synthesis of first-strand cDNA molecules that have the DNA sequence tag joined to their 3'-termini, of double-stranded cDNA molecules, or of sense RNA molecules that have the RNA sequence tag joined to their 5'-termini by repeating any of steps (G) through (K) by providing, in step (G), the products of step (K) from the prior round. In some of these embodiments, the method is used to prepare: a multiplicity, a collection, or a library of all first-strand cDNA molecules that have the DNA sequence tag joined to their 3'-termini; a multiplicity, a collection, or a library of all double-stranded cDNA molecules; or multiplicity, a collection, or a library of all sense RNA molecules that have the RNA sequence tag joined to their 5'-termini; wherein the respective molecules synthesized are derived from RNA molecules of interest from a sample consisting of from approximately one to ten cells, ten to a hundred cells, a hundred to a thousand cells, a thousand to ten thousand cells, or greater than ten thousand cells. The method is highly sensitive. However, the sample is not limited with respect to the upper quantity of the RNA molecules of interest that can be amplified by increasing the scale of the reactions of the method or performing multiple reactions with each sample. In one preferred embodiment, the method is used to prepare a library comprising first-strand cDNA molecules that have the DNA sequence tag joined to their 3'-termini, a library of double-stranded cDNA molecules, or a library of sense RNA molecules that have the RNA sequence tag joined to their 5'-termini, wherein the respective molecules synthesized are derived from mRNA molecules of interest from a sample consisting of from one to about one to one hundred cells, a hundred to a thousand cells, a thousand to ten thousand cells, or greater than ten thousand cells, which cells can be from either a prokaryote or a eukaryote. In some embodiments, the first-strand cDNA molecules that have the DNA sequence tag on their 3'-termini and/or the double-stranded cDNA molecules synthesized using the method are used as templates for NexGen sequencing reactions or are used to synthesize NexGen sequencing templates.

In some embodiments of any of the above methods comprising steps (A) through (F) or steps (A) through (K), the 5'-portion of the terminal tagging oligoribonucleotide provided in step (A) exhibits a complete anti-sense promoter sequence of a double-stranded RNA polymerase promoter that is recognized by the RNA polymerase, which anti-sense promoter sequence is identical to that exhibited by the 5'-portion of the second-strand cDNA synthesis primer provided in step (A) or that exhibited by the 5'-portion of the second-round second-strand cDNA synthesis primer provided in step (G).

One other preferred embodiment of the invention is a method for synthesizing multiple copies of RNA molecules that exhibit substantially the same sequences as the RNA or DNA molecules of interest in a sample, each of which sense RNA molecules has an RNA sequence tag that exhibits a desired arbitrary sequence joined to its 5'-terminus, the method comprising the steps:

1st, providing:
  a sample containing one or more nucleic acid molecules of interest (e.g., either one or more RNA or one or more DNA molecules of interest, e.g., which is denatured so that it is single-stranded and, if desired, which is fragmented);
  at least one RNA-dependent DNA polymerase (e.g., AMV reverse transcriptase, or MMLV reverse transcriptase, or a mixture thereof) if the nucleic acid molecule of interest is RNA; or
  at least one DNA-template-specific DNA polymerase (e.g., MMLV reverse transcriptase, AMV reverse transcriptase or FailSafe™ DNA polymerase) if the nucleic acid molecule of interest is DNA;
  a first-strand cDNA synthesis primer comprising deoxyribonucleotides, which first-strand cDNA synthesis primer comprises or consists of a 5'-portion and 3'-portion; wherein the 5'-portion comprises or consists of (a) a segment that exhibits a sense promoter sequence for a double-stranded RNA polymerase promoter, (b) optionally, a segment that is 3'- of the sense promoter sequence that exhibits sequence which, when present in double-stranded DNA, can be cleaved by a restriction endonuclease (preferably a rare cutter restriction endonuclease; e.g., Not I or Asc I), and (c) optionally, one or more segments 5'- of or 3'- of the sense promoter sequence; and wherein the 3'-portion has an hydroxyl group on its 3'-terminus and exhibits a sequence that is complementary to at least one of the one or more Nucleic acid molecules of interest in the sample (e.g. an oligo(dT)n sense promoter primer and/or a sense promoter primer that exhibits a random sequence in its 3'-portion and/or one or more sense promoter primers, each of which exhibits a specific sequence in its 3'-portion that is complementary to the one or more nucleic acid molecules of interest);
  a terminal tagging oligonucleotide comprising or consisting of ribonucleotides (rTTO), which terminal tagging oligoribonucleotide comprises or consists of a 5'-portion and 3'-portion, wherein the 5'-portion exhibits a sequence that is complementary to the sequence of the DNA sequence tag that it is desired to join to the 3'-termini of first-strand cDNA molecules, and wherein the 3'-portion comprises or consists of at least three random nucleotides (e.g., 3 to 8 random nucleotides; e.g., 7 random nucleotides), of which the 3'-terminal nucleotide is blocked so that it is not capable of being extended by a DNA polymerase;

a second-strand cDNA synthesis primer, comprising or consisting oligodeoxyribonucleotides that has a 3'-hydroxyl group that exhibits a sequence that is identical to at least a portion of the 5'-portion of the terminal tagging oligonucleotide;

optionally, if the nucleic acid molecule of interest is RNA, a DNA-template-specific DNA polymerase (e.g., MMLV reverse transcriptase, AMV reverse transcriptase or FailSafe™ DNA polymerase);

a DNA ligase (e.g., T4 DNA ligase); and an RNA polymerase (e.g., a T7-type RNA polymerase; e.g., T7, T3 or SP6 RNA polymerase) that is capable of synthesizing RNA using a DNA template that is joined to a double-stranded RNA polymerase promoter, wherein the 3'-terminus of the template strand exhibits a sequence that is complementary to the anti-sense promoter sequence exhibited by the 5'-portion of the second-strand cDNA synthesis primer;

2nd, incubating a solution containing the sample with the one or more Nucleic acid molecules of interest, plus at least one of the at least one RNA-dependent DNA polymerases and the first-strand cDNA synthesis primer, under conditions and for sufficient time wherein first-strand cDNA molecules that are complementary to the Nucleic acid molecules of interest are synthesized;

3rd, incubating the solution from 2nd step under conditions and for sufficient time wherein RNA that is annealed to DNA and single-stranded RNA are degraded (e.g., in the presence of RNase H and a single-strand-specific RNase (e.g., RNase I), after which the RNase H and the single-strand-specific RNase are inactivated (e.g., by heating to 95 degrees centigrade for 3 to 10 minutes);

4th, incubating the solution from the 3rd step containing the first-strand cDNA molecules, plus the terminal tagging oligoribonucleotide and at least one of the at least one RNA-dependent DNA polymerases, under conditions and for sufficient time wherein the terminal tagging oligoribonucleotide anneals to the first-strand cDNA molecules and the 3'-termini of the first-strand cDNA molecules are extended using the terminal tagging oligoribonucleotide as a template, wherein first-strand cDNA molecules that have the DNA sequence tag joined to their 3'-termini are synthesized, and then, optionally, incubating the solution under conditions and for sufficient time wherein RNA that is annealed to DNA and single-stranded RNA are degraded (e.g., in the presence of RNase H and a single-strand-specific RNase (e.g., RNase I), after which the RNase H and the single-strand-specific RNase are inactivated (e.g., by heating to 95 degrees centigrade for 3 to 10 minutes));

5th, incubating the solution from the 4th step containing the first-strand cDNA molecules that have the DNA sequence tag joined to their 3'-termini, plus the second-strand cDNA synthesis primer and either at least one of the at least one RNA-dependent DNA polymerases or the DNA-template-specific DNA polymerase, under conditions and for sufficient time wherein double-stranded cDNA molecules that contain a double-stranded RNA polymerase promoter are synthesized; and then, optionally, repairing the ends of the double-stranded cDNA molecules (e.g., by incubating in the presence of T4 DNA polymerase, dNTPs, T4 polynucleotide kinase, and ATP under conditions and for sufficient time wherein the ends of the double-stranded cDNA molecules are blunt and the 5'-termini are monophosphorylated; e.g., using the End-It™ DNA End Repair Kit, EPICENTRE, Madison, Wis., USA);

6th, incubating the solution from the 5th step containing the double-stranded cDNA molecules, plus the DNA ligase under conditions and for sufficient time wherein the double-stranded cDNA molecules are self-ligated to form circular double-stranded cDNA molecules; and then, optionally, incubating the circular double-stranded cDNA molecules in a solution with the rare cutter restriction endonuclease under conditions and for sufficient time wherein the circular double-stranded cDNA molecules are cleaved and linear double-stranded cDNA molecules are generated; and 7th, incubating the solution from the 6th step containing circular or the linear double-stranded cDNA molecules, plus the RNA polymerase, under conditions and for sufficient time wherein multiple copies of RNA molecules are synthesized, each of which, exhibits a sequence that is substantially identical to one of the one or more nucleic acid molecules of interest in the sample, and has an RNA sequence tag joined to its 5'-terminus.

The invention comprises embodiments of the above method comprising all or a subset of the 1st through the 7th steps. In some embodiments of the method comprising all or a subset of the 1st through the 7th steps, a terminal tagging oligonucleotide comprising or consisting of deoxyribonucleotides (dTTO) is used in place of the rTTO. In some embodiments wherein the method is used to amplify one or more specific nucleic acid molecules in the sample, the 3'-portion of the sequences terminal tagging oligonucleotide comprises or consists of one or more specific sequences, each of which is complementary to a sequence exhibited by the 3'-portion of at least one of the nucleic acid molecules of interest in the sample. In some embodiments, the first-strand cDNA synthesis primer and the second-strand cDNA synthesis primer each have a 5'-phosphate group and it is not necessary to phosphorylate using T4 polynucleotide kinase and ATP in the 5th step.

The present invention also provides methods to use the first-strand cDNA molecules that have a DNA sequence tag on their 3'-termini synthesized in step (D) in order to synthesize anti-sense RNA molecules that have an anti-sense RNA sequence tag on their 3'-termini, which molecules can be useful for certain applications (e.g., to prepare labeled target RNA for analysis on microarrays of sense probes). Thus, in some embodiments, PCR is used to synthesize double-stranded DNA molecules that contain a double-stranded promoter (which double-stranded cDNA molecules can be used as substrates for synthesis of RNA molecules which are anti-sense with respect to the RNA molecules of interest in the sample.

Thus, one embodiment comprises a method to synthesize anti-sense RNA molecules with respect to the RNA molecules of interest in the sample, each of which has an anti-sense RNA sequence tag joined to its 3'-terminus, the method comprising:

1. providing:
   first-strand cDNA molecules that have the DNA sequence tag joined to their 3'-termini from step (D) of the method comprising steps (A) through (D) above;
   a first PCR primer that is complementary to the DNA sequence tag that is joined to the 3'-termini of the first-strand cDNA molecules in step (D) of the method;
   a second PCR primer that has a 5'-portion and a 3'-portion, wherein the 5'-portion comprises or consists of a 5'-flap (meaning that it is not complementary to the second-strand cDNA molecules and forms an unhybridized flap when the PCR primer is annealed to second-strand cDNA molecules), which 5'-flap exhibits an anti-sense promoter sequence of a double-stranded RNA polymerase promoter, and wherein the 3'-portion is complementary to the 3'-termini of the RNA molecules of interest in the sample (i.e., the 3'-portion exhibits a sequence that is identical to at least the 3'-portion of the first-strand cDNA synthesis primers that were used in step (B) of the method comprising steps (A) through (D) above;
  a thermostable DNA polymerase or a blend of thermostable DNA polymerases (e.g., Taq DNA polymerase or FailSafe™ DNA Polymerase from EPICENTRE Biotechnologies, Madison, Wis., USA) that is capable of being used in the polymerase chain reaction (PCR), and
2. incubating the first-strand cDNA molecules that have the DNA sequence tag joined to their 3'-termini from step (D) with the first PCR primer, the second PCR primer, and the thermostable DNA polymerase or blend of thermostable DNA polymerases in a solution under PCR reaction conditions and for sufficient time, wherein multiple copies of double-stranded cDNA molecules that contain the double-stranded RNA polymerase promoter are synthesized; and
3. incubating the double-stranded cDNA molecules with the RNA polymerase that recognizes and binds the double-stranded RNA polymerase promoter under conditions and for sufficient time wherein multiple copies of anti-sense RNA molecules are synthesized, each of which exhibits a sequence that is complementary to an RNA molecule of interest in the sample, and each of which has an anti-sense RNA sequence tag joined to its 3'-terminus.

The invention also comprises methods that use a promoter primer for synthesizing first-strand cDNA molecules that have a DNA sequencing tag on their 3' termini and tagged double-stranded cDNA molecules in order to generate templates for synthesis of anti-sense RNA molecules from RNA molecules of interest in a sample. Thus, these methods combine methods known in the art (e.g., the methods described in U.S. Pat. Nos. 5,545,522; 5,716,785; and 5,891,636, herein incorporated by reference in their entireties) together with the method of the present invention for joining a DNA sequence tag to the 3'-termini of the first-strand cDNA molecules, which DNA sequence tag provides a priming site for synthesis of double-stranded cDNA molecules that have a double-stranded RNA polymerase promoter, which in turn, are substrates for synthesis of anti-sense RNA molecules that have an RNA sequence tag joined to their 3'-termini. The presence of the RNA sequence tag on the 3'-termini of anti-sense RNA molecules is very beneficial because it provides a fixed 3'-terminal priming site that enables maintenance of the sizes of the anti-sense RNA molecules synthesized when two or more rounds of amplification are desirable (e.g., in order to produce a sufficient amount of anti-sense RNA molecules corresponding to mRNA from a small number of cells for use in NexGen sequencing, or, if labeled, for use as labeled target for microarray analysis).

Thus, one other embodiment of the invention is a method for synthesizing multiple copies of anti-sense RNA molecules that exhibit substantially the same sequences as the one or more RNA molecules of interest in a sample, each of which molecules is joined, at its 3'-terminus, to an RNA sequence tag that exhibits a desired arbitrary sequence, the method comprising the steps of:
  (1) providing:
  a sample containing one or more RNA molecules of interest;
  a first-round first-strand cDNA synthesis primer comprising or consisting of oligodeoxyribonucleotide promoter primer that comprises a 5'-portion and a 3'-portion, wherein the 5' portion exhibits an anti-sense promoter sequence of a double-stranded RNA polymerase promoter, and wherein the 3'-portion is complementary to the 3'-portions of the one or more RNA molecules of interest in the sample;
  at least one RNA-dependent DNA polymerase;
  a terminal tagging oligoribonucleotide comprising ribonucleotides (rTTO), which terminal tagging oligoribonucleotide comprises a 5'-portion and 3'-portion, wherein the 5'-portion exhibits a sequence that is complementary to the sequence of the first DNA sequence tag that it is desired to join to the 3'-termini of first-strand cDNA molecules, but which 5'-portion does not exhibit a proto-promoter sequence, and wherein the 3'-portion consists of at least three random nucleotides (e.g., 3 to 8 random nucleotides, e.g., 7 random nucleotides), of which the 3'-terminal nucleotide is blocked so that it is not capable of being extended by a DNA polymerase;
  a DNA-template-specific DNA polymerase that is capable of synthesizing DNA by extension of a primer using DNA as a template;
  a first-round second-strand cDNA synthesis primer, comprising or consisting of an oligodeoxyribonucleotide that comprises a 5'-portion and a 3'-portion, wherein the 5'-portion is either absent or exhibits a desired arbitrary sequence (e.g., for a particular purpose), and the 3'-portion exhibits a sequence that is identical to at least a portion of the 5'-portion of the terminal tagging oligoribonucleotide; and
  an RNA polymerase that recognizes the double-stranded RNA polymerase promoter for which sense promoter sequence is exhibited by the 5'-portion of the first-round first-strand cDNA synthesis primer;
  (2) incubating a solution with the sample containing the one or more RNA molecules of interest, the first-round first-strand cDNA synthesis primer (e.g., that is present in the solution at a concentration of less than or equal to about 5 picomoles per 5 microliters; e.g., preferably at a concentration of about 2.5 picomoles per microliter), and the RNA-dependent DNA polymerase under conditions and for sufficient time wherein first-strand cDNA molecules that are complementary to the RNA molecules of interest are synthesized;
  (3) incubating the solution from step (2) under conditions and for sufficient time wherein RNA that is annealed to DNA and single-stranded RNA are degraded; and optionally, also incubating with at least one single-strand-specific DNA exonuclease (e.g., selected from among exonuclease I; exonuclease VII; and Rec J exonuclease) under conditions and for sufficient time wherein the first-round first-strand cDNA synthesis primer is degraded, and then inactivating the at least one single-strand-specific DNA exonuclease;
  (4) incubating the solution from step (3) containing the first-strand cDNA molecules, plus the terminal tagging oligoribonucleotide and the RNA-dependent DNA polymerase, under conditions and for sufficient time wherein the terminal tagging oligoribonucleotide anneals to the first-strand cDNA molecules and the 3'-termini of the first-strand cDNA molecules are extended using the terminal tagging oligoribonucleotide as a template, wherein first-strand cDNA molecules that have a first DNA sequence tag joined to their 3'-termini are synthesized;
  (5) incubating the solution from step (4) containing the first-strand cDNA molecules that have the first DNA sequence tag joined to their 3'-termini, plus the first-round second-strand cDNA synthesis primer and the DNA-template-specific DNA polymerase, under conditions and for sufficient time wherein double-stranded cDNA molecules that contain a double-stranded RNA polymerase promoter that is recognized by the RNA polymerase are synthesized;

(6) incubating the solution from step (5) containing double-stranded cDNA molecules, plus the RNA polymerase that recognizes and binds the double-stranded RNA polymerase promoter, under conditions and for sufficient time wherein multiple copies of anti-sense RNA molecules that exhibit sequences that are complementary to the one or more RNA molecules of interest in the sample, each of which has a first RNA sequence tag joined to its 3'-terminus, are synthesized.

In some embodiments, the anti-sense RNA products of the first round of RNA synthesis in step (6) are used to synthesize additional rounds of anti-sense RNA molecules that have the first RNA sequence tag joined to their 3'-termini.

Thus, after the first round of synthesis of anti-sense RNA molecules that have a first RNA sequence tag joined to their 3'-termini, one method for a second round of amplification comprises:

(1a) providing:
  a second-round first-strand cDNA synthesis primer comprising or consisting of an oligodeoxyribonucletide that comprises a 5'-portion and a 3'-portion, wherein the 5' portion is either absent or exhibits a desired arbitrary sequence, and wherein the 3'-portion exhibits a sequence that is identical to at least a portion of the sequence exhibited by the 5'-portion of terminal tagging oligoribonucleotide;
  a second-round second-strand cDNA synthesis primer comprising or consisting of an oligodeoxyribonucleotide promoter primer that comprises a 5'-portion and a 3'-portion, wherein the 5'-portion exhibits an anti-sense promoter sequence for a double-stranded RNA polymerase promoter, and the 3'-portion exhibits a sequence that is identical to at least a portion of the sequence exhibited by the 3'-portion of the first-round first-strand cDNA synthesis primer;
  a second RNA polymerase that recognizes the double-stranded RNA polymerase promoter for which the anti-sense promoter sequence is exhibited by the 5'-portion of the second-round second-strand cDNA synthesis primer;

(7a) incubating a solution containing the anti-sense RNA molecules that have the first RNA sequence tag on their 3'-termini (from step (6) of the first round), the second-round first-strand cDNA synthesis primer, and the RNA-dependent DNA polymerase under conditions and for sufficient time wherein second-round first-strand cDNA molecules are synthesized;

(8a) incubating the solution from step (7a) containing the second-round first-strand cDNA molecules, plus the second-round second-strand cDNA synthesis primer and the DNA-template-specific DNA polymerase, under conditions and for sufficient time wherein double-stranded cDNA molecules that contain a double-stranded RNA polymerase promoter are synthesized; and (9a) incubating the solution from step (8a) containing double-stranded cDNA molecules, plus the second RNA polymerase, under conditions and for sufficient time wherein multiple copies of anti-sense RNA molecules that exhibit sequences that are complementary to the one or more RNA molecules of interest in the sample, each of which has the first RNA sequence tag joined to its 3'-terminus, are synthesized. Thus, in this embodiment, the second round of amplification uses a second-round second-strand cDNA synthesis primer, wherein its 5'-portion serves as a template for extension of the 3'-termini of the second-round first-strand cDNA molecules, thereby joining the sense promoter sequence of the double-stranded RNA polymerase promoter thereto. This yields additional anti-sense RNA molecules that have the first RNA sequence tag joined to their 3'-termini.

The anti-sense RNA products of the first round of RNA synthesis in step (6) above can also be used to synthesize sense RNA molecules that have a second RNA sequence tag joined to their 5'-termini.

Thus, after the first round of synthesis of anti-sense RNA molecules that have a first RNA sequence tag joined to their 3'-termini, one other method for a second round of amplification comprises:

(1b) providing:
  a second-round first-strand cDNA synthesis primer comprising or consisting of an oligodeoxyribonucleotide promoter primer that comprises a 5'-portion and a 3'-portion, wherein the 5' portion exhibits an anti-sense promoter sequence for a double-stranded RNA polymerase promoter, and the 3'-portion exhibits a sequence that is complementary to the first RNA sequence tag, which, in turn, is identical to the sequence exhibited by at least a portion of the 5'-portion of terminal tagging oligoribonucleotide;
  a second-round second-strand cDNA synthesis primer comprising or consisting of an oligodeoxyribonucleotide that comprises a 5'-portion and a 3'-portion, wherein the 5' portion is either absent or exhibits a desired arbitrary sequence, and wherein the 3'-portion exhibits a sequence that is identical to the 3'-portion of the first-round first-strand cDNA synthesis primer;
  a second RNA polymerase that recognizes the double-stranded promoter for which the sense promoter sequence is exhibited by the 5'-portion of the second-round first-strand cDNA synthesis primer; and (7b) incubating a solution containing the anti-sense RNA molecules that have the first RNA sequence tag on their 3'-termini (from step (6) of the first round), the second-round first-strand cDNA synthesis primer, and an RNA-dependent DNA polymerase under conditions and for sufficient time wherein second-round first strand cDNA molecules are synthesized;

(8b) incubating the solution from step (7b) containing the second-round first-strand cDNA molecules, plus the second-round second-strand cDNA synthesis primer and the DNA-template-specific DNA polymerase, under conditions and for sufficient time wherein double-stranded cDNA molecules that contain a double-stranded RNA polymerase promoter are synthesized;

(9b) incubating the solution from step (8b) containing double-stranded cDNA molecules, plus the second RNA polymerase, under conditions and for sufficient time wherein multiple copies of sense RNA molecules are synthesized, each of which exhibits a sequence that is substantially identical to an RNA molecule of interest in the sample, and each of which has a second RNA sequence tag joined to its 5'-terminus. Thus, in this embodiment, the second round of amplification uses a second anti-sense promoter primer to synthesize sense RNA molecules that have a RNA sequence tag joined to their 5'-termini.

Another embodiment for synthesizing multiple copies of anti-sense RNA molecules that exhibit sequences that are substantially complementary to the RNA molecules of interest in a sample, each of which anti-sense RNA molecules has an RNA sequence tag that exhibits a desired arbitrary sequence joined to its 3'-terminus, is a method comprising the steps of:

(1) providing:
- a sample containing one or more RNA molecules of interest;
- at least one RNA-dependent DNA polymerase (e.g., AMV reverse transcriptase, or MMLV reverse transcriptase, or a mixture thereof);
- a terminal tagging oligoribonucleotide comprising ribonucleotides (rTTO), which terminal tagging oligoribonucleotide comprises or consists of a 5'-portion and 3'-portion; wherein the 5'-portion comprises or consists of (a) a segment that exhibits a sense promoter sequence for a double-stranded RNA polymerase promoter, (b) optionally, a segment that is 3'- of the sense promoter sequence that exhibits sequence which, when present in double-stranded DNA, can be cleaved by a restriction endonuclease (preferably a rare cutter restriction endonuclease; e.g., Not I or Asc I), and (c) optionally, one or more segments 5'- of or 3'- of the sense promoter sequence; and wherein the 3'-portion comprises or consists of at least three random nucleotides (e.g., 3 to 8 random nucleotides; e.g., 7 random nucleotides), of which the 3'-terminal nucleotide is blocked so that it is not capable of being extended by a DNA polymerase;
- a second-strand cDNA synthesis primer, comprising or consisting of an oligodeoxyribonucleotide that exhibits a sequence that is identical to at least the 5'-portion of the sequence exhibited by the rTTO and that is capable of annealing to the DNA sequence tag that is joined to the 3'-termini of the first-strand cDNA molecules in step (4), wherein, upon its extension in step (5), the second-strand cDNA synthesized exhibits the sense promoter sequence for the double-stranded RNA polymerase recognized by the RNA polymerase;
- optionally, a DNA-template-specific DNA polymerase (e.g., MMLV reverse transcriptase, AMV reverse transcriptase or FailSafe™ DNA polymerase);
- a DNA ligase (e.g., T4 DNA ligase); and
- an RNA polymerase (e.g., a T7-type RNA polymerase; e.g., T7, T3 or SP6 RNA polymerase) that is capable of synthesizing RNA using a DNA template that is joined to a double-stranded RNA polymerase promoter wherein the 3'-terminus of the template strand exhibits a the sense promoter sequence exhibited by the 5'-portion of the second-strand cDNA synthesis primer;

(2) incubating a solution containing the sample with the one or more RNA molecules of interest, plus at least one of the at least one RNA-dependent DNA polymerases, under conditions and for sufficient time wherein first-strand cDNA molecules that are complementary to the RNA molecules of interest are synthesized;

(3) incubating the solution from step (2) under conditions and for sufficient time wherein RNA that is annealed to DNA and single-stranded RNA are degraded (e.g., in the presence of RNase H and a single-strand-specific RNase (e.g., RNase I));

(4) incubating the solution from step (3) containing the first-strand cDNA molecules, plus the terminal tagging oligoribonucleotide and at least one of the at least one RNA-dependent DNA polymerases under conditions and for sufficient time wherein the terminal tagging oligoribonucleotide anneals to the first-strand cDNA molecules and the 3'-termini of the first-strand cDNA molecules are extended using the terminal tagging oligoribonucleotide as a template, wherein first-strand cDNA molecules that have the DNA sequence tag joined to their 3'-termini are synthesized, and then, optionally, incubating the solution under conditions and for sufficient time wherein RNA that is annealed to DNA and single-stranded RNA are degraded (e.g., in the presence of RNase H and a single-strand-specific RNase (e.g., RNase I));

(5) incubating the solution from step (4) containing the first-strand cDNA molecules that have the DNA sequence tag joined to their 3'-termini, plus the second-strand cDNA synthesis primer and, either, at least one of the at least one RNA-dependent DNA polymerases, or the DNA-template-specific DNA polymerase, under conditions and for sufficient time wherein double-stranded cDNA molecules are synthesized; and then, optionally, repairing the ends of the double-stranded cDNA molecules (e.g., by incubating in the presence of T4 DNA polymerase, dNTPs, T4 polynucleotide kinase, and ATP under conditions and for sufficient time wherein the ends of the double-stranded cDNA molecules are blunt and the 5'-termini are monophosphorylated; e.g., using the End-It™ DNA End Repair Kit, EPICENTRE, Madison, Wis., USA);

(6) incubating the solution from step (5) containing the double-stranded cDNA molecules, plus the DNA ligase under conditions and for sufficient time wherein the double-stranded cDNA molecules are self-ligated to form circular double-stranded cDNA molecules; and then, optionally, incubating the circular double-stranded cDNA molecules in a solution with the rare cutter restriction endonuclease under conditions and for sufficient time wherein the circular double-stranded cDNA molecules are cleaved and linear double-stranded cDNA molecules are generated; and (7) incubating the solution from step (6) containing circular or the linear double-stranded cDNA molecules, plus the RNA polymerase, under conditions and for sufficient time wherein multiple copies of anti-sense RNA molecules are synthesized, each of which, exhibits a sequence that is substantially complementary to one of the one or more RNA molecules of interest in the sample, and has an RNA sequence tag joined to its 3'-terminus.

Still another embodiment for synthesizing multiple copies of anti-sense RNA molecules that exhibit sequences that are substantially complementary to the RNA molecules of interest in a sample, each of which anti-sense RNA molecules has an RNA sequence tag that exhibits a desired arbitrary sequence joined to its 3'-terminus, is a method comprising the steps of:

(1) providing:
- a sample containing one or more RNA molecules of interest;
- at least one RNA-dependent DNA polymerase (e.g., AMV reverse transcriptase, or MMLV reverse transcriptase, or a mixture thereof);
- a terminal tagging oligoribonucleotide comprising ribonucleotides (rTTO), which terminal tagging oligoribonucleotide comprises or consists of a 5'-portion and 3'-portion, wherein the 5'-portion exhibits a sequence that is complementary to the sequence of the DNA sequence tag that it is desired to join to the 3'-termini of first-strand cDNA molecules, and wherein the 3'-portion comprises or consists of at least three random nucleotides (e.g., 3 to 8 random nucleotides; e.g., 7 random nucleotides), of which the 3'-terminal nucleotide is blocked so that it is not capable of being extended by a DNA polymerase;
- a second-strand cDNA synthesis primer, comprising or consisting of an oligodeoxyribonucleotide that consists of a 5'-portion and a 3'-portion, wherein the 5'-portion exhibits a sense promoter sequence for a double-stranded RNA polymerase promoter, and the 3'-portion has a 3'-hydroxyl group and exhibits a sequence that is complementary to the DNA sequence tag that is desired to be joined to the 3'-termini of the first-strand cDNA molecules;

optionally, a DNA-template-specific DNA polymerase (e.g., AMV reverse transcriptase or FailSafe™ DNA polymerase);

a DNA ligase (e.g., T4 DNA ligase); and an RNA polymerase (e.g., a T7-type RNA polymerase; e.g., T7, T3 or SP6 RNA polymerase) that is capable of synthesizing RNA using a DNA template that is joined to a double-stranded RNA polymerase promoter wherein the 3'-terminus of the template strand exhibits a the sense promoter sequence exhibited by the 5'-portion of the second-strand cDNA synthesis primer;

(2) incubating a solution containing the sample with the one or more RNA molecules of interest, plus at least one of the at least one RNA-dependent DNA polymerases, under conditions and for sufficient time wherein first-strand cDNA molecules that are complementary to the RNA molecules of interest are synthesized;

(3) incubating the solution from step (2) under conditions and for sufficient time wherein RNA that is annealed to DNA and single-stranded RNA are degraded (e.g., in the presence of RNase H and a single-strand-specific RNase (e.g., RNase I));

(4) incubating the solution from step (3) containing the first-strand cDNA molecules, plus the terminal tagging oligoribonucleotide and at least one of the at least one RNA-dependent DNA polymerases under conditions and for sufficient time wherein the terminal tagging oligoribonucleotide anneals to the first-strand cDNA molecules and the 3'-termini of the first-strand cDNA molecules are extended using the terminal tagging oligoribonucleotide as a template, wherein first-strand cDNA molecules that have the DNA sequence tag joined to their 3'-termini are synthesized, and then, optionally, incubating the solution under conditions and for sufficient time wherein RNA that is annealed to DNA and single-stranded RNA are degraded (e.g., in the presence of RNase H and a single-strand-specific RNase (e.g., RNase J));

(5) incubating the solution from step (4) containing the first-strand cDNA molecules that have the DNA sequence tag joined to their 3'-termini, plus the second-strand cDNA synthesis primer and, either, at least one of the at least one RNA-dependent DNA polymerases, or the DNA-template-specific DNA polymerase, under conditions and for sufficient time wherein double-stranded cDNA molecules that contain a double-stranded RNA polymerase promoter that is recognized by the RNA polymerase are synthesized; and then, optionally, repairing the ends of the double-stranded cDNA molecules (e.g., by incubating in the presence of T4 DNA polymerase, dNTPs, T4 polynucleotide kinase, and ATP under conditions and for sufficient time wherein the ends of the double-stranded cDNA molecules are blunt and the 5'-termini are monophosphorylated; e.g., using the End-It™ DNA End Repair Kit, EPICENTRE, Madison, Wis., USA);

(6) incubating the solution from step (5) containing the double-stranded cDNA molecules, plus the DNA ligase under conditions and for sufficient time wherein the double-stranded cDNA molecules are self-ligated to form circular double-stranded cDNA molecules; and then, optionally, incubating the circular double-stranded cDNA molecules under conditions and for sufficient time wherein the circular double-stranded cDNA molecules are cleaved (e.g., using a "rare cutter" restriction endonuclease; e.g., Not I or Asc I) at a "rare cutter" site that is precisely located within the arbitrary sequence of DNA sequence tag; e.g., by placing the sequence for the "rare cutter" site at the 5'-end of the rTTO, or in the 5'-portion of the second-strand cDNA synthesis primer at a site that is 3'- of the sense promoter sequence), wherein the strand that exhibits the sense promoter sequence is cleaved at a site that is 3'- of the sense promoter sequence and the complementary strand is cleaved at a site that is 5'- of the anti-sense promoter sequence, and linear double-stranded cDNA molecules are generated; and (7) incubating the solution from step (6) containing circular or the linear double-stranded cDNA molecules, plus the RNA polymerase, under conditions and for sufficient time wherein multiple copies of anti-sense RNA molecules are synthesized, each of which, exhibits a sequence that is substantially complementary to one of the one or more RNA molecules of interest in the sample, and has an RNA sequence tag joined to its 3'-terminus.

Embodiments of this method in which step (4) comprises the sub-step of contacting the solution under conditions and for sufficient time wherein RNA that is annealed to DNA and single-stranded RNA are degraded are preferred. However, in some embodiments (e.g., wherein the RNA-dependent DNA polymerase is inactivated (e.g., by heating to 95 degrees centigrade for approximately 3-10 minutes and a DNA-template-specific DNA polymerase that does not have reverse transcriptase activity is used in step (5)), step (4) may comprise, but need not comprise, the sub-step of contacting the solution under conditions and for sufficient time wherein RNA that is annealed to DNA and single-stranded RNA are degraded.

Preferred embodiments of the various methods for synthesizing anti-sense RNA molecules include a step after synthesis of the first-strand cDNA molecules and/or after synthesis of first-strand cDNA molecules that have a DNA sequence tag joined to their 3'-termini comprising: incubating the solution under conditions and for sufficient time wherein RNA that is annealed to DNA and single-stranded RNA are degraded (e.g., in steps (3) and step (4) of the method immediately above). However, in some embodiments (e.g., without limitation, wherein the RNA-dependent DNA polymerase used in the immediately-prior step is inactivated, e.g., by heating to 95 degrees centigrade for approximately 3-10 minutes; or wherein RNA does not interfere; or wherein the RNA is removed from the solution by purification), one or both of the steps of the method comprising degrading the RNA RNA may be, but need not be, omitted from the method.

Those with knowledge in the art will also understand that, although the applicants have emphasized use of the methods described herein to tag cDNA prepared from RNA molecules of interest in a sample, the methods are also applicable to tag DNA from any other source, and to generate RNA molecules therefrom, and the invention includes embodiments therefor. Thus, the invention comprises use of any of the methods disclosed herein to join a DNA sequence tag to single-stranded DNA, and to make tagged double-stranded DNA from any DNA from any source (e.g., without limitation, genomic DNA, mitochondrial DNA, chloroplast DNA, other organellar DNA, viral DNA, or even DNA synthesized using nucleic acid polymerases or modifying enzymes, or chemically synthesized using a DNA synthesizer). In some embodiments, if the DNA to be tagged is double-stranded, it is denatured to make it single-stranded for use in the method. In some embodiments, it is fragmented to a smaller size for use in the method.

Thus, one embodiment of the present invention is a method for joining a DNA sequence tag to the 3'-terminus of a DNA molecule, the method comprising:

(a) providing:
the DNA molecule;
an RNA-dependent DNA polymerase; and
a terminal tagging oligoribonucleotide comprising or consisting of a 5'-portion and 3'-portion, wherein the 5'-portion exhibits a sequence that is complementary to the sequence of the DNA sequence tag that it is desired to join to the 3'-terminus of the DNA molecule, and the 3'-portion comprises or consists of at least three random nucleotides (e.g., 3 to 8 random nucleotides; e.g., 7 random nucleotides), of which, the 3'-terminal nucleotide is not capable of being extended by a DNA polymerase;

(b) incubating the DNA molecule with the terminal tagging oligoribonucleotide under conditions and for sufficient time wherein the terminal tagging oligoribonucleotide anneals to the DNA molecule; and (c) contacting the DNA molecule to which the terminal tagging oligoribonucleotide is annealed with the RNA-dependent DNA polymerase in a reaction mixture and under conditions and for sufficient time wherein the 3'-termini of the DNA molecule is extended using the terminal tagging oligoribonucleotide as a template and a DNA molecule that has the DNA sequence tag joined to its 3'-terminus is synthesized.

In some embodiments of the method for joining a DNA sequence tag to the 3'-terminus of a DNA molecule, the 5'-portion of the terminal tagging oligoribonucleotide does not exhibit a proto-promoter sequence.

The DNA molecule provided in step (a) of this method can be derived from any DNA molecule of any type. If the DNA molecule is circular, it should be cleaved to generate a single-stranded DNA molecule for use in the method. If the DNA molecule is double-stranded, it should be denatured prior to being provided for the method. The DNA molecule also should have a 3'-hydroxyl group or treated with a DNA modifying enzyme that generates a 3'-hydroxyl group prior to it being provided for the method.

In some embodiments, the method for joining a DNA sequence tag to the 3'-terminus of the DNA molecule additionally comprises one or more of the following steps:

(d) inactivating the RNA-dependent DNA polymerase;
(e) incubating the reaction mixture with RNase H under conditions and for sufficient time wherein RNA that is annealed to DNA is digested;
(f) incubating the reaction mixture with a single-strand-specific RNase under conditions and for sufficient time wherein single-stranded RNA is digested;
(g) inactivating the RNase H; or
(h) inactivating the single-strand-specific RNase.

In some embodiments of any of the methods or compositions of the invention, modified deoxyribonucleotides are used in embodiments that comprise synthesis using a DNA polymerase or modified ribonucleotides are used in embodiments that comprise synthesis using an RNA polymerase. For example, without limitation, in some embodiments, nucleotides that comprise a nucleic acid base that is substituted with a group comprising or consisting of a 5-allyamino, a biotin, a visible, fluorescent, luminescent or chemiluminescent dye, or another detectable group or moiety, is used and the labeled nucleic acid is detected (e.g., when the labeled DNA (e.g., cDNA) or labeled RNA is used as target for hybridization to probes on arrays or microarrays). Also, in some embodiments, the nucleotides comprise modified internucleoside linkages, such as, phosphorothioate, phosphorodithioate, phosphoroselenate, orphosphorodiselenate linkages; which provide resistance to some nucleases.

The present invention further provides kits for carrying out any of the methods described herein. In some embodiments, the kits comprise one or more reagents necessary, sufficient, or useful for carrying out one or more or all of the steps of the methods described herein. Kit may include one or more packages containing the reagents, including containers (e.g., tubes, vials, etc.) housing individual reagents alone or together in the appropriate storage solutions. Kits may further comprise positive and negative control reagents, instructs for use, software, or other desired components.

One preferred embodiment of the invention is a kit for synthesizing first-strand cDNA molecules that have a DNA sequence tag joined to their 3'-termini, the kit comprising:

an terminal tagging oligoribonucleotide comprising ribonucleotides (rTTO), which terminal tagging oligoribonucleotide comprises or consists of a 5'-portion and 3'-portion, wherein the 5'-portion exhibits a sequence that is complementary to the sequence of the DNA sequence tag that it is desired to join to the 3'-termini of first-strand cDNA molecules, and wherein the 3'-portion comprises or consists of at least three random nucleotides (e.g., 3 to 8 random nucleotides; e.g., 7 random nucleotides), of which the 3'-terminal nucleotide is blocked so that it is not capable of being extended by a DNA polymerase;
an RNA-dependent DNA polymerase; and
instructions for performing the method.

In some preferred embodiments, the 5'-portion of the terminal tagging oligoribonucleotide in the kit does not exhibit a proto-promoter sequence.

In some preferred embodiments, the kit additionally comprises an oligoribonucleotide first-strand cDNA synthesis primer.

In some preferred embodiments, the kit additionally comprises:
RNase H (e.g., E. coli RNase H); and
a single-strand-specific RNase (e.g., E. coli RNase I).

In some preferred embodiments, the kit additionally comprises:
a second-strand cDNA synthesis primer comprising a first PCR primer;
a second PCR primer.

In some preferred embodiments, the kit additionally comprises:
a DNA-template-specific DNA polymerase comprising a thermostable DNA polymerase.

In some preferred embodiments, the kit additionally comprises:
(h) poly(A) polymerase.

In some embodiments, the present invention provides methods for reducing or avoiding background due to tagging of one or more primers in a process comprising synthesizing one or more first DNA molecules by extending one or more primers with a first DNA polymerase using one or more nucleic acid molecules as templates, and then tagging said one or more first DNA molecules by extension of said one or more first DNA molecules using a second nucleic acid polymerase, said method comprising: a) providing: a sample containing one or more nucleic acid molecules; one or more primers, each of which is composed entirely of ribonucleotides, and wherein at least one of said one or more primers is complementary to at least one of said one or more nucleic acid molecules (e.g., an oligo(U)n primer and/or a random-sequence oligoribonucleotide, and/or one or more oligoribonucleotides, each of which exhibits a sequence that is complementary to at least one nucleic acid molecule); a first DNA polymerase that is capable of synthesizing DNA by extension of a primer that is annealed to a nucleic acid template (e.g., without limitation, an RNA-dependent DNA and/or DNA-dependent polymerase; e.g., AMV reverse transcriptase, MMLV reverse transcriptase, T4 DNA polymerase, Taq DNA polymerase); a second nucleic acid polymerase composed of either a template-dependent DNA polymerase (e.g., AMV reverse transcriptase, MMLV reverse transcriptase, T4 DNA polymerase, Taq DNA polymerase) or a template-independent DNA polymerase (terminal transferase (TdT or terminal deoxynucleotidyl transferase)); and b) incubating a solution containing the one or more nucleic acid molecules, plus the one or more primers and the first DNA polymerase, under conditions and for sufficient time wherein the one or more primers anneal to the one or more nucleic acid molecules and the first DNA polymerase extends the one or more primers, wherein one or more first DNA molecules are synthesized; c) incubating the solution from step (b) under conditions and for sufficient time wherein the one or more primers are degraded (e.g., by incubating in the presence of one or more ribonuclease enzymes (e.g., by incubating in the presence of E. coli RNase I and, optionally, also with E. coli RNase H), and then thermally inactivating the one or more ribonucleases, or by incubating with alkali and then neutralizing the solution); d) incubating the solution from step (c) with the second nucleic acid polymerase under conditions and for sufficient time wherein the one or more first DNA molecules are tagged with a DNA tag, wherein the solution does not contain the one or more primers which have been tagged.

In some embodiments, wherein the second nucleic acid polymerase is terminal transferase, the DNA tag with which the one or more first DNA molecules are tagged is a homopolymeric tail comprising a homodeoxyribonucleotide; or a homoribonucleotide (e.g., as described in U.S. Pat. No. 5,962,272; or in Schmidt, W M and Mueller, M W, Nucleic Acids Res., 27: e31, 1999; both of which are herein incorporated by reference). In particular embodiments, wherein the second nucleic acid polymerase is a template-dependent DNA polymerase, the DNA tag with which the one or more first DNA molecules are tagged exhibits an arbitrary sequence that in complementary to a nucleic acid template that is also present in the solution (e.g., an rTTO, as used in some embodiments of the present invention).

BRIEF DESCRIPTION OF THE FIGURES

The following figures form part of the present specification and are included as examples to further demonstrate certain aspects of the present invention. The invention may be better understood by reference to one or more of these figures in combination with the detailed description of specific embodiments presented herein, but are not intended to limit the invention.

FIG. 6—Schematic of an application of the method to join a DNA sequencing tag for use in NexGen sequencing with the Roche/454 DNA sequencer. The Roche/454 sequencing tag can be used as a priming site for NexGen sequencing of cDNA generated from a multiplicity of RNA molecules of interest (e.g., mRNA) from small samples comprising total RNA from about one cell to about ten thousand cells.

FIG. 7—Shows an agarose gel of sense RNA molecules synthesized in Example 1 using a terminal tagging method with first-strand cDNA synthesis primers and terminal tagging oligonucleotides composed of deoxyribonucleotides with no mini-column purification steps prior to the first round of IVT-amplification reaction.

FIG. 8—Shows an agarose gel of sense RNA molecules synthesized in Example 2 after two rounds of IVT amplification using first-strand cDNA synthesis primers and terminal tagging oligonucleotides composed of deoxyribonucleotides, with a mini-column purification step, either only after the first-strand cDNA synthesis step, or after both the first-strand cDNA synthesis step and the terminal tagging step, prior to the first round of IVT-amplification reaction.

FIG. 9—Shows an agarose gel of sense RNA molecules synthesized in Example 3 after one round of IVT amplification using first-strand cDNA synthesis primers composed of deoxyribonucleotides and terminal tagging oligoribonucleotides (rTTO), with one mini-column purification step after the terminal tagging step, prior to the first round of IVT-amplification reaction.

FIG. 10—Shows agarose gels of sense RNA molecules synthesized in Example 4 after one round of IVT amplification using first-strand cDNA synthesis primers composed of either deoxyribonucleotides or ribonucleotides, and terminal tagging oligonucleotides composed of either deoxyribonucleotides or ribonucleotides, with no mini-column purification step prior to the first round of IVT-amplification reaction.

FIG. 12A—Shows the reproducibility of technical replicates of targets generated from amplified sense RNA compared to unamplified RNA on gene expression arrays based on the experiments presented in Example 7. The $\log_2$ signal values obtained with microarray targets generated from independently amplified sense-RNA batches and unamplified total RNA were plotted. The high $r^2$ values (0.985 for sense RNA amplified targets, and 0.993 for unamplified targets proved the excellent reproducibility of the sense RNA amplification process.

DETAILED DESCRIPTION OF THE INVENTION

Figure 1:
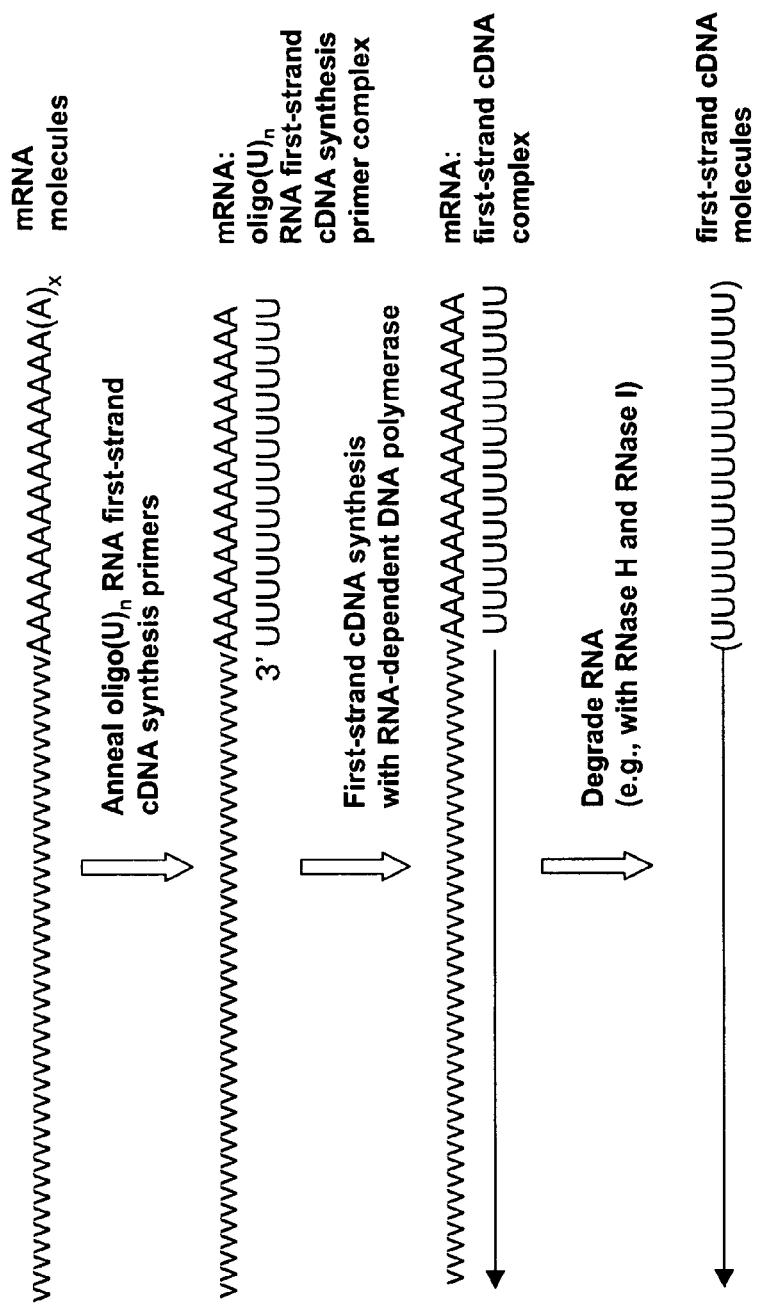
FIG. 1—Schematic of the steps of a method for synthesis of first-strand cDNA molecules using an RNA-dependent DNA polymerase for extension of an RNA first-strand cDNA synthesis primer consisting of oligo(U)$_n$ using RNA molecules of interest consisting of all polyadenylated eukaryotic mRNA molecules in a sample that contains total RNA. Note that the RNA first-strand cDNA synthesis primers, as well as the RNA molecules of interest, are removed by digestion with RNase H and single-strand-specific RNase, which in this example is RNase I. The composition of the RNA first-strand cDNA synthesis primers enables their easy and efficient removal following synthesis of the first-strand cDNA molecules, thereby avoiding "background" in subsequent steps of the method due to undesired joining of the DNA sequence tag to the 3'-termini of only the RNA first-strand cDNA synthesis primer molecules. In the embodiment shown, the oligo(U)-portion of the first-strand cDNA molecules remains annealed to the poly(A) tail of the RNA molecule of interest during the step of digestion with the RNase H and the RNase I, and therefore, is not digested. In some other embodiments, wherein the oligo(U)-portion of the first-strand cDNA molecules does not remain annealed to the poly(A) tail of the RNA molecule of interest during the step of digestion with the RNase H and the RNase I and is digested; this is the reason the oligo(U)-portion is in parenthesis in the schematic.
Figure 2:
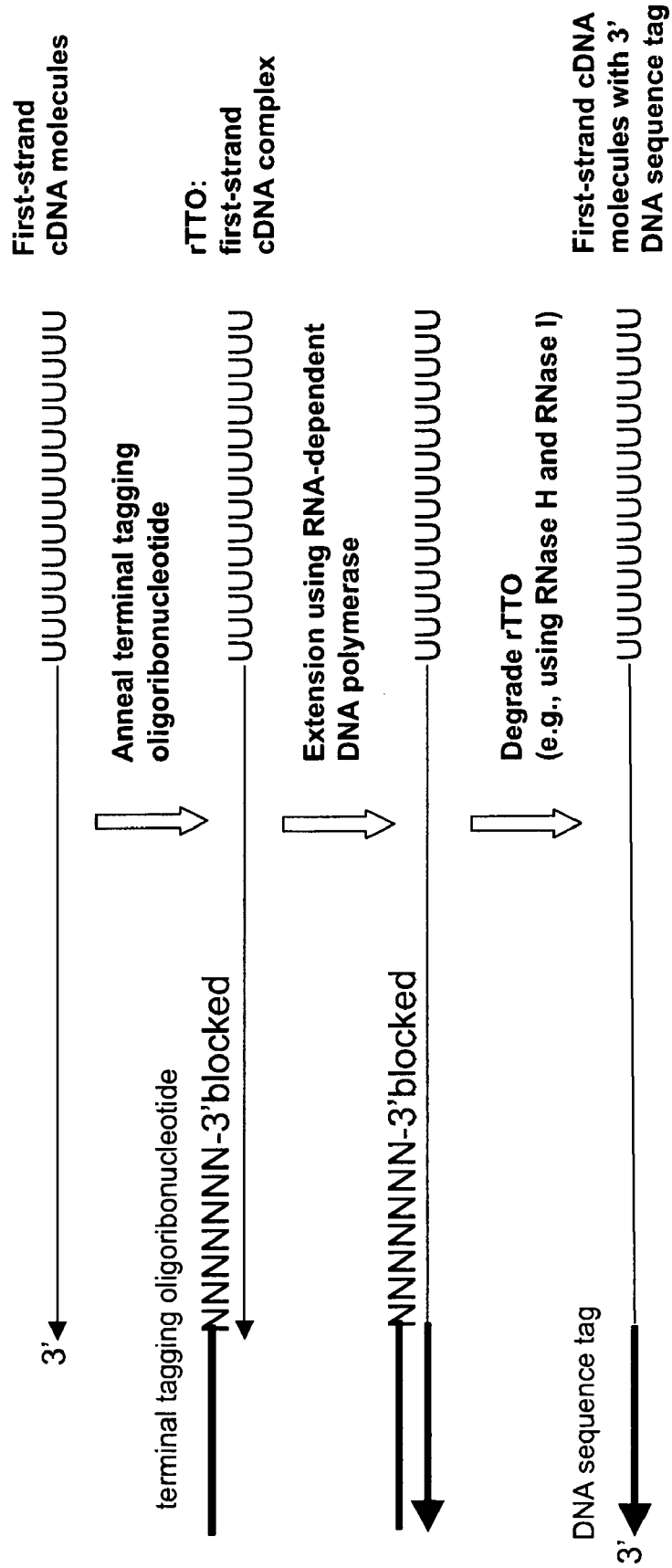
FIG. 2—Schematic of one preferred embodiment of step (D) of the method, which uses a terminal tagging oligoribonucleotide to join a DNA sequence tag to the 3'-termini of the first-strand cDNA molecules. Note that, in this embodiment, the terminal tagging oligoribonucleotide consists of only ribonucleotides, with the exception of the blocked 3-terminal nucleotide, and comprises a 5'-portion and a 3'-portion. In this particular preferred embodiment, the 5'-portion of the terminal tagging oligoribonucleotide exhibits a sequence that is complementary to the sequence of a desired arbitrary DNA sequence tag that is added to the 3'-termini of the first-strand cDNA molecules, and the 3'-portion of the terminal tagging oligoribonucleotide exhibits a random sequence of seven nucleotides, of which, the 3'-terminal nucleotide is blocked so that it is not capable of being extended by the RNA-dependent DNA polymerase. The ribonucleotide composition of the terminal tagging oligoribonucleotide enables its easy and efficient removal, and its blocked 3'-terminal nucleotide prevents it from serving as a primer for synthesis of DNA using the first-strand cDNA molecules as templates. Thus, when the 3'-portion of the terminal tagging oligoribonucleotide anneals to the 3'-terminal portion of a complementary first-strand cDNA molecule, the 5'-portion of the terminal tagging oligoribonucleotide serves as a template for extension of the 3'-terminus of the first-strand cDNA molecule by the RNA-dependent DNA polymerase.
Figure 3:
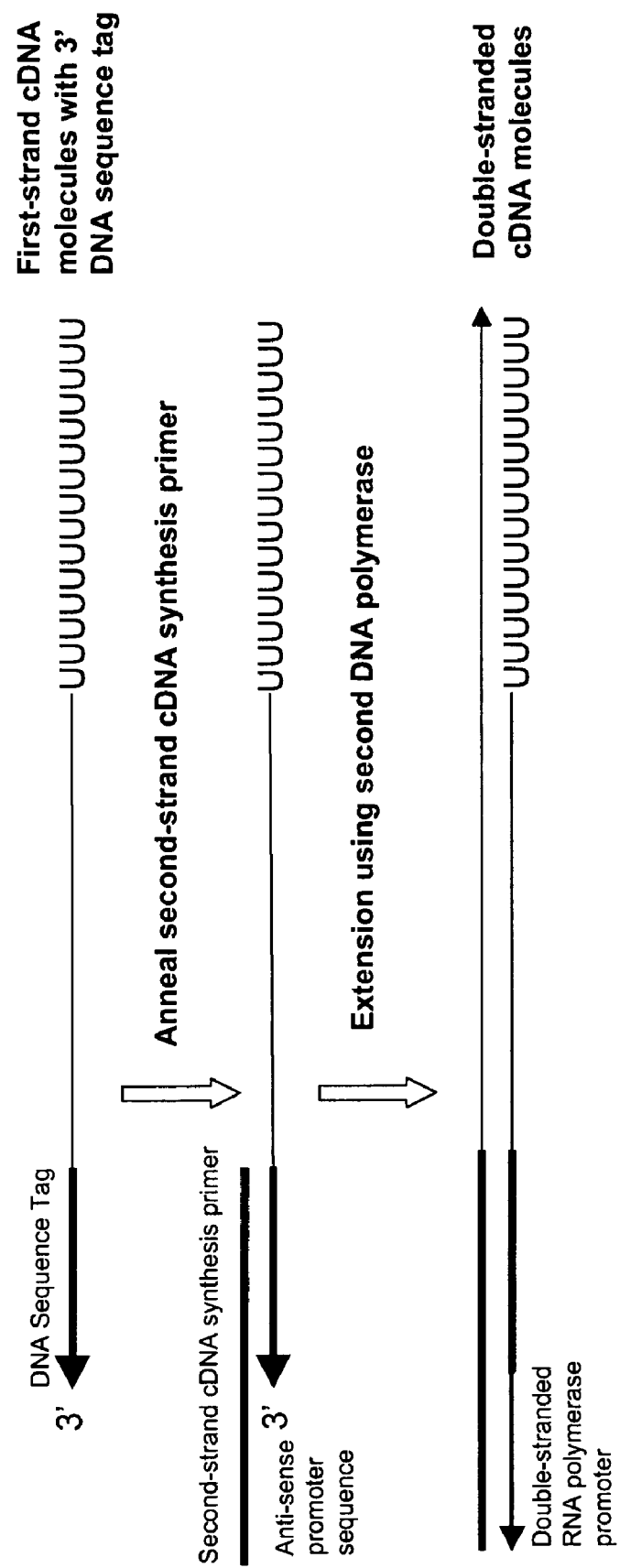
FIG. 3—Schematic of one preferred embodiment of step (E) of the method, which uses a second-strand cDNA synthesis primer consisting entirely of deoxyribonucleotides, and a DNA-template-specific DNA polymerase for synthesis of double-stranded cDNA molecules that contain a functional double-stranded RNA polymerase promoter (which are then contacted with the RNA polymerase that recognizes the promoter to synthesize sense RNA molecules that exhibit substantially the same sequences as the RNA molecule of interest in the sample, each of which has an RNA sequence tag joined to its 5'-terminus). Note that, after annealing the second-strand cDNA synthesis primer to the first-strand cDNA molecules, the first-strand cDNA molecules are made double-stranded and the double-stranded promoter is functionally joined thereto by the DNA-template-specific DNA polymerase extending the 3'-termini of both the second-strand cDNA synthesis primer and the first-strand cDNA molecules that have the DNA sequence tag on their 3'-termini.
Figure 4:
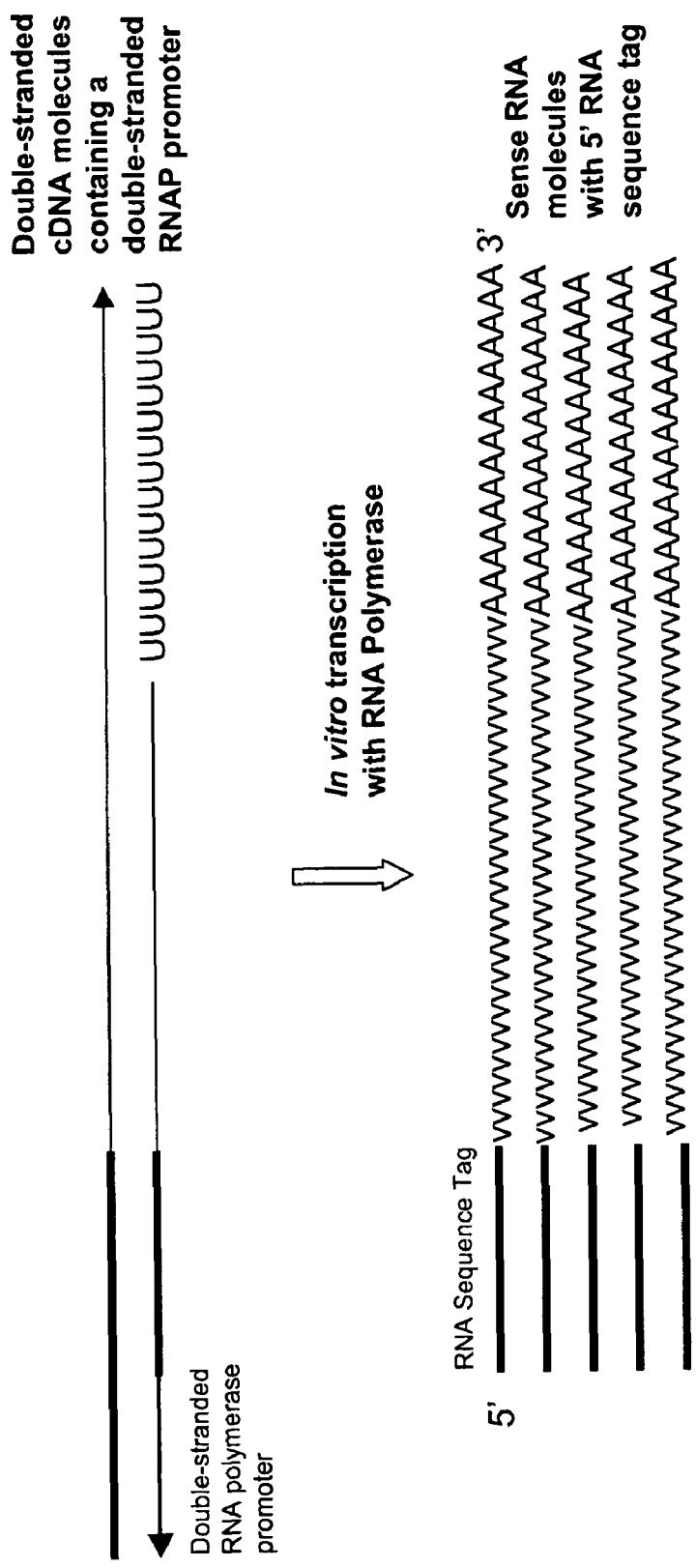
FIG. 4—Schematic of step (F) of the method, which uses the double-stranded cDNA molecules that contain the double-stranded RNA polymerase promoter, which were synthesized in step (E), as templates for in vitro transcription by an RNA polymerase that recognizes and binds to the RNA polymerase promoter. Note that multiple copies of sense RNA molecules that have an RNA sequence tag joined to their 5'-termini are synthesized.
Figure 5:
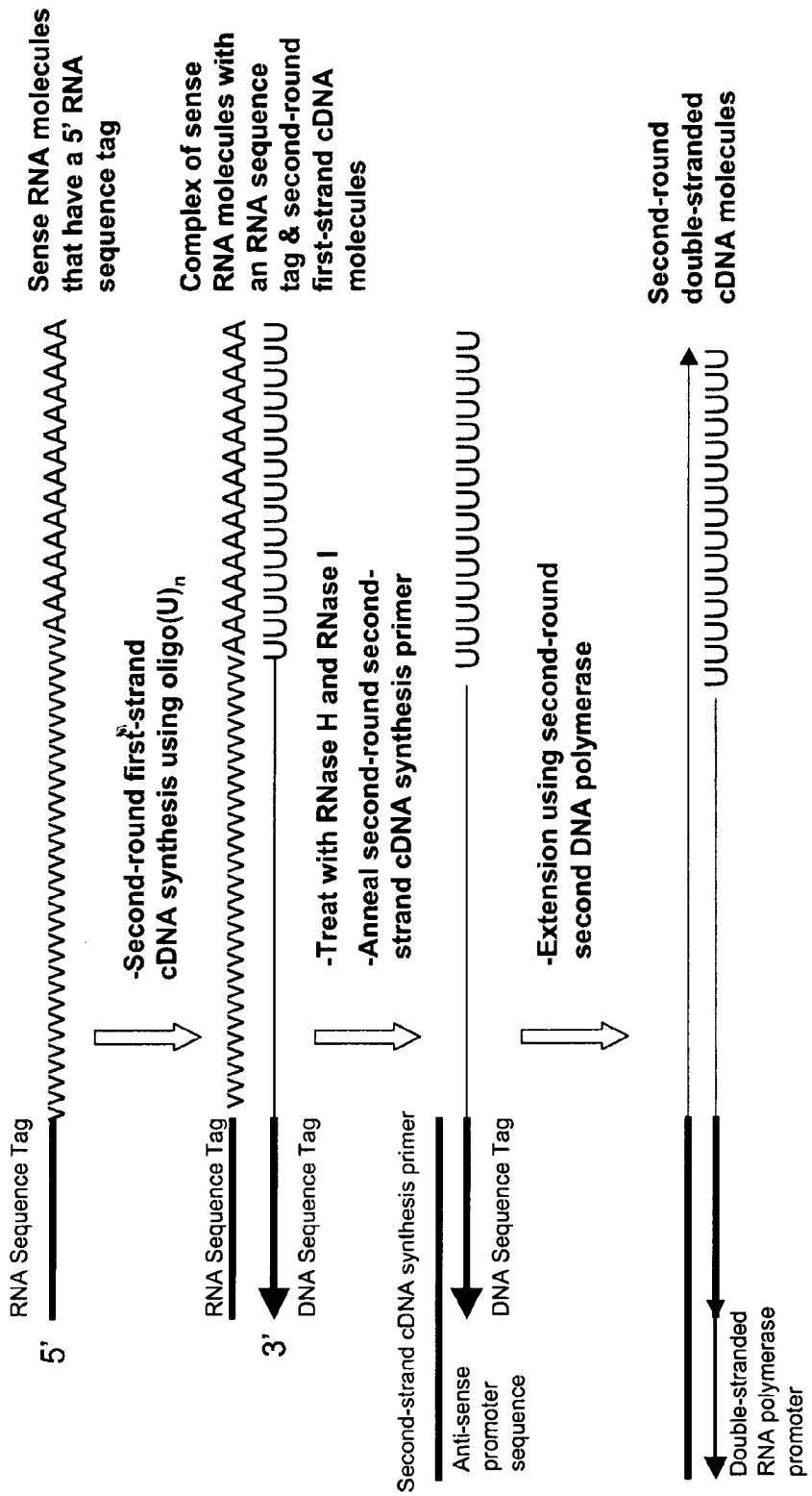
FIG. 5—Schematic of an abbreviated version of the steps (G) through (J) of one preferred embodiment of the method for a second round of amplification. The schematic is referred to as "abbreviated" because, for the sake of brevity, not all details of the steps are shown. This method uses the sense RNA molecules that have the RNA sequence tag joined to their 5'-termini from step (F) of the first-round to synthesize additional sense RNA molecules that have the RNA sequence tag joined to their 5'-termini. Note that, in the embodiment shown in the schematic, the sense RNA molecules that have the RNA sequence tag joined to their 5'-termini provided in step (G) have a poly(A) tail, because the oligo(U)-portion (or poly(U)-portion) of the first-strand cDNA molecules that had the DNA sequence tag joined to their 3'-termini in the first round remained annealed to the poly(A) tail and was not digested by the RNase H or the single-strand-specific RNase in step (C). The second-round first-strand cDNA synthesis primer shown in the schematic is identical to the first-strand cDNA synthesis primer used in the first round. If the oligo (U)-portion of the first-strand cDNA molecules is digested in step (C) and, therefore, the sense RNA molecules with the RNA sequence tag joined to their 5'-termini that are synthesized in step (F) lack a poly(A) tail, the method comprises additional steps prior to the steps shown in FIG. 5. Thus, in some embodiments, the method additionally comprises: contacting the sense RNA molecules that have the RNA sequence tag joined to their 5'-termini that are synthesized in step (F) of the first round of the method with poly(A) polymerase and ATP under conditions and for sufficient time wherein their 3'-termini are polyadenylated. Also, note that it is not necessary to provide an RNA-dependent DNA polymerase or a terminal tagging oligoribonucleotide to join the DNA sequence tag to the first-strand cDNA molecules in the embodiment shown in FIG. 5, since the sense RNA molecules already have the RNA sequence tag joined to their 5'-termini. Rather, the second-round first-strand cDNA molecules that have the DNA sequence tag joined to their 3'-termini are synthesized by extension of the second-round RNA first-strand cDNA synthesis primer by the second-round RNA-dependent DNA polymerase using the polyadenylated sense RNA molecules that have the RNA sequence tag joined to their 5'-termini as a template. In some embodiments, the second-round RNA-dependent DNA polymerase is inactivated (e.g., by heat treatment). Then, the second-round second-strand cDNA synthesis primer and the second-round DNA-template-specific DNA polymerase are used for synthesis of second-round double-strand cDNA molecules that contain a functional double-stranded RNA polymerase promoter. Then, in subsequent steps (not shown in the schematic) the second-round double-strand cDNA molecules are contacted with the RNA polymerase that recognizes the RNA polymerase promoter to synthesize additional sense RNA molecules that exhibit substantially the same sequences as the RNA molecule of interest and that have the RNA sequence tag joined to their 5'-termini. This same method for second-round amplification can be repeated for one or more additional rounds in order to further amplify the amount of sense RNA molecules that have the RNA sequence tag joined to their 5'-termini.
Figure 11:
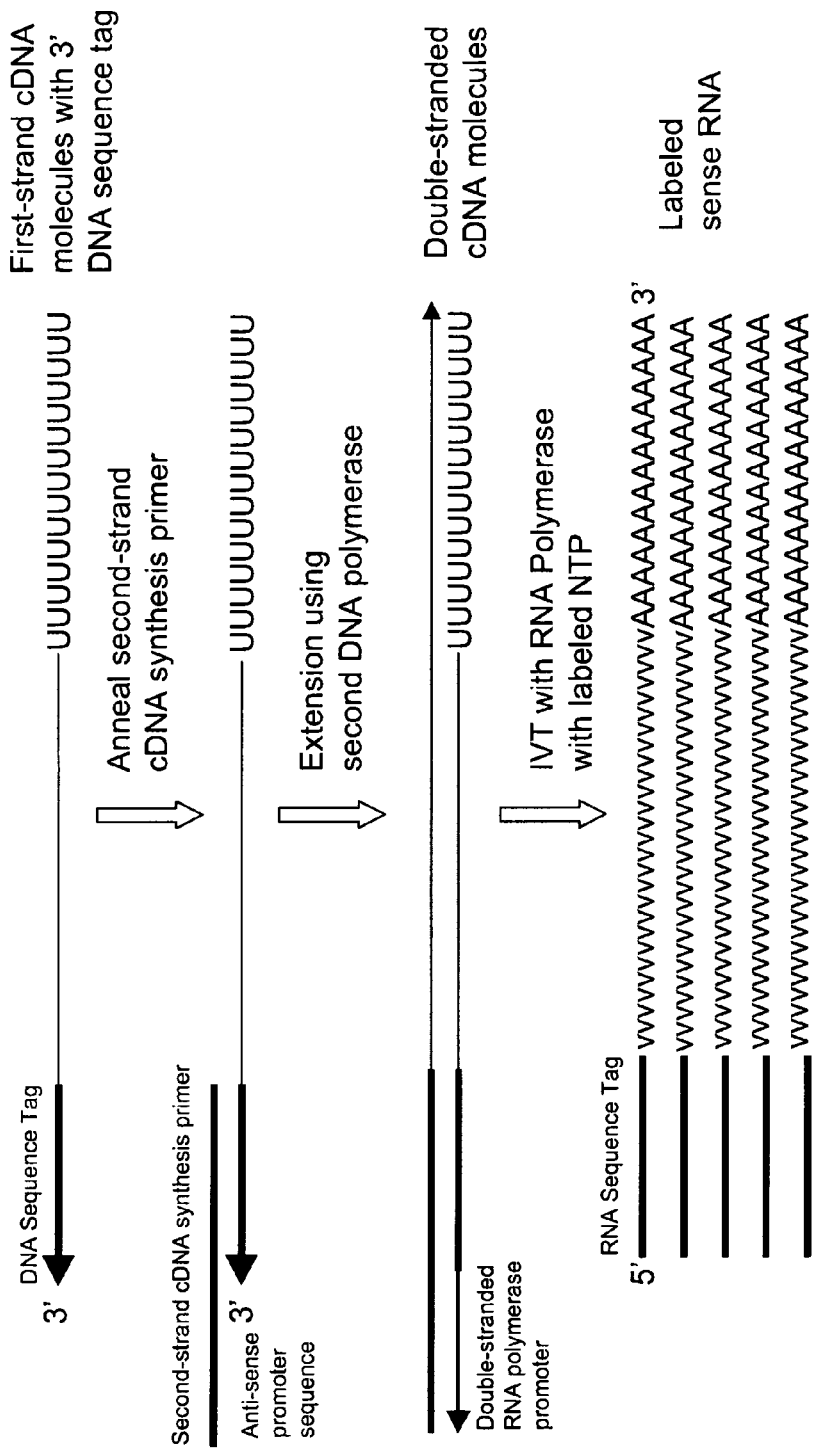
FIG. 11—Schematic of an application of the method to generate labeled sense RNA target for gene expression analysis on microarray chips spotted with anti-sense probes.

The following description provides exemplary method steps and reagents for practicing embodiments of the present invention. It should be understood that the invention is not limited to these illustrative embodiments.

Step (A): Providing Samples and Compositions for the Method

Providing a Sample Containing the RNA Molecules of Interest The Sample

A "sample" or a "biological sample" according to the present invention is used in its broadest sense. A sample is derived from a specimen from any source that contains or may contain an RNA molecule of interest, including any specimen that is collected from or is associated with a biological or environmental source, or which comprises or contains biological material, whether in whole or in part, and whether living or dead.

Samples or biological samples may be plant or animal, including human, fluid (e.g., blood or blood fractions, urine, saliva, sputum, cerebral spinal fluid, pleural fluid, milk, lymph, or semen), swabs (e.g., buccal or cervical swabs), solid (e.g., stool), microbial cultures (e.g., plate or liquid cultures of bacteria, fungi, parasites, protozoans, or viruses), or cells or tissue (e.g., fresh or paraffin-embedded tissue sections, hair follicles, mouse tail snips, leaves, or parts of human, animal, plant, microbial, viral, or other cells, tissues, organs or whole organisms, including subcellular fractions or cell extracts), as well as liquid and solid food and feed products and ingredients such as dairy items, vegetables, meat and meat by-products, and waste. Biological samples may be obtained from all of the various families of domestic plants or animals, as well as wild animals or plants.

In some embodiments, the sample comprises or consists of one or more whole cells from a specimen, such as from a fixed or paraffin-embedded formalin-fixed ("FFPE") section, or cells, such as human, animal, plant, or microbial cells grown in culture (e.g., human, animal, or plant cells obtained by fluorescent-activated cell sorting ("FACS"), or replica-plated bacteria or yeast).

Environmental samples include environmental material such as surface matter, soil, water, air, or industrial samples, as well as samples obtained from food and dairy processing instruments, apparatus, equipment, utensils, disposable and non-disposable items. These examples are not to be construed as limiting the sample types applicable to the present invention.

A sample on which the assay method of the invention is carried out can be a raw specimen of biological material, such as serum or other body fluid, tissue culture mixture or food material. More typically, the method is carried out on a sample that is a processed specimen, derived from a raw specimen by various treatments to remove materials that would interfere with detection of the RNA molecules of interest or an amplification product thereof. Methods for processing raw samples to obtain a sample more suitable for the assay methods of the invention are well known in the art.

Thus, a method of the present invention can be carried out on nucleic acid from a variety of sources, including unpurified nucleic acids, or nucleic acids purified using any appropriate method in the art, such as, but not limited to, various "spin" columns, cationic membranes and filters, or salt precipitation techniques, for which a wide variety of products are commercially available (e.g., RNA purification or extraction kits from EPICENTRE Biotechnologies, Madison, Wis., USA).

In some preferred embodiments, an inhibitor of RNase A-type enzymes is added to the sample prior to using the sample in the method of the invention. In some preferred embodiments, the inhibitor of RNase A-type enzymes is added to the raw biological sample prior to any processing or purification of nucleic acids. In other embodiments, the inhibitor of RNase A-type enzymes is added to a purified preparation of nucleic acid used in the method. Preferably, the inhibitor of RNase A-type enzymes does not inhibit the RNase H or single-strand-specific RNase used in the method. Without limitation, examples of inhibitors of RNase A-type enzymes that can be used include RNasin® placental ribonuclease inhibitor (Promega Corporation, Madison, Wis., USA) and ScriptGuard™ ribonuclease inhibitor (EPICENTRE Biotechnologies, Madison, Wis., USA), which do not inhibit *E. coli* RNase H or RNase I. In other embodiments, an antibody or an aptamer that binds to and inhibits an RNase that may be present in the sample is used. The antibody or aptamer that inhibits the RNase is made using methods that are known in the art. Some such RNase inhibitors are available from commercial sources.

RNA Molecules of Interest

The invention is not limited with respect to the type or source of the RNA molecules of interest and any RNA molecules of interest from any in vivo or in vitro source can be provided for use in the method. For example, but without limitation, the RNA molecules of interest can be selected from among one or more molecules consisting of: (i) eukaryotic mRNA; (ii) prokaryotic mRNA; (iii) RNA from an in vitro transcription reaction using an RNA polymerase; (iv) RNA from an in vitro replication reaction using a replicase; (v) RNA from an in vivo transcription reaction, wherein the RNA polymerase is expressed in a prokaryotic or eukaryotic cell that contains a DNA template that is functionally joined downstream of an RNA polymerase promoter that binds the RNA polymerase; (vi) RNA from an in vivo replication reaction using a replicase; (vii) RNA from an RNA amplification reaction; (viii) eukaryotic small nuclear (snRNA); (ix) micro RNA (miRNA); (x) eukaryotic viral RNA; (xi) eukaryotic ribosomal RNA; (xii) prokaryotic ribosomal RNA; (xiii) tRNA; (xiv) RNAi (e.g., siRNA); and (xv) non-coding RNA (ncRNA); and (xvi) any other naturally-occurring RNA molecules, whether of known or unknown function.

In some embodiments, the RNA molecules of interest are from an in vitro transcription reaction or an RNA amplification reaction that produces sense RNA (e.g., by amplification of RNA from one or a small number of cancer cells from a patient). In some preferred embodiments, the RNA molecules of interest are sense RNA molecules obtained by amplifying RNA molecules (e.g., mRNA and/or miRNA molecules) using a sense RNA amplification reaction, including, but not limited to, using the sense RNA amplification reaction method of the present invention. In some preferred embodiments, the RNA molecules of interest are prepared from a biological source by subtractive hybridization, digestion and RNA amplification, whereby the RNA molecules of interest are "condition-specific." By "condition-specific" RNA is meant an RNA sample that, relative to unfractionated condition-derived RNA, has a higher content of RNA that is preferentially present in the condition-specific cell compared to a cell without the condition, wherein a "condition" means a mode or state of being of the organism or cells from which the biological sample is derived (e.g., a cancer condition versus a non-cancerous condition, or a pathogen-infected condition versus an uninfected condition, or a first differentiated state versus a second differentiated state or versus an "undifferentiated" state such as an undifferentiated stem cell). For example, but without limitation, in some embodiments, the RNA molecules of interest comprise subtracted and amplified RNA, meaning RNA from a condition (e.g., a tumor cell condition) from which RNA that is also present in a similar sample that lacks the condition (e.g., a normal cell of the same type) has been removed by using a method for subtractive hybridization and digestion, and then the remaining RNA is amplified using an RNA amplification reaction. In some embodiments, the RNA molecules of interest are obtained using the subtractive hybridization and digestion methods described in U.S. Pat. No. 5,712,127; however, any method can be used for subtracting the RNA molecules that are in common between two or more samples and obtaining only the RNA molecules that are different between the samples. In some preferred embodiments, the RNA molecules of interest are sense RNA molecules obtained using the method of the present invention; however, any RNA amplification method (e.g., any sense RNA amplification method) can be used.

In some preferred embodiments, the one or more RNA molecules of interest that are provided in step (A) comprise one or more eukaryotic polyadenylated mRNA molecules (e.g., eukaryotic mRNA). The eukaryotic polyadenylated mRNA can be in a sample that also contains other RNA molecules that are not of interest, such as a sample comprising total RNA derived from one or more eukaryotic cells. In some preferred embodiments, the eukaryotic polyadenylated mRNA comprises substantially all of the mRNA molecules present in one or more eukaryotic cells. In other preferred embodiments, the one or more RNA molecules of interest in the sample comprise RNA molecules derived from one or more eukaryotic or prokaryotic cells, which RNA molecules are not polyadenylated. In some preferred embodiments, the RNA molecules of interest from the sample are not polyadenylated, but are polyadenylated prior to use, wherein the method additionally comprises the steps of: providing a poly(A) polymerase and ATP; and contacting the RNA molecules of interest from the sample with the poly(A) polymerase and ATP under conditions and for sufficient time wherein the 3'-termini of the RNA molecules from the sample are polyadenylated, thereby providing polyadenylated RNA molecules of interest. In some other preferred embodiments, the one or more RNA molecules of interest comprise RNA molecules that have an RNA sequence tag that is joined to their 3'-termini using the method described in U.S. Patent Application No. 20050153333 of Sooknanan, wherein the RNA sequence tag provides a site for annealing of the RNA first-strand cDNA synthesis primer for synthesis of first-strand cDNA molecules in step (B) of the method. In some preferred embodiments, the RNA molecules of interest which have been polyadenylated or to which an RNA sequence tag has been joined to their 3'-termini prior to use in the method are selected from the group consisting of: (i) prokaryotic mRNA; (ii) non-polyadenylated eukaryotic mRNA; (iii) snRNA; (iv) miRNA; (v) RNAi; (vi) siRNA; (vi) RNA synthesized in vitro using an RNA amplification reaction or method wherein cDNA obtained by reverse transcription of RNA molecules derived from one or more eukaryotic or prokaryotic cells is transcribed using an RNA polymerase; and (vii) ncRNA (e.g., polyadenylated or non-polyadenylated ncRNA).

An RNA molecule of interest can also have "complexing sequences" which are added during processes of some embodiments of the methods of the invention to facilitate joining of an RNA molecule of interest to another polynucleotide for a particular purpose. For example, a complexing sequence can provide a complementary sequence to which an oligonucleotide (e.g., a first-strand cDNA synthesis primer) used in the method can anneal or complex. A complexing sequence usually comprises a "tail" sequence that is added by means such as those discussed herein, including, but not limited to, polyadenylation of the RNA molecules using poly(A) polymerase and ATP. If a complexing sequence is added to the RNA molecules of interest, it is desirable that a complexing sequence is chosen that does not affect the specificity of the sense RNA molecule transcription products ultimately synthesized using the double-stranded cDNA which has a functional double-stranded RNA polymerase promoter as a template.

Any method known in the art can be used to prepare and provide a sample containing one or more RNA molecules that is enriched with respect to the proportion of a particular group or class of RNA molecules of interest. For example, the one or more RNA molecules of interest can be selected, separated, or enriched on the basis of any property, such as but not limited to, by size, charge, or the presence or absence of a particular group (e.g., presence or absence of a poly(A) tail, a 5'-cap nucleotide, 5'-triphosphate, a 5'-monophosphate, a 5'-diphosphate, a 5'-hydroxyl, e.g., by using an enzyme that modifies or digests or adds another molecule to the RNA with said group, e.g., tobacco acid pyrophosphatase, RNA-5'-polyphosphatase, RNA-5'-monophosphatase, T4 RNA ligase plus and RNA acceptor with a 3'-hydroxyl group, Xrn 1 5'-exoribonuclease, poly(A) polymerase).

In some embodiments, the one or more RNA molecules of interest comprise one or more entire RNA molecules, such as, one or all full-length mRNA molecules in a particular sample. In other embodiments, the RNA molecules of interest comprise only a portion of one or more RNA molecules.

Providing at Least One RNA-Dependent DNA Polymerase

The "RNA-dependent DNA polymerase" or "reverse transcriptase" provided in step (A) means a DNA polymerase that is capable of extending the 3'-end of a nucleic acid that is annealed to an RNA template to synthesize DNA that is complementary to said RNA template. An RNA-dependent DNA polymerase is used for synthesis of first-strand cDNA molecules in step (B) and for synthesis of first-strand cDNA molecules that have a DNA sequence tag joined to their 3'-termini in step (D). In general, the invention is not limited with respect to the RNA-dependent DNA polymerase or reverse transcriptase used so long as it functions for its intended purpose in the method.

In some preferred embodiments of the method comprising all or a subset of steps (A) through (F) or steps (A) through (K), any one of the "at least one RNA-dependent DNA polymerases" provided in step (A) is a retroviral reverse transcriptase or an RNase H-minus derivative of a retroviral reverse transcriptase. In some preferred embodiments, the RNA-dependent DNA polymerase provided in step (A) is selected from the group consisting of: AMV reverse transcriptase; an RNase H-minus derivative of AMV reverse transcriptase; MMLV reverse transcriptase; an RNase H-minus derivative of MMLV reverse transcriptase; HIV reverse transcriptase, another retroviral reverse transcriptase, Tth DNA polymerase; a Bst DNA polymerase that lacks 5'-to-3' exonuclease activity (e.g., IsoTherm™ DNA polymerase or rBst DNA polymerase large fragment, EPICENTRE Biotechnologies, Madison, Wis., USA); and a Bca DNA polymerase that lacks 5'-to-3' exonuclease activity (e.g., BcaBEST™ DNA polymerase, Takara Shuzo Co, Kyoto, Japan).

In some preferred embodiments, a mutant form of a reverse transcriptase, such as, an MMLV reverse transcriptase or AMV reverse transcriptase or HIV reverse transcriptase or another retroviral reverse transcriptase that lacks RNase H activity is used. In other preferred embodiments, the wild-type form of the enzyme, such as the wild-type form of MMLV reverse transcriptase or AMV reverse transcriptase, is used. With respect to the RNA-dependent DNA polymerase used to extend the 3'-termini of first-strand cDNA molecules that are annealed to the relatively short 3'-portion of the terminal tagging oligoribonucleotide (e.g., in preferred embodiments, consisting of about three to eight; e.g., preferably seven nucleotides), the RNA-dependent DNA polymerase is preferably not a thermostable DNA polymerase and is active at temperatures between about 15 degrees to about 37 degrees centigrade. In some preferred embodiments, the RNA-dependent DNA polymerase is AMV reverse transcriptase or MMLV reverse transcriptase. In some preferred embodiments, the RNA-dependent DNA polymerase used in step (D) is the same enzyme that is provided as the RNA-dependent DNA polymerase used in step (B). In one preferred embodiment, AMV reverse transcriptase is used as the RNA-dependent DNA polymerase in both step (B) and step (D). In some other embodiments, different enzymes are used for step (B) and step (D). For example, in one preferred embodiment, AMV reverse transcriptase is used as the RNA-dependent DNA polymerase in step (B) and another enzyme, such as MMLV reverse transcriptase is used as the RNA-dependent DNA polymerase in step (D). In some embodiments, the RNA-dependent DNA polymerase used in step (B) or step (D), or both, is a retroviral reverse transcriptase. In some embodiments, the retroviral reverse transcriptase is modified to have reduced RNase H activity. In some embodiments, the RNA-dependent DNA polymerase polymerase used in step (B) or step (D), or both, is the rBst DNA polymerase large fragment.

Providing a DNA-Template-Specific DNA Polymerase

As used herein, a "DNA-template-specific DNA polymerase" means a DNA polymerase that extends a primer that is annealed to a DNA template, which DNA polymerase may, but need not, have activity in extending a primer that is annealed to an RNA template. The DNA-template-specific DNA polymerase is used to synthesize double-stranded cDNA molecules by extension of the second-strand cDNA synthesis primers that are annealed to and use the first-strand cDNA molecules that have the DNA sequence tag joined to their 3'-termini as templates. A variety of DNA polymerases are known in the art which can be used for this purpose, and any suitable DNA polymerase that functions in the method can be used as the DNA-template-specific DNA polymerase.

In some preferred embodiments, the DNA-template-specific DNA polymerase is selected from among: (i) AMV reverse transcriptase; (ii) MMLV reverse transcriptase; (iii) rBst DNA polymerase large fragment (EPICENTRE Biotechnologies, Madison, Wis., USA); (iv) AmpliTherm™ DNA polymerase (EPICENTRE); (v) Pfu DNA polymerase (Stratagene, La Jolla, Calif.); exo-minus KOD DNA polymerase (Toyobo Company, Osaka, Japan); (vi) VENT® DNA polymerase (Kong et al., J. Biol. Chem. 268:1965-1975, 1993); (vii) exo-minus VENT® DNA polymerase (New England Biolabs, Massachusetts, USA); (viii) Klenow fragment of DNA polymerase I (Jacobsen et al., Eur. J. Biochem. 45:623-627, 1974); (ix) T5 DNA polymerase (Chatterjee et al., Gene 97:13-19, 1991); (x) modified (Sequenase™) T7 DNA polymerase (Tabor and Richardson, J. Biol. Chem. 262:15330-15333, 1987 and J. Biol. Chem. 264:6447-6458, 1989; U.S. Biochemicals, Cleveland, Ohio, USA); (xi) exo-minus T4 DNA polymerase; and (xii) BcaBEST™ DNA polymerase (Takara Shuzo Co., Kyoto, Japan). However, the DNA-template-specific DNA polymerase used in the method is not limited to these DNA polymerases.

Providing a Second-Strand cDNA Synthesis Primer

The second-strand cDNA synthesis primer consists of an oligodeoxyribonucleotide that has a 5'-portion and a 3'-portion, wherein the 5'-portion exhibits at least a portion of an anti-sense promoter sequence for a double-stranded RNA polymerase promoter, and the 3'-portion has a 3'-hydroxyl group and exhibits a sequence that is complementary to the DNA sequence tag that is joined to the 3'-termini of the first-strand cDNA molecules. The 3'-portion of the second-strand cDNA synthesis primer is identical to at least a portion of the sequence exhibited by the RNA sequence tag that is joined to the 5'-termini of the sense RNA molecules synthesized using the method.

In some preferred embodiments, the 5'-portion of the second-strand cDNA synthesis primer exhibits the complete anti-sense promoter sequence of an RNA polymerase promoter. In these embodiments, a complete double-stranded RNA polymerase promoter is obtained by extending the 3'-termini of the first-strand cDNA molecules that have the DNA sequence tag joined to their 3'-termini using the 5'-portion of the second-strand cDNA synthesis primers as a template, which occurs in step (E) of the method. In some of these embodiments, in addition to exhibiting the anti-sense promoter sequence for a double-stranded RNA polymerase promoter, the 5'-portion also exhibits other sequences 5'- of and/or 3'- of the anti-sense promoter sequence, which sequences can be used to accomplish any intended application in the method. For example, but without limitation, in some embodiments, the DNA sequence tag that is joined to the 3'-termini of the first-strand cDNA molecules in step (D) of the method is shorter than the RNA sequence tag that is joined to the 5'-termini of the sense RNA molecules synthesized in step (E); thus, in some embodiments, in addition to exhibiting the anti-sense promoter sequence for a double-stranded RNA polymerase promoter, the 5'-portion also exhibits a sequence 3'- of the anti-sense promoter sequence that is the same as that portion of the sequence exhibited by the RNA sequence tag for which there is no complementary sequence in the DNA sequence tag. Thus, in these embodiments, a portion of the sequence that is complementary to the RNA sequence tag that is joined to the sense RNA molecules synthesized in step (F) is joined to the 3'-termini of the first-strand cDNA molecules that have the DNA sequence tag joined to their 3'-termini by extension of their 3'-termini by the DNA-template-specific DNA polymerase in step (E), using the 5'-portion of the second-strand cDNA synthesis primer as a template. In some preferred embodiments, the sequence exhibited by the 5'-portion of the second-strand cDNA synthesis primer that is complementary to the RNA sequence tag joined to the 5'-termini of the sense RNA molecules synthesized in step (F) is a single specific sequence, and therefore the sequence exhibited by the RNA sequence tag is the same on all sense RNA molecules synthesized in step (F). In other embodiments, the 5'-portion of the second-strand cDNA synthesis primers exhibits a random sequence (e.g., a random sequence consisting of about four to about ten random nucleotides) that is complementary to an RNA sequence tag that is joined to the 5'-termini of the sense RNA molecules synthesized in step (F); thus, the sequence exhibited by the 5'-portion of almost every RNA sequence tag is different and unique for the sense RNA molecules synthesized from different double-stranded cDNA molecules that are synthesized in step (E) of the method. The use of second-strand cDNA synthesis primers that exhibit a random sequence in their 5'-portion permits quantification of sense RNA molecules transcribed by the RNA polymerase from specific double-stranded cDNA molecules that contain the double-stranded promoter (e.g., to determine the number of sense RNA molecules synthesized in step (F) from different double-stranded cDNA molecules used as a template).

In still other embodiments, the 5'-portion of the second-strand cDNA synthesis primer exhibits a sequence 5'- of the anti-sense promoter sequence for the RNA polymerase that is used to provide a PCR priming site at the 3'-end of the complementary first-strand cDNA molecules.

In still other embodiments, the 5'-portion of the second-strand cDNA synthesis primer exhibits an anti-sense promoter sequence for a second RNA polymerase promoter recognized by a second RNA polymerase, which anti-sense promoter sequence for the second RNA polymerase promoter is located in the second-strand cDNA synthesis primer 5'- of the anti-sense promoter sequence for the first RNA polymerase promoter.

The invention is not limited with respect to which sequences are exhibited 3'- of and/or 5'- of the anti-sense promoter sequence in the 5'-portion of the second-strand cDNA synthesis primers, so long as the desired or arbitrary sequence accomplishes an intended purpose.

The invention is also not limited with respect to the anti-sense promoter sequence exhibited in the 5'-portion of the second-strand cDNA synthesis primers, and can be any anti-sense promoter sequence for a double-stranded promoter that is specifically recognized by the RNA polymerase used for synthesis of the sense RNA molecules that have the RNA sequence tag joined to their 5'-termini in step (F) of the method. The length of the anti-sense promoter sequence in the second-strand cDNA synthesis primers will vary depending upon the promoter chosen. For example, in some preferred embodiments, a functional T7 RNA polymerase promoter can be only about 25 nucleotides in length, while some other promoter sequences require 50 or more nucleotides to provide a functional promoter. Examples of RNA polymerases and their promoters which can be used in the method are discussed in the next section and in other sections herein.

In some other preferred embodiments, the 5'-portion of the second-strand cDNA synthesis primer exhibits only a portion of the anti-sense promoter sequence of an RNA polymerase promoter, in which embodiments, the remaining portion of the anti-sense promoter sequence is exhibited by the immediately-contiguous 3'-portion of said second-strand cDNA synthesis primers; thus, in these embodiments, the sequence exhibited by the 3'-end portion of the DNA sequence tag, which DNA sequence tag is joined, at its 5'-terminus, to the 3'-termini of the first-strand cDNA molecules, exhibits a portion, but not all, of the sense promoter sequence. In these embodiments, a complete double-stranded RNA polymerase promoter is obtained by extending the 3'-termini of the first-strand cDNA molecules that have the DNA sequence tag joined to their 3'-termini using the 5'-portion of the second-strand cDNA synthesis primers as a template, which occurs in step (E) of the method. In some of these embodiments, in addition to exhibiting the anti-sense promoter sequence for the double-stranded RNA polymerase promoter, the 5'-portion also exhibits other sequences 5'- of the anti-sense promoter sequence, which sequences can be used to accomplish any intended application in the method (e.g., to improve binding of the RNA polymerase to the promoter in step (F) or for other purposes as discussed elsewhere herein).

Providing an RNA Polymerase

The methods of the invention can use any RNA polymerase for which a suitable RNA polymerase promoter is known or can be obtained. Preferred RNA polymerases of the invention are T7-type RNA polymerases and preferred RNA polymerase promoters comprise the respective RNA polymerase promoters for the specific T7-type RNA polymerase. In some preferred embodiments, the RNA polymerase provided in step (A) is T7 RNA polymerase and the RNA polymerase promoter is one recognized by T7 RNA polymerase. However, in other embodiments, other RNA polymerases and the RNA polymerase promoters they recognize are used. For example, in some embodiments the RNA polymerase provided is *E. coli* RNA polymerase. An example of a promoter that can be used with *E. coli* RNA polymerase is a promoter for a bacteriophage T5 gene that is transcribed by the *E. coli* host RNA polymerase.

Step (B): Synthesizing First-Strand cDNA Molecules

In some preferred embodiments of the method, first-strand cDNA molecules are synthesized by reverse transcription using an RNA-dependent DNA polymerase (or reverse transcriptase) and RNA molecules of interest comprising messenger RNA (mRNA) obtained from a biological sample as a template, which first-strand cDNA molecules are complementary to the mRNA. However, in some embodiments of the method, the term "first-strand cDNA molecules" refers to cDNA molecules synthesized by reverse transcription of any RNA molecules of interest, even if they are not mRNA molecules. Also, in some embodiments, the term "first-strand cDNA molecules" is used even if no second-strand cDNA molecules are synthesized; thus, the terms "first-strand cDNA" or "first-strand cDNA molecules" can be used even when the method results in synthesis of only single-stranded cDNA that is complementary to the RNA molecules of interest, such as in embodiments of the method that use an RNA polymerase that recognizes a single-stranded RNA polymerase promoter (e.g., N4 mini-vRNAP) or pseudopromoter and a single-stranded template.

In some preferred embodiments wherein the RNA molecules of interest comprise mRNA or one or more RNA molecules of interest that are polyadenylated (e.g., naturally occurring polyadenylated RNA molecules or RNA molecules that are polyadenylated in vitro using poly(A) polymerase and ATP), the RNA first-strand cDNA synthesis primer is selected from the group consisting of: (i) oligo$(U)_n$; (ii) oligo(U)nN, wherein "N" comprises a randomized 3'-terminal ribonucleotide or deoxyribonucleotide synthesized using an equal molar mixture of four ribonucleotides or deoxyribonucleotides having A, C, G, and T or U nucleic acid bases; (iii) oligo(U)nV, wherein "V" comprises a randomized anchor ribonucleotide or deoxyribonucleotide synthesized using an equal molar mixture of three ribonucleotides or deoxyribonucleotides having A, C, and G but not U or T, nucleic acid bases; (iv) an oligoribonucleotide random primer (e.g., a random hexamer) wherein the random primer is synthesized using an equal molar mixture of all four ribonucleotides (i.e., having A, C, G, and U nucleic acid bases) at every nucleotide position (e.g., so every possible hexamer sequence is present in the first-strand cDNA synthesis reaction); (v) an oligoribonucleotide semi-random primer, meaning an oligoribonucleotide wherein one, two or three consecutive nucleotides of the primer are random (i.e., synthesized using nucleotides with all four A, C, G, and U nucleic acid bases) at each of these nucleotide positions), but then at least one next nucleotide position in the primer is synthesized using only one, two or three, but not four, of the four A, C, G, and U ribonucleotides (e.g., semi-random hexamer primers comprising a mixture of all four A, C, G, and U ribonucleotides in the first, second, fourth, fifth and sixth positions, but only one, two, or three of the four A, C, G, and U ribonucleotides in the third position), wherein the number of sequences exhibited by the primers is reduced compared to random primers (e.g., if the third position of the hexamer is semi-random, the primers would exhibit only 3072, 2048, or 1024 sequences, respectively, if the hexamer is synthesized using three, two, or one of the A, C, G, and U ribonucleotides at the third position, compared to 4096 sequences exhibited for a random hexamer synthesized with all nucleotide positions being random nucleotides); and (vi) an oligoribonucleotide specific-sequence or defined-sequence primer, wherein the primer exhibits a sequence that is complementary to a sequence exhibited by a specific RNA molecule of interest. In some preferred embodiments, a mixture of two or more of the six types of RNA first-strand cDNA synthesis primers (i.e., of types (i) through (vi) immediately above) is used for synthesizing the first-strand cDNA molecules. For example, but without limitation, in some embodiments, a mixture of an oligo(U)n, an oligo(U)nN, or an oligo(U)nV primer and a random primer (e.g., a random hexamer oligoribonucleotide primer) is used for synthesis of first-strand cDNA molecules (e.g., using fragmented mRNA molecules of interest, e.g., from a formalin-fixed paraffin-embedded tissue section; or e.g., to achieve full coverage for gene expression analysis of expressed exons, wherein sense RNA molecules must be synthesized that exhibit all sequences exhibited by the RNA molecules of interest in an unbiased manner). The method is not limited only to use of an RNA first-strand cDNA synthesis primer of the above types (i) through (vi) so long as it is capable of priming synthesis of first-strand cDNA molecules to accomplish the intended purpose. For example, but without limitation, an RNA first-strand cDNA synthesis primer consisting of only oligo(U)n(dA), oligo(U)n(dC), or oligo(U)n(dG) can be used to synthesize first-strand cDNA molecules, wherein the nucleotide that is complementary to the anchor nucleotide is known for a particular mRNA molecule of interest. Still by way of example, a mixture of oligo(U)n(dA) and oligo(U)n(dG) could be used to make first-strand cDNA molecules in an embodiment wherein a particular motif in the RNA molecules of interest is known to include a 3'-terminal pyrimidine nucleotide next to the poly(A) tail.

In some preferred embodiments, oligo(U)n, or oligo(U)nN, or the anchored primer, oligo(U)nV, is used as the RNA first-strand cDNA synthesis primer in order to prime all RNA molecules of interest (e.g., all mRNA molecules) in the sample for synthesis of first-strand cDNA molecules. In some embodiments, the anchor nucleotide position consists of ribonucleotides, but in other embodiments, the anchor nucleotide position consists of deoxyribonucleotides in order to preserve the coding sequence of the RNA molecules of interest (e.g., the mRNA molecules of interest) during subsequent steps and so that the complement of this nucleotide is present in the sense RNA molecules that have the RNA sequence tag joined to their 5'-termini which are synthesized in step (F) of the method. In some preferred embodiments, the RNA first-strand cDNA synthesis primer is an oligo(U)n(dN) primer in order to preserve the 3'-terminal nucleotide of the RNA molecules of interest that is encoded by genomic DNA. In some embodiments, terminal deoxynucleotidyl transferase is used to add a homopolymeric DNA sequence or RNA sequence (e.g., as described in U.S. Pat. No. 5,962,272; or in Schmidt, W M and Mueller, M W, Nucleic Acids Res., 27: e31, 1999) to the 3'-hydroxyl termini of first-strand cDNA molecules from step (B); in these embodiments, it is preferred that the 3'-terminal or anchor nucleotide position of the RNA first-strand cDNA synthesis primers is a ribonucleotide so that the RNA first-strand cDNA synthesis primers will not be substantially extended by the terminal transferase in step (D) of the method. In other embodiments, one or more specific-sequence RNA first-strand cDNA synthesis primers are used in order to synthesize multiple sense RNA molecules from one or a defined number of known-sequence RNA molecules of interest (e.g., known-sequence mRNA molecules) in the sample.

The invention includes different embodiments wherein different RNA molecules of interest are used in the method as templates for synthesis of first-strand cDNA molecules. In some preferred embodiments, the first-strand cDNA molecules are synthesized in step (B) using RNA molecules of interest comprising eukaryotic polyadenylated messenger RNA (mRNA) as the template. In some embodiments, the first-strand cDNA molecules are synthesized in step (B) using, as a template, RNA molecules of interest selected from the group consisting of: (i) prokaryotic mRNA; (ii) non-polyadenylated eukaryotic mRNA; (iii) snRNA; (iv) miRNA; (v) RNAi; (vi) siRNA; and (vi) ncRNA; and (vii) RNA synthesized in vitro using an RNA amplification reaction (e.g., including the method of the present invention comprising steps (A) through (F) or steps (A) through (K), or any portion of the steps thereof) or another method wherein double-stranded cDNA molecules obtained by reverse transcription of RNA molecules (e.g., derived from one or more eukaryotic or prokaryotic cells) are transcribed using an RNA polymerase. In some embodiments, the first-strand cDNA molecules are synthesized in step (B) using, as a template, any of the RNA molecules of interest discussed herein, wherein the RNA molecules of interest are first polyadenylated (e.g., by incubating them with poly(A) polymerase and ATP under conditions and for sufficient time wherein polyadenylated RNA is synthesized) or wherein the RNA molecules of interest have an RNA sequence tag that is joined to their 3'-termini (e.g., by using the method described in U.S. Patent Application No. 20050153333 of Sooknanan). Thus, in some embodiments, the first-strand cDNA also comprises "complexing sequences" that are added during processes of some embodiments of the methods of the invention to facilitate joining of the DNA sequence tag or for another purpose. For example, a complexing sequence can provide a complementary sequence to which an oligonucleotide (e.g., an terminal tagging oligoribonucleotide; or a second-strand cDNA synthesis primer) used in a method of the invention can anneal or complex. A complexing sequence usually comprises a "tail" sequence that is added by means, including, but not limited to, non-templated addition of dCMP residues to first-strand cDNA molecules by reverse transcriptase pausing at cap structures of mRNA (in the presence or absence of manganese cations), controlled ribonucleotide tailing using terminal transferase, primer extension of the first-strand cDNA using an terminal tagging oligoribonucleotide as a template, or addition of a non-templated homopolymeric sequence using terminal transferase. If a complexing sequence is added to the first-strand cDNA primer extension product during a process of a method of the invention, it is desirable that a complexing sequence is chosen that does not affect the desired functionality (e.g., the functionality of a protein that it is desired to express in a cell by in vivo translation of the RNA), activity (e.g., the activity of the RNA which corresponds to that of the original activity of the RNA of interest in the sample in its biological source; e.g., as mRNA, as miRNA or as another RNA, as the case may be for the particular RNA in its biological source), or specificity (e.g., the annealing specificity of the sequence exhibited by the RNA as compared to that of the original annealing specificity of the RNA of interest in the sample) of the sense RNA molecule transcription products ultimately synthesized in subsequent steps using the double-stranded cDNA which has a functional double-stranded RNA polymerase promoter as a template.

Those with skill in the art will know how to design oligonucleotides, including the first-strand cDNA synthesis primers, and conditions, wherein the oligonucleotides anneal and form complexes with the RNA molecules of interest in the sample, including any complexing sequences, if any, in order to carry out the reactions of the method.

In some embodiments, the first-strand cDNA molecules are synthesized in a reaction mixture that contains, in addition to the canonical deoxyribonucleotides, dATP, dCTP, dGTP, and dTTP or dUTP, one or more modified deoxyribonucleoside-5'-triphosphates. In some embodiments, the modified deoxyribonucleotide is labeled with a dye moiety (e.g., an Alexa dye, a Cy dye, or any of the other dyes commonly used in the art). In other embodiments, the modified deoxyribonucleotide is labeled with a biotin moiety (e.g., biotin-labeled dUTP). In still other embodiments the modified deoxyribonucleotide is labeled with an aminoallyl group, which can be further labeled using a reactive dye reagent or a reactive biotinylation reagent (e.g., a biotinylation or dye reagent having an N-hydroxysuccinimidyl group). The labeled first-strand cDNA can be used for a number of applications known in the art (e.g., for use as a DNA probe or for use as labeled target for hybridizing to a nucleic acid array or microarray (e.g., from Affymetrix, NimbleGen Systems, or Illumina).

In some preferred embodiments of the methods of the present invention, one or more oligoribonucleotides or RNA first-strand cDNA synthesis primers are used in step (B). As used herein, an "oligoribonucleotide first-strand cDNA synthesis primer" or "RNA first-strand cDNA synthesis primer" means one or more first-strand cDNA synthesis primers comprising ribonucleotides that are capable of being extended by the RNA-dependent DNA polymerase using the RNA molecules of interest as templates, wherein at least one of the one or more RNA first-strand cDNA synthesis primers is complementary to each RNA molecule of interest in the sample. In preferred embodiments, the one or more first-strand cDNA synthesis primers, when present in unhybridized single-stranded form, are capable of being degraded in step (C) (e.g., using one or more single-strand-specific RNase enzymes). Preferably, the "RNA first-strand cDNA synthesis primer" is digested to mononucleotides or short oligonucleotides that are not capable of being extended by the RNA-dependent DNA polymerase under the conditions used in the method. In some preferred embodiments, the RNA first-strand cDNA synthesis primer consists entirely or primarily of ribonucleotides. However, in other embodiments, the RNA first-strand cDNA synthesis primer also comprises deoxyribonucleotides interspersed with ribonucleotides, provided however, that the location of the deoxyribonucleotides and the ribonucleotides in the RNA first-strand cDNA synthesis primer is such that, upon being degraded in step (C) (e.g., using one or more single-strand-specific RNase enzymes), the digestion products are not capable of being extended by the RNA-dependent DNA polymerase using the RNA molecules of interest as templates. The ribonucleotide composition of the RNA first-strand cDNA synthesis primers is important because, following synthesis of first-strand cDNA molecules in step (B), the RNA first-strand cDNA synthesis primers are efficiently removed from the reaction mixture by digestion with single-strand-specific RNase in step (C). Therefore, substantially all of the RNA first-strand cDNA synthesis primers are eliminated using the method of the present invention, so they are not present and cannot be joined to a DNA sequence tag in step (D), and substantially no sense RNA molecules that are complementary to only RNA first-strand cDNA synthesis primers that have the DNA sequence tag joined to their 3'-termini are synthesized. Thus, the present method solves the common problem of other methods in the art, which result in high "background" due to undesired amplification of the nucleic acids that are derived from RNA first-strand cDNA synthesis primers rather than from the RNA molecules of interest. The type of RNA first-strand cDNA synthesis primers used varies in different embodiments of the invention based on the RNA molecules of interest and the intended application.

In some preferred embodiments wherein the RNA molecules of interest comprise polyadenylated RNA, the RNA first-strand cDNA synthesis primers provided in step (A) consist of "oligo(U)n", also referred to as "oligo(rU)n" or "poly(rU)n" or "poly(U)n", wherein "n" comprises a number between about six and about fifty, although the length of an oligo(U)n RNA first-strand cDNA synthesis primer is not limited to a specific length and can be of any length so long as it is capable of annealing to the 3'-poly(A) tail of the RNA molecules of interest and is capable of being extended by the RNA-dependent DNA polymerase. In some preferred embodiments, the oligo(U) RNA first-strand cDNA synthesis primer has a length of about 18 to about 24 uracil ribonucleotides (i.e., "rU" or "U" nucleotides), e.g., referred to, respectively, as "oligo(U)$_{18}$" and "oligo(U)$_{24}$". We sometimes refer to the oligo(U)n RNA first-strand cDNA synthesis primer as "oligo(U)" herein, without designating the number of U nucleotides.

In other preferred embodiments wherein the RNA molecules of interest have a poly(A) tail, the RNA first-strand cDNA synthesis primer, in addition to comprising the oligo (U) portion, comprises, in the last one or two positions of the 3'-terminal portion of the sequence, nucleotides that do not have a U or T nucleic acid base called "anchor nucleotides," which anneal to the 3'-genomic DNA-encoded region of the RNA molecules of interest just 5'- of the poly(A) sequence. These RNA first-strand cDNA synthesis primers are referred to generally as "anchored primers" and, more specifically as an "anchored oligo(U)" primer or an "oligo(U)nVy" primer, wherein "n" comprises a number between about six and about fifty, "V" comprises a randomized anchor ribonucleotide or deoxyribonucleotide consisting of any one of an equal molar mixture of three ribonucleotides or deoxyribonucleotides having A, C, and G, nucleic acid bases (e.g., in mixture consisting of equal molar amounts of each of the three nucleotides), and "y" is the number 1 or 2. In preferred embodiments, y=1, and the anchored primer is referred to as "oligo (U)nV" wherein "V" is a ribonucleotide, or "oligo(U)n(dV)" wherein "dV" is a deoxyribonucleotide. Thus, for example, if the RNA molecules of interest comprise 3'-polyadenylated mRNA, the anchor nucleotides serve to "anchor" the mRNA-complementary portion of the oligo(U)nV or oligo(U)n(dV) RNA first-strand cDNA synthesis primer to a nucleotide of the protein-coding sequence of the mRNA molecules. In other preferred embodiments, the anchor nucleotide comprises a randomized nucleotide for priming all RNA molecules of interest (e.g., all mRNA molecules) in a sample (e.g., the anchor nucleotide of the oligo(U)nV or oligo(U)n(dV) RNA first-strand cDNA synthesis primer is synthesized using a mixture of the three A, C, and G, nucleotides other than U or T).

In some embodiments, wherein the RNA molecules of interest exhibit only one defined sequence (e.g., one mRNA molecule of interest or multiple mRNA molecules of interest that share a common sequence or sequence motif), an anchor nucleotide that is complementary to a specific nucleotide is used; for example, an oligo(U)nG RNA first-strand cDNA synthesis primer can be used if the 3'-terminal nucleotide that is 5'- of the poly(A) tail is C.

In other embodiments, the nucleotide at the 3'-terminus of the oligo(U) RNA first-strand cDNA synthesis primer is synthesized using all four A, C, G, and U or T nucleotides, which results in an oligonucleotide referred to as an "oligo(U)nN" or "oligo(U)n(dN)" RNA first-strand cDNA synthesis primer.

In some preferred embodiments, the 3'-terminal nucleotide of the RNA first-strand cDNA synthesis primer is a ribonucleotide. In some other preferred embodiments, the 3'-terminal nucleotide of the RNA first-strand cDNA synthesis primer is a deoxyribonucleotide. The use of a deoxyribonucleotide as the 3'-terminal nucleotide is beneficial in some embodiments wherein the RNA first-strand cDNA primer extension product would be digested by single-strand-specific RNase (e.g., if the complexes between the RNA molecules of interest and the first-strand cDNA molecules are denatured and do not reanneal prior to digestion with single-strand-specific RNase); thus, in this case, the ribonucleotides of the extended RNA first-strand cDNA synthesis primer are digested but the deoxyribonucleotide is not digested by single-strand-specific RNase, and the sense RNA molecules that have the RNA sequence tag joined to their 5'-termini which are synthesized by the RNA polymerase in step (F) will have the 3'-terminal nucleotide of the coding sequence.

In preferred embodiments wherein an anchored RNA first-strand cDNA synthesis primer is used, the anchor nucleotide is used only for the most 3'-terminal nucleotide, selected from among a ribonucleotide and a deoxyribonucleotide. In some preferred embodiments wherein the RNA first-strand cDNA synthesis primer provided in (A) is oligo(U) or oligo(U)nN or oligo(U)n(dN) or oligo(U)nV or oligo(U)n(dV), the RNA molecules of interest provided in step (A) are mRNA molecules that are polyadenylated (i.e., which have 3'-poly(A) tails). In some other embodiments wherein the RNA first-strand cDNA synthesis primer provided in step (A) is oligo(U) or oligo(U)nN or oligo(U)n(dN) or oligo(U)nV or oligo(U)n(dV), the RNA molecules of interest have a poly(A) tail that is added to their 3'-termini using a poly(A) polymerase or by in vitro or in vivo transcription of a DNA template, such as a gene cloned in a vector wherein the template strand has a poly(dT) sequence at the 5'-end of the coding sequence.

In some embodiments, the RNA molecules of interest comprise one or a defined number of RNA molecules that have a known sequence and each of the RNA first-strand cDNA synthesis primers provided in step (A) has a sequence that is complementary to one of the known sequences. RNA first-strand cDNA synthesis primers that are complementary to specific known sequences of one or more RNA molecules of interest are referred to herein as "specific-sequence RNA first-strand cDNA synthesis primers" or "defined-sequence RNA first-strand cDNA synthesis primers." In some embodiments wherein a defined-sequence RNA first-strand cDNA synthesis primer is used in the method, some or all of the sequences exhibited by the RNA first-strand cDNA synthesis primer that are complementary to the RNA molecules of interest are lost when the first-strand cDNA primer extension product is treated with single-strand-specific RNase during step (C) of the method. However, in some embodiments, these sequences remain annealed to the RNA molecules of interest and are not digested since single-strand-specific RNase (e.g., RNase I) does not digest double-stranded RNA.

In some embodiments, the one or more RNA molecules of interest have a sequence tag that is joined to their 3'-termini using the method described in U.S. Patent Application No. 20050153333 of Sooknanan, and the RNA first-strand cDNA synthesis primer that is provided in step (A) comprises only ribonucleotides, but is a defined-sequence RNA first-strand cDNA synthesis primer that is complementary to the sequence tag rather than to the coding sequence of the RNA molecules of interest.

In some other preferred embodiments, the RNA first-strand cDNA synthesis primers provided in step (A) are "random-sequence RNA first-strand cDNA synthesis primers," meaning a mixture of oligoribonucleotides that contains all possible sequences. Examples of random-sequence RNA first-strand cDNA synthesis primers include, but are not limited to, random hexamers, random hepatamers, random octamers, and random nonamers. A random-sequence RNA first-strand cDNA synthesis primer can be made using an oligoribonucleotide synthesizer by including ribonucleotide reagents that are complementary to each of the four A, C, G, and U canonical bases during the chemical synthesis of each nucleotide position of the oligoribonucleotide. A random-sequence RNA first-strand cDNA synthesis primer can be used to amplify all portions of the RNA molecules of interest, including both intact and fragmented RNA molecules of interest (e.g., degraded RNA molecules of interest that are present in a specimen, such as a fomalin-fixed paraffin-embedded (FFPE) tissue section). It is known that use of oligo(dT) to prime synthesis of first-strand cDNA molecules from 3'-polyadenylated mRNA results in synthesis of a greater proportion of first-strand cDNA molecules that are complementary to the 3'-portion of the mRNA than are complementary to the 5'-portion of the mRNA (i.e., there is a 3'-bias), whereas there is less 3'-bias (but some 5'-bias) if random-sequence RNA first-strand cDNA synthesis primers are used to synthesize the first-strand cDNA molecules. Thus, random-sequence or semi-random (discussed below) RNA (or DNA, in some embodiments, first-strand cDNA synthesis primers (or, in some embodiments, DNA first-strand cDNA synthesis primers) are provided in step (A) of some embodiments, either alone or in combination with a poly(A)-specific primer (e.g., an oligo(U) or an oligo(U)nN or an oligo(U)n(dN) or oligo(U)nV or an oligo(U)n(dV) RNA first-strand cDNA synthesis primer), or in combination with another first-strand cDNA synthesis that exhibits a motif sequence or another sequence that is specific for a particular group of RNA molecules of interest) wherein the RNA molecules of interest are fragmented in the tissue (e.g., due to degradation of RNA molecules of interest obtained from formalin-fixed paraffin-embedded tissue sections) or by intential fragmentation. Random-sequence RNA first-strand cDNA synthesis primers are also provided in some embodiments, either alone or in combination with an oligo(U) or an oligo(U)nN or an oligo(U)n(dN) or oligo(U)nV or an oligo(U)n(dV) RNA first-strand cDNA synthesis primer, wherein it is desired to use the method to amplify exons of the RNA molecules of interest (e.g., to obtain "full coverage" of all sequences exhibited by the RNA molecules of interest). Random-sequence RNA first-strand cDNA synthesis primers are generally not preferred in embodiments wherein the method is used to generate full-length copies of the mRNA molecules of interest (e.g., full-length sense RNA copies of mRNA molecules from a cell).

In some other embodiments, semi-random RNA first-strand cDNA synthesis primers are used. As used herein, a "semi-random RNA first-strand cDNA synthesis primer" means a mixture of oligoribonucleotides that are complementary to only one, two, or three, rather than all four, of the canonical ribonucleotides (i.e., A, U, C, and G) at one or more positions of the oligonucleotide. Semi-random first-strand cDNA synthesis primers can be made using an oligoribonucleotide synthesizer by including reagents for chemical synthesis of nucleotides that are complementary to only one, two, or three, rather than all four, of the canonical ribonucleotides during the chemical synthesis of the one or more nucleotide positions of the oligoribonucleotide that are semi-random, and then including reagents for chemical synthesis of all four of the canonical ribonucleotides for the remaining nucleotide positions of the portion of the RNA first-strand cDNA synthesis primers that are complementary to an RNA molecule of interest. A semi-random RNA first-strand cDNA synthesis primer can be used to amplify approximately all portions of the RNA molecules of interest, including both intact and fragmented RNA molecules of interest (e.g., degraded RNA molecules of interest that are present in a specimen, such as a fomalin-fixed paraffin-embedded (FFPE) tissue section). In some embodiments of the method, the RNA first-strand cDNA synthesis primer additionally comprises a 5'-flap, which exhibits an arbitrary defined sequence that is 5'- of the oligo(U), oligo(U)nN, oligo(U)n(dN), oligo(U)nV, oligo(U)n(dV), random, or defined sequences discussed above, which 5'-flap exhibits a sequence that is not substantially complementary to the sequences exhibited by the RNA molecules of interest.

Surprisingly and unexpectedly, during the course of experiments to develop the methods described herein, the applicants found that first-strand cDNA could be efficiently synthesized without using an RNA first-strand cDNA synthesis primer or any other exogenously added primer. Thus, for example, it was observed that, when total human reference RNA (Stratagene, La Jolla, Calif., USA) was used as the RNA of interest, it was not necessary to provide an RNA first-strand cDNA synthesis primer in order to synthesize first-strand cDNA molecules in embodiments of the method comprising steps (A) through (F), or comprising steps (A) through (K). This finding was also confirmed with other samples containing other RNA molecules of interest. Thus, in some embodiments, no first-strand cDNA synthesis primer is provided in step (A). The sense RNA molecules that that had an RNA sequence tag joined to their 5'-termini that were synthesized in step (F), wherein no first-strand cDNA synthesis primer was provided in step (A) or used in step (B), exhibited sequences of expressed human genes and could be detected by RT-PCR as being present in approximately the same abundance as in the embodiments that used an RNA first-strand cDNA synthesis primer for synthesis of the first-strand cDNA in step (B). The quantities and size distributions of the sense RNA molecules that had an RNA sequence tag joined to their 5'-termini that were synthesized in embodiments wherein step (B) was performed in the absence of an RNA first-strand cDNA synthesis primer were similar even when different RNA-dependent DNA polymerases were used for the method (e.g., with MMLV reverse transcriptase, AMV reverse transcriptase, and with different SuperScript™ reverse transcriptases with reduce or no RNase H activity (Invitrogen Corporation, Carlsbad, Calif., USA), or when the RNA of interest was treated with RNase-free DNase I or Baseline-Zero™ DNase (EPICENTRE Biotechnologies, Madison, Wis., USA under conditions and for sufficient time wherein any contaminating DNA was substantially digested so that it was not capable of priming synthesis of DNA in the presence of the RNA-dependent DNA polymerase. Without being bound by theory, the applicants believe that the RNA molecules of interest in the sample are serving as primers for synthesis of first-strand cDNA molecules by the RNA-dependent DNA polymerase in step (B), which priming is either intramolecular or intermolecular priming. Thus, the present invention also comprises embodiments of any of the methods of the invention comprising step (B), wherein no RNA first-strand cDNA synthesis primers are provided in step (A), and step (B) comprises the step of contacting the RNA molecules of interest with the RNA-dependent DNA polymerase, in the absence of added RNA first-strand cDNA synthesis primers in the reaction mixture, under conditions and for sufficient time wherein first-strand cDNA molecules are synthesized (even wherein the sample containing the RNA molecules of interest provided in step (A) is free of DNA).

In some embodiments of any of the methods comprising step (B), one or more first-strand cDNA synthesis primers comprising deoxyribonucleotides (i.e., DNA first-strand cDNA synthesis primers), at least one of which is complementary to each of the RNA molecules of interest in the sample, is provided in step (A) and is used in step (B).

In some embodiments wherein the sample contains one or more RNA molecules of interest that have a poly(A) tail on their 3'-termini, the one or more DNA first-strand cDNA synthesis primers is selected from the group consisting of: an oligo(dU)n or an anchored oligo(dU)n primer (e.g., an oligo (dU)nV primer); an oligo(dT)n primer or an anchored oligo (dT)n primer (e.g., an oligo(dT)nV primer); an oligo(dU)n or an anchored oligo(dU)n promoter primer; an oligo(dT)n or an anchored oligo(dT)n promoter primer; an oligo(dU)n or an anchored oligo(dU)n primer that has an arbitrary desired sequence on its 5' terminus that is not complementary to the RNA molecules of interest; and an oligo(dT)n or an anchored oligo(dT)$_n$ primer that has an arbitrary desired sequence on its 5' terminus that is not complementary to the RNA molecules of interest and that is not a proto-promoter sequence. In some other embodiments, the one or more DNA first-strand cDNA synthesis primers is selected from the group consisting of: one or more primers, each of which exhibits: a specific sequence that is complementary to an RNA molecule of interest; a random-sequence primer; or a semi-random-sequence primer.

The invention is not limited to a particular concentration of the DNA first-strand cDNA synthesis primers so long as it functions for its intended purpose in priming synthesis of first-strand cDNA molecules. However, the applicants have observed that, if the concentration of DNA first-strand cDNA synthesis primers is greater than about 10 micromolar, the background synthesis of RNA (i.e., in the absence of input RNA molecules of interest in the sample) in step (F) or step (K) is higher than when first-strand cDNA synthesis primers comprising ribonucleotides or when lower concentrations of first-strand cDNA synthesis primers comprising deoxyribonucleotides are used. In some preferred embodiments wherein the one or more first-strand cDNA synthesis primers comprises deoxyribonucleotides, the concentration of the first-strand cDNA synthesis primers used in the solution in step (B) is less than or equal to about 2.5 micromolar. In some preferred embodiments wherein the one or more first-strand cDNA synthesis primers comprises deoxyribonucleotides, the concentration of the first-strand cDNA synthesis primers used in the solution in step (B) is less than or equal to about 1.25 micromolar.

In some embodiments wherein one or more first-strand cDNA synthesis primers that comprise deoxyribonucleotides are used, following synthesis of first-strand cDNA molecules that are complementary to the RNA molecules of interest, step (C) additionally comprises the sub-step of: incubating the solution under conditions and for sufficient time wherein the one or more first-strand cDNA synthesis primers are degraded.

In some embodiments wherein oligo(dU)n or anchored oligo (dU)n primers are used as the one or more first-strand cDNA synthesis primers in step (B), step (C) additionally comprises the sub-steps of: providing uracil-N-glycosylase (also known as UNG, uracil-DNA glycosylase, or UDG); and incubating the reaction mixture with the uracil-N-glycosylase under conditions and for sufficient time wherein the one or more first-strand cDNA synthesis primers are degraded. In some embodiments, in addition to UNG, step (C) additionally comprises providing endonuclease IV (endo IV) and incubating the reaction mixture with the uracil-N-glycosylase and the endo IV (both available from EPICENTRE Biotechnologies, Madison, Wis., USA) under conditions and for sufficient time wherein the one or more first-strand cDNA synthesis primers are degraded.

In some embodiments wherein the one or more first-strand cDNA synthesis primers used in step (B) comprise deoxyribonucleotides, wherein said primers are selected from the group consisting of: an oligo(dU)n or an anchored oligo(dU)n primer (e.g., an oligo(dU)nV primer); an oligo(dT)n primer or an anchored oligo(dT)n primer (e.g., an oligo(dT)nV primer); an oligo(dU)n or an anchored oligo(dU)n primer that has an arbitrary desired sequence on its 5' terminus that is not complementary to the RNA molecules of interest and that is not a proto-promoter sequence; an oligo(dT)n or an anchored oligo(dT)n primer that has an arbitrary desired sequence on its 5' terminus that is not complementary to the RNA molecules of interest and that is not a proto-promoter sequence; a random-sequence primer; and a semi-random-sequence primer, step (C) additionally comprises the sub-steps of: providing one or more ssDNA exonucleases that specifically degrades only single-stranded DNA; and incubating the reaction mixture with the one or more ssDNA exonucleases under conditions and for sufficient time wherein the one or more first-strand cDNA synthesis primers are degraded. In some embodiments, the one or more ssDNA exonucleases are selected from among: exonuclease I; exonuclease VII; and Rec J exonuclease (all available from EPICENTRE Biotechnologies, Madison, Wis., USA); in some embodiments wherein the primers comprise dU nucleotides, in addition to the one or more ssDNA exonucleases, uracil-N-glycosylase or uracil-N-glycosylase and endo IV are also provided and are also used in step (C) to degrade the primers following synthesis of first-strand cDNA molecules that are complementary to the RNA molecules of interest.

Inactivating the RNA-Dependent DNA Polymerase Used in Step (B) or Step (D) or the DNA-Template-Specific DNA Polymerase Used in Step (E).

In some embodiments, the one or more RNA-dependent DNA polymerases and/or the DNA-template-specific DNA polymerase is inactivated after synthesis of the respective nucleic acid molecules for which they are intended, wherein inactivation of the respective DNA polymerase is carried out prior to performing subsequent steps of the method in which undesired DNA synthesis could occur, potentially resulting in non-specific "background." Thus, for example, in some preferred embodiments, the RNA-dependent DNA polymerase is inactivated after synthesis of the first-strand cDNA molecules that have the DNA sequence tag joined to their 3'-termini. Undesired background DNA can cause problems such as lower sensitivity, or difficulty to interpret the results obtained using the sense RNA molecules.

Any method that prevents undesired DNA synthesis by the respective DNA polymerase in subsequent steps of the method, wherein undesired DNA synthesis could occur, can be used to inactivate the DNA polymerase. In some preferred embodiments, the DNA polymerase is inactivated by heat treatment. For example, but without limitation, in one preferred embodiment, the respective DNA polymerase is inactivated, following use for synthesis of DNA, by incubating the reaction mixture at about 80 to 95 degrees centigrade for about three to five minutes. However, in some embodiments wherein a thermostable DNA polymerase is used, a higher temperature or a longer time is needed for thermal inactivation, or another method for inactivating the activity of the respective DNA polymerase is required. In some other embodiments, the activity of the respective DNA polymerase is inactivated by treating the reaction mixture with a thermolabile alkaline phosphatase that is capable of degrading the dNTP nucleotides under conditions and for sufficient time wherein the dNTPs are digested; however, this method for inactivating the respective activity of the DNA polymerase is not preferred. For example, if this method is used to inactivate the RNA-dependent DNA polymerase used in step (B) or step (D), it is necessary to add more dNTPs for the reactions in step (D) or step (E), respectively. If a thermolabile alkaline phosphatase is used to inactivate the respective DNA polymerase, it can be any thermolabile alkaline phosphatase that is capable of removing one or more 5'-phosphates from dNTPs. In some embodiments, the thermolabile alkaline phosphatase is selected from among NTPhos™ thermolabile phosphatase (EPICENTRE Biotechnologies, Madison, Wis., USA) and shrimp alkaline phosphatase.

Step (C): Incubating the Solution from Step (B) Under Conditions and for Sufficient Time Wherein RNA that is Annealed to DNA and Single-Stranded RNA are Degraded After synthesis of the first-strand cDNA molecules in step (B), the first-strand cDNA molecules are "annealed to" or "hybridized to" or "complexed with" or "in a complex with" the RNA template. In some preferred embodiments, the RNA molecules of interest that served as templates for synthesis of first-strand cDNA molecules and the RNA first-strand cDNA synthesis primers are degraded (or removed) in step (C).

In some preferred embodiments, step (C) comprises: incubating the solution from step (B) with RNase H and a single-strand-specific RNase under conditions and for sufficient time wherein RNA that is annealed to DNA and single-stranded RNA are degraded.

The RNase H digests RNA that is annealed to (or "hybridized to" or "complexed with" or "in a complex with") DNA. In some preferred embodiments, *E. coli* RNase H (EPICENTRE Biotechnologies, Madison, Wis., USA) is used because it is effective and is easy to heat-inactivate following removal of the RNA that is annealed to DNA in the solution. In some embodiments, a thermostable RNase H, such as, but not limited to, Hybridase™ RNase H (EPICENTRE Biotechnologies, Madison, Wis., USA), *Thermus thermophilus* RNase H, or *Thermus flavus* RNase H, is used is step (C) of the method; however, thermostable RNase H is not preferred because it is more difficult to heat inactivate. Most wild-type reverse transcriptase enzymes have an RNase H activity in addition to their polymerase activity. Thus, in some embodiments, the RNase H activity comprises the RNase H activity of the RNA-dependent DNA polymerase that is used for reverse transcription (e.g., the RNase H activity of unmodified MMLV or AMV reverse transcriptase), in addition to or in place of the RNase H activity of an RNase H enzyme that lacks polymerase activity. In preferred embodiments, an RNase H enzyme that lacks DNA polymerase activity, such as *E. coli* RNase H, is used.

The single-strand-specific RNase digests excess RNA first-strand cDNA synthesis primers that did not prime synthesis of first-strand cDNA molecules and single-stranded RNA in the sample that did not serve as a template for synthesis of first-strand cDNA molecules (e.g., which were not RNA molecules of interest). In some preferred embodiments, *E. coli* RNase I (EPICENTRE Biotechnologies, Madison, Wis., USA) is used as the single-strand-specific RNase because it is effective and this enzyme can be inactivated by heat treatment. In some other embodiments, another single-strand-specific RNase (e.g., RNase A) can be used. However, RNase A is not preferred because it is more difficult to inactivate and is more easily reactivated under some conditions.

In some preferred embodiments wherein RNase H and a single-strand-specific RNase are used, step (C), additionally comprises the sub-step of inactivating the RNase H and single-strand-specific RNase. In some preferred embodiments wherein *E. coli* RNase H and *E. coli* RNase I (EPICENTRE Biotechnologies, Madison, Wis., USA) are used, step (C) additionally comprises the sub-step of inactivating the RNase H and the RNase I by heating the reaction mixture at about 95 degrees centigrade for about five minutes. However, if a different RNase H or a different single-strand-specific RNase is used or if the enzymes are used in other reaction mixtures (e.g., containing betaine or other thermo-protectant compounds), then the temperature and duration parameters of the heat inactivation step are changed to those that are appropriate for inactivating the particular enzymes under the particular conditions used, which conditions are either known in the art or easily determined by those with skill in the art.

In some embodiments of the method, step (C) comprises: incubating the solution from step (B) with an alkaline (or basic) solution, such as, but not limited to sodium or potassium hydroxide (e.g., in 200 mM KOH, 50 mM DTT, 5 mM EDTA on ice for 10 minutes), after which step, the reaction mixture is neutralized before proceeding to the next step.

In some embodiments of the method, following synthesis of first-strand cDNA molecules in step (B) and prior to treatment with RNase H and the single-strand-specific RNase in step (C), the reaction mixture is heated to denature the complexes between the RNA molecules of interest and the first-strand cDNA molecules. In some embodiments, wherein the complexes between the RNA molecules of interest and the first-strand cDNA molecules are denatured, the complexes between the RNA molecules of interest and the first-strand cDNA molecules do not renature under the conditions used prior to the treatment with RNase H and the single-strand-specific RNase, and single-strand-specific RNase also digests the RNA portion of the first-strand cDNA molecules derived from the RNA first-strand cDNA synthesis primers. In some embodiments, wherein the complexes between the RNA molecules of interest and the first-strand cDNA molecules are denatured, but the complexes between the RNA molecules of interest and the first-strand cDNA molecules renature under the conditions used prior to the treatment with RNase H and the single-strand-specific RNase, the RNA portion of the first-strand cDNA molecules derived from the RNA first-strand cDNA synthesis primers is not digested by single-strand-specific RNase. In other embodiments of the method, wherein the complexes between the RNA molecules of interest and the first-strand cDNA molecules are not denatured prior to step (C), the RNA portion of the first-strand cDNA molecules from the RNA first-strand cDNA synthesis primers is not digested by the RNase H and the single-strand-specific RNase. In some embodiments, the RNA molecules of interest are dissociated (or denatured) from the first-strand cDNA molecules (e.g., by heating and then rapidly cooling) prior to treatment with RNase H and single-strand-specific RNase. In some embodiments, the complexes between the RNA molecules of interest and the first-strand cDNA molecules are not denatured prior to treatment with the RNase H, but then, following digestion with the RNase H, any remaining nucleic acid complexes are denatured and then treated with single-strand-specific RNase. In other embodiments, the RNA is not denatured from the first-strand cDNA molecules prior to treatment with RNase H and single-strand-specific RNase.

In some embodiments of the methods of the invention, the step of contacting the reaction mixture containing DNA and RNA with the RNase H and single-strand-specific RNase is instead replaced by the steps of: contacting the reaction mixture containing DNA and RNA with an alkaline solution (e.g., without limitation, a KOH solution) of a concentration and under conditions and for sufficient time wherein RNA is digested to a size that is not suitable for priming synthesis of DNA under the conditions used in the method (e.g., in 200 mM KOH, 50 mM DTT, 5 mM EDTA on ice for about 10 minutes); and then neutralizing the reaction mixture. However, in most embodiments, the step of contacting the reaction mixture containing DNA and RNA with the RNase H and single-strand-specific RNase is preferred.

Preferred embodiments of the invention include step (C) comprising: contacting the solution from step (B) under conditions and for sufficient time wherein RNA that is annealed to DNA and single-stranded RNA are degraded. However, in some embodiments (e.g., without limitation, wherein the RNA-dependent DNA polymerase is inactivated, e.g., by heating to 95 degrees centigrade for approximately 3-10 minutes, or wherein RNA does not interfere in the method, or RNA is removed from the first-strand cDNA molecules by purification), step (C) may be, but need not be, omitted from the method.

Step (D): Joining the DNA Sequence Tag to the 3'-Termini of First-Strand cDNA Molecules The present invention provides methods for synthesizing first-strand cDNA molecules that have a DNA sequence tag joined to their 3'-termini. The step of joining the DNA sequence tag to the 3'-termini of the first-strand cDNA molecules is an important aspect of embodiments of the invention, and is especially useful if the first-strand cDNA molecules exhibit a multiplicity of different sequences (e.g., first-strand cDNA molecules synthesized using RNA molecules of interest comprising substantially all mRNA molecules in the sample), or if the sequences exhibited by the first-strand cDNA molecules are unknown. The DNA sequence tag provides an annealing site for the 3'-portion of the second-strand cDNA synthesis primer, thereby providing a priming site for synthesis of second-strand cDNA molecules. In preferred embodiments of the method, the 5'-portion of the second-strand cDNA synthesis primer exhibits at least a portion of an anti-sense promoter sequence of an RNA polymerase promoter. Thus, in addition to providing an annealing site for the 3'-portion of the second-strand cDNA synthesis primer that is extended by the DNA-template-specific DNA polymerase for synthesis of second-strand cDNA molecules, the DNA sequence tag joined to the 3'-termini of the first-strand cDNA molecules is itself primer extended by the DNA-template-specific DNA polymerase using the 5'-portion of the second-strand cDNA synthesis primer as a template, thereby synthesizing double-stranded cDNA molecules that are functionally joined to the RNA polymerase promoter in step (E) (meaning that DNA that exhibits the sense promoter sequence is joined to the 3'-termini of the first-strand cDNA molecules). Then, by contacting the double-stranded cDNA molecules that are functionally joined to the RNA polymerase promoter with the RNA polymerase that recognizes and binds the promoter under transcription conditions in step (F) of the method, multiple copies of sense RNA molecules that exhibit substantially the same sequences as the RNA molecules of interest are synthesized, each of which has an RNA sequence tag joined to its 5'-terminus, at least a part of which is complementary to the DNA sequence tag.

Providing the Terminal Tagging Oligoribonucleotide

As used herein, a "terminal tagging oligonucleotide" means an oligonucleotide that has a 5'-portion and a 3'-portion, wherein the 5'-portion exhibits a sequence that is complementary to an arbitrary DNA sequence tag that it is desired to join or add to the 3'-termini of one or more DNA molecules of interest, and wherein the 3'-portion comprises or consists of at least three random nucleotides (e.g., 3 to 8 random nucleotides; e.g., preferably 7 random nucleotides), of which, the 3'-terminal nucleotide is not capable of being extended by a DNA polymerase in the presence of a single-stranded DNA that could serve as template. In some preferred embodiments, the 5'-portion of the terminal tagging oligonucleotide does not exhibit a proto-promoter sequence. Since the 3'-portion of a terminal tagging oligonucleotide exhibits a random sequence, the 3'-portion of at least one terminal tagging oligonucleotide exhibits a sequence that is capable of annealing to the 3'-terminal portion of the one or more DNA molecules of interest, wherein, upon annealing to the one or more DNA molecules of interest, the 5'-portion is a template for extension of the 3'-termini of the DNA molecules of interest by a DNA polymerase. As used herein, a "terminal tagging oligoribonucleotide" means a terminal tagging oligonucleotide that comprises, except for the 3'-terminal nucleotide, only or predominantly ribonucleotides. In preferred embodiments, the terminal tagging oligoribonucleotide, if incubated with single-strand-specific RNase provided in step (A), is digested to mononucleotides or short oligonucleotides which, under the conditions used in the method, are not capable of serving as primers for extension by a DNA polymerase in the presence of single-stranded DNA that could serve as a template.

In preferred embodiments, the terminal tagging oligoribonucleotide comprises or consists of a 5'-portion and 3'-portion, wherein the 5'-portion is complementary to the sequence of the DNA sequence tag that it is desired to join to the 3'-termini of the first-strand cDNA molecules in step (D), and the 3'-portion comprises or consists of at least three random nucleotides (e.g., 3 to 8 random nucleotides; e.g., preferably 7 random nucleotides), of which, the 3'-terminal nucleotide is not capable of being extended by the RNA-dependent DNA polymerase in the presence of the first-strand cDNA molecules or other single-stranded DNA that could serve as a template. In preferred embodiments, the 3'-portion of the terminal tagging oligoribonucleotide consists of between three and seven random nucleotides. In some preferred embodiments, the 3'-portion of the terminal tagging oligoribonucleotide consists of seven random nucleotides, which is approximately the maximum number of random nucleotides that is practical, since, with each additional random nucleotide, the minimum mass of the terminal tagging oligoribonucleotide that is required in order for every possible sequence to be present in the reaction mixture quadruples. If the 3'-portion of the terminal tagging oligoribonucleotide consists of seven random nucleotides, the terminal tagging oligoribonucleotides will exhibit 16,384 different 7-nucleotide sequences in their 3'-portions. Thus, it is preferred that the molar amount of the terminal tagging oligoribonucleotide is sufficient so that all of the 16,384 different sequences will be present in the reaction mixture, and that any one sequence is present in sufficient abundance to be capable of annealing to all of the copies of each first-strand cDNA molecules, which in turn, should correspond to the number of copies of all of the RNA molecules of interest. In some embodiments, the 3'-portion of the terminal tagging oligoribonucleotide can consist of more or less than seven random nucleotides, even if some of the nucleotides at the 3'-terminal portion of the terminal tagging oligoribonucleotide do not anneal to the 3'-terminal portion of the first-strand cDNA molecules synthesized in step B, provided that the number of random nucleotides is sufficient so that the first-strand cDNA molecules synthesized from substantially all of the RNA molecules of interest are capable of annealing to at least one terminal tagging oligoribonucleotide and being extended by the RNA-dependent DNA polymerase. In some embodiments, not all of the random 3'-portion of the terminal tagging oligoribonucleotide anneals to one or more first-strand cDNA molecules, provided however, that at least the 3'-termini, including the 3'-terminal nucleotide, of the first-strand cDNA molecules anneal to the terminal tagging oligoribonucleotide and are extended by the RNA-dependent DNA polymerase in step (D).

In some preferred embodiments, the terminal tagging oligoribonucleotide consists entirely of ribonucleotides, with the exception of the 3'-terminal nucleotide, which nucleotide is modified so that it is not capable of being extended by a DNA polymerase in the presence of a single-stranded DNA that could serve as a template. In some embodiments, the terminal tagging oligoribonucleotide consists primarily, but not entirely, of ribonucleotides. In some embodiments, the terminal tagging oligoribonucleotide also comprises deoxyribonucleotides interspersed with ribonucleotides, provided however, that the location of the deoxyribonucleotides and the ribonucleotides in the terminal tagging oligoribonucleotide is such that, upon degradation of the unused terminal tagging oligoribonucleotide in a sub-step of step (D) (e.g., by digestion using a single-strand-specific RNase), the digestion products are not capable of annealing to a DNA molecule and being extended by a DNA polymerase. The ribonucleotide composition of the terminal tagging oligoribonucleotide is important because, following terminal tagging of the first-strand cDNA molecules in step (D), the terminal tagging oligoribonucleotides can be efficiently removed from the reaction mixture (e.g., by digestion with single-strand-specific RNase; e.g., as a sub-step of step (D)). Therefore, substantially all of the terminal tagging oligoribonucleotides are eliminated using the method of the present invention, so they are not present and cannot anneal to other DNA molecules, such as but not limited to, second-strand cDNA molecules, in subsequent steps of the method. Thus, the present method solves the common problem of other methods in the art, which result in high "background" due to undesired joining of the DNA sequence tag to other nucleic acids rather than only to the first-strand cDNA molecules.

In some embodiments, terminal tagging oligoribonucleotides wherein the 3'-portion exhibits a semi-random sequence, rather than a random sequence, are used in step (D) of the method; however, in preferred embodiments, the 3'-portion of the terminal tagging oligoribonucleotide exhibits a random sequence, rather than a semi-random sequence. As used herein, an "terminal tagging oligoribonucleotide, wherein the 3'-portion exhibits a semi-random sequence" or a "semi-random terminal tagging oligoribonucleotide" means a mixture of oligoribonucleotides that are complementary to only one, two, or three, rather than all four, of the canonical ribonucleotides (i.e., A, U, C, and G) at one or more positions of the 3'-portion of the terminal tagging oligoribonucleotide and that are complementary to all four of the canonical ribonucleotides at the other positions. Semi-random terminal tagging oligoribonucleotides can be made using an oligoribonucleotide synthesizer by including ribonucleotide reagents that are complementary to only one, two, or three, rather than all four, of the canonical ribonucleotides during the chemical synthesis of the one or more nucleotide positions of the 3'-portion of the RNA terminal tagging oligoribonucleotide that are semi-random, and then including reagents for chemical synthesis of all four of the canonical ribonucleotides during the chemical synthesis of the remaining nucleotide positions that are fully random.

In preferred embodiments, the terminal tagging oligoribonucleotide comprises only ribonucleotides, with the exception of the 3'-terminal nucleotide, which nucleotide can be a 3'-modified ribonucleotide or a 3'-deoxyribonucleotide, or a 2',3'-dideoxyribonucleotide, or another nucleotide that is blocked so that it is not capable of being extended by the RNA-dependent DNA polymerase. In some preferred embodiments, the 3'-terminal nucleotide comprises a random nucleotide that is modified with a 2'-O-methyl group and a 3'-propyl phosphate group (e.g., made using (1-dimethoxytrityloxy-propanediol-3-succinoyl)-long chain alkylamino-CPG or 3'-Spacer C3 CPG).

The 5'-portion of the terminal tagging oligoribonucleotide exhibits a sequence that is complementary to any DNA sequence tag that it is desired to join to the 3'-termini of the first-strand cDNA molecules in step (D).

In some embodiments, the 5'-portion of the terminal tagging oligoribonucleotide does not exhibit a proto-promoter sequence (e.g., as described in U.S. Pat. No. 5,169,766). However, in some embodiments, the terminal tagging oligoribonucleotide comprises a 5'-portion that exhibits a proto-promoter sequence. In embodiments wherein the terminal tagging oligoribonucleotide comprises a 5'-portion that exhibits a proto-promoter sequence, the first-strand cDNA synthesis primer is either an oligoribonucleotide or an oligonucleotide that comprises dU (e.g., oligo(dU)n or and anchored oligo(dU)n) that can be degraded to mononucleotides using a single-strand-specific RNase or using uracil-N-glycosylase, respectively.

The DNA sequence tag that is joined to the 3'-termini of the first-strand cDNA molecules provides a template for synthesis of at least a portion of the RNA sequence tag that is joined to the 5'-termini of the sense RNA molecules that are synthesized in step (F) of the method. Thus, the 5'-portion of the terminal tagging oligoribonucleotide exhibits a sequence that is the same as at least a portion of the sequence exhibited by the RNA sequence tag in the sense RNA molecules which are synthesized using the RNA polymerase in step (F). Since the RNA sequence tag is synthesized by the RNA polymerase using the DNA sequence tag as a template, it is important that the DNA sequence tag added to the 3'-termini of the first-strand cDNA molecules in step (D) exhibits a sequence that is easily transcribed by the RNA polymerase. In preferred embodiments, the sequence exhibited by the DNA sequence tag does not form hairpins or other secondary structures which prevent or decrease synthesis of the double-stranded cDNA molecules in step (E) or the subsequent transcription of the double-stranded cDNA molecules in step (F). In some preferred embodiments wherein the RNA sequence tag comprises the 5'-terminus of the sense RNA molecules synthesized in step (F) and the sense RNA molecules are subsequently capped using a capping enzyme (e.g., vaccinia virus capping enzyme), the sequence exhibited by the RNA sequence tag (and hence also the sequence exhibited by the DNA sequence tag) does not form a hairpin or other intramolecular or intermolecular structure that prevents or decreases that capability to cap the sense RNA molecules using the capping enzyme. Still further, since at least a portion of the DNA sequence tag provides a site for annealing of the second-strand cDNA synthesis primer, the sequence exhibited by the DNA sequence tag must be of sufficient length and provide sufficient binding strength (e.g., with a low enough Tm) so that second-strand cDNA synthesis primer can anneal to the DNA sequence tag and the DNA-template-specific DNA polymerase can extend the 3'-terminus of the second-strand cDNA synthesis primer using the first-strand cDNA molecules as a template. In some preferred embodiments, the DNA sequence tag exhibits a sequence that is complementary to at least a portion of an RNA sequence tag (note: that another portion of the RNA sequence tag can be derived from a sequence exhibited by the 5'-portion of the second-strand cDNA synthesis primer). In some embodiments, the RNA sequence tag comprises a 5'-untranslated leader sequence ("5'-UTL") that exhibits a sequence which is suitable for in vivo translation of the sense RNA molecules, provided the sense RNA molecules are first capped using a capping enzyme and polyadenylated using a poly(A) polymerase and ATP.

Designing Oligonucleotides for Performing Steps (D) and (E)

Those with skill in the art will know how to design oligonucleotides, including the terminal tagging oligoribonucleotide and the second-strand cDNA synthesis primer, and conditions, wherein portions of the oligonucleotides anneal and form complexes in order to carry out the reactions of the method. In general, this can be accomplished using commercially available computer software programs for sequence analysis, including programs for calculating melting temperature (Tm) and most likely structures formed by nucleic acid molecules that exhibit user-specified sequences, and reactions conditions known in the art.

Synthesizing First-Strand cDNA Molecules that have the DNA Sequence Tag Joined to their 3'-Termini Step (D) of the method comprises contacting the first-strand cDNA molecules to which the terminal tagging oligoribonucleotide is annealed with the RNA-dependent DNA polymerase in a reaction mixture and under conditions and for sufficient time wherein the 3'-termini of the first-strand cDNA molecules are extended using the terminal tagging oligoribonucleotide as a template and first-strand cDNA molecules that have the DNA sequence tag joined to their 3'-termini are synthesized. This sub-step will be understood by those with knowledge in the art based on reading the specification with respect to the RNA first-strand cDNA synthesis primers, the terminal tagging oligoribonucleotides, and the RNA-dependent DNA polymerase, as well as other sections that pertain thereto.

Degrading the Terminal Tagging Oligoribonucleotide (e.g., with RNase H and a Single-Strand-Specific RNase)

In some preferred embodiments of the invention, the method uses a terminal tagging oligoribonucleotide comprising only ribonucleotides, with the exception of the 3'-terminal nucleotide, which 3'-terminal nucleotide can be a 3'-modified ribonucleotide or a 3'-deoxyribonucleotide, or a 2',3'-dideoxyribonucleotide, or another nucleotide that is blocked so that it is not capable of being extended by the RNA-dependent DNA polymerase. In some embodiments, since the terminal tagging oligoribonucleotides comprise only or primarily ribonucleotides, they can be removed by contacting the reaction mixture with the RNase H and single-strand-specific RNase, or with alkali, as discussed related to step (C) of the method. Removing the terminal tagging oligoribonucleotides from the reaction mixture greatly reduces the possibility of background due to synthesis of DNA using the terminal tagging oligoribonucleotide as a template, or other reactions that could result in other artifactual background in subsequent steps of the method. Still further, removal of the terminal tagging oligoribonucleotides comprising only or primarily ribonucleotides is accomplished without need of a mini-column or other purification step, which is time-consuming and could result in losses of product molecules on the mini-column, and, less reliable results (e.g., if the method is used for analysis of gene expression).

In some preferred embodiments, step (D) additionally comprises the sub-step of: incubating the solution with RNase H and a single-strand-specific RNase under conditions and for sufficient time wherein RNA that is annealed to DNA and single-stranded RNA are degraded. In some preferred embodiments wherein step (D) comprises the sub-step of incubating the solution with RNase H and a single-strand-specific RNase under conditions and for sufficient time wherein RNA that is annealed to DNA and single-stranded RNA are degraded, step (D) additionally comprises the sub-step of inactivating the RNase H and single-strand-specific RNase. In those embodiments, the RNase H and single-strand-specific RNase are inactivated as discussed in the section related to step (C) above.

However, in some embodiments (e.g., without limitation, wherein the RNA-dependent DNA polymerase is inactivated, e.g., by heating to 95 degrees centigrade for approximately 3-10 minutes, and a DNA-template-specific DNA polymerase that does not have reverse transcriptase activity is used in step (E)), step (D) may comprise, but need not comprise, the sub-step of contacting the solution under conditions and for sufficient time wherein RNA that is annealed to DNA and single-stranded RNA are degraded.

Embodiments of Step (D) with Respect to Use of RNA Polymerases that Recognize Single-Stranded RNA Polymerase Promoters In some embodiments of the method, the RNA polymerase comprises a transcriptionally active 1,106-amino acid domain of the N4 vRNAP (herein designated "N4 mini-vRNAP"), which corresponds to amino acids 998-2103 of N4 vRNAP (Kazmierczak, K. M., et al., EMBO J., 21: 5815-5823, 2002), which RNA polymerase is capable of transcribing single-stranded, promoter-containing templates, and RNA polymerase promoters that it recognizes and reaction conditions are as described therein. In other embodiments an RNA polymerase pseudopromoter is used and the RNA polymerase provided is the RNA polymerase that recognizes the pseudopromoter. In embodiments of the method that use an RNA polymerase that recognizes a single-stranded RNA polymerase promoter or pseudopromoter, the compositions and steps related to synthesis of second-stranded cDNA molecules and double-stranded cDNA molecules are not used. In some preferred embodiments of the method wherein an RNA polymerase that recognizes a single-stranded RNA polymerase promoter or pseudopromoter are used, the 5'-portion of the terminal tagging oligoribonucleotide provided in step (D) exhibits a sequence that is complementary to a single-stranded RNA polymerase promoter or pseudopromoter that is recognized by the RNA polymerase, and first-strand cDNA molecules that have the single-stranded RNA polymerase promoter or pseudopromoter joined to their 3'-termini are synthesized by extension of the first-strand cDNA molecules by the RNA-dependent DNA polymerase using the 5'-portion of the terminal tagging oligoribonucleotide as a template in step (D) of the method. In some preferred embodiments, the first-strand cDNA molecules that have the single-stranded RNA polymerase promoter or pseudopromoter (which exhibits a sense promoter sequence) joined to their 3'-termini are then contacted with the RNA polymerase that recognizes the single-stranded RNA polymerase promoter or pseudopromoter under conditions and for sufficient time wherein sense RNA molecules that have an RNA sequence tag joined to their 5'-termini are synthesized. In these embodiments, step (E) is not necessary, step (F) comprises incubating the first-strand cDNA molecules that have the single-stranded RNA polymerase promoter or pseudopromoter joined to their 3'-termini (from step (D)) with the RNA polymerase that recognizes said single-stranded RNA polymerase promoter or pseudopromoter under conditions and for sufficient time wherein RNA is synthesized.

Step (E): Synthesis of the Double-Stranded cDNA Molecules that Contain a Functional RNA Polymerase Promoter In preferred embodiments of the method, step (E) comprises contacting the first-cDNA molecules that have the DNA sequence tag joined to their 3'-termini with the second-strand cDNA synthesis primer and the DNA-template-specific DNA polymerase under conditions and for sufficient time wherein double-stranded cDNA molecules that contain a double-stranded RNA polymerase promoter are synthesized. In preferred embodiments, this step is straightforward. The 3'-portion of the second-strand cDNA synthesis primer anneals to the DNA sequence tag of the first-strand cDNA molecules. Then, the DNA-template-specific DNA polymerase catalyzes extension of the 3'-termini of the second-strand cDNA molecules using the first-strand cDNA molecules as a template and extension of the 3'-termini of the first-strand cDNA molecules that have the DNA sequence tag joined to their 3'-termini using the 5'-portion of the second-strand cDNA synthesis primer as a template, thereby synthesizing double-stranded cDNA molecules. Since the 5'-portion of second-strand cDNA synthesis primer exhibits all or a portion of the anti-sense promoter sequence (and, if the second-strand cDNA synthesis primer exhibits only a portion or the anti-sense promoter sequence, then the DNA sequence tag exhibits the complement of the remaining portion), the double-stranded cDNA molecules synthesized using the DNA-template-specific DNA polymerase each have a functional double-stranded RNA polymerase promoter.

Step (F): Synthesis of Multiple Copies of Sense RNA Molecules that Exhibit Substantially the Same Sequence as the RNA Molecules of Interest In preferred embodiments of the method, step (F) comprises contacting the double-stranded cDNA molecules with the RNA polymerase that recognizes and binds the double-stranded RNA polymerase promoter under conditions and for sufficient time wherein multiple copies of sense RNA molecules are synthesized, each of which exhibits substantially the same sequence as an RNA molecule of interest in the sample and has the RNA sequence tag joined to its 5'-terminus. In some preferred embodiments, the RNA polymerase promoter is a T7-type RNA polymerase promoter and the RNA polymerase is the T7-type RNA polymerase it recognizes. In some preferred embodiments, the T7-type RNA polymerase promoter is selected from among a T7, T3 and an SP6 promoter and the RNA polymerase is the respective T7-type RNA polymerase that recognizes the promoter. In some preferred embodiments, the RNA polymerase promoter is a T7 RNA polymerase promoter and the RNA polymerase is T7 RNA polymerase.

In some preferred embodiments, the sense RNA molecules synthesized do not necessarily have perfect sequence identity to the RNA molecules of interest in the sample. For example, but without limitation, the sense RNA can contain: base-substituted ribonucleotides, such as 5-allyamino-UTP or biotinylated-UTP, dye-labeled ribonucleotides, which can be used to detected the sense RNA molecules (e.g., when they are used as target RNA for hybridization to probes on arrays or microarrays); or non-canonical nucleotide substrates such as dNTPs or 2'-substituted 2'-deoxyribonucleotides such as, but not limited to 2'-fluoro-, 2'-amino-, 2'-methoxy-, or 2'-azido-substituted 2'-deoxyribonucleotides (e.g., incorporated using, as a mutant RNA polymerase, such as the T7 RNAP Y639F mutant enzyme or the T7 RNAP mutant enzyme having altered amino acids at both positions 639 and 784, as described in Sousa et al., U.S. Pat. No. 5,849,546; Padilla, R and Sousa, R, Nucleic Acids Res., 15: e138, 2002; Sousa, R and Mukherjee, S, Prog Nucleic Acid Res Mol Biol., 73: 1-41, 2003, or another mutant RNA polymerase that has a similar mutation in the same amino acid position of the same amino motif as in the T7 RNAP Y639F mutant enzyme), which can provide properties such as resistance to RNase A; modified nucleotides, such as nucleotides that have intentional sequence alterations, such as sequence alterations introduced through a primer comprising a sequence that is hybridizable, but not complementary, to the RNA molecules of interest or to the first-strand cDNA derived therefrom; modified internucleoside linkages which are resistant to some nucleases, such as, phosphorothioate, phosphorodithioate, phosphoroselenate, orphosphorodiselenate linkages; and/or sequence errors that occur during in vitro transcription.

In some preferred embodiments, step (F) of the method results in synthesis of multiple copies of sense RNA molecules that exhibit substantially the same sequences as only the RNA molecules of interest (e.g., using oligo(U)n or an oligo(U)nV anchored primer, oligo(U)nN, or or a specific-sequence primer as the RNA first-strand cDNA synthesis primer for synthesis of first-strand cDNA molecules for all or specific-sequence mRNA molecules of interest). In other embodiments, step (F) of the method results in synthesis of multiple copies of sense RNA molecules that exhibit substantially the same sequences as the RNA molecules of interest and also, substantially the same sequences as the RNA molecules that are not of interest (e.g., using a RNA first-strand cDNA synthesis primer consisting of a random primer, such as a random hexamer primer). In some embodiments wherein sense RNA molecules that exhibit sequences of both RNA molecules of interest and RNA molecules that are not of interest are amplified, the multiple copies of sense RNA molecules that exhibit the same sequences as the RNA molecules of interest are used in an application that distinguishes those RNA molecules that have a sequence of an RNA molecule of interest from RNA molecules that have a sequence of an RNA molecule that is not of interest. For example, in some embodiments the sense RNA molecules that have a sequence of an RNA molecule of interest will anneal to a sequence on an array or microarray, whereas sense RNA molecules that have a sequence of an RNA molecule that is not of interest will not anneal to a sequence on the array or microarray.

Steps (G) through (K): Methods for Obtaining a Second Round of Amplification of First-Strand cDNA Molecules that have a DNA Sequence Tag on their 3'-Termini, Double-Stranded cDNA Molecules that Contain an RNA Polymerase Promoter, or Sense RNA Molecules that Exhibit Sequences that are Substantially the Same as the Sequence Exhibited by RNA Molecules of Interest in the Sample and that have an RNA Sequence Tag Joined to their 5'-Termini In some preferred embodiments of the method, the sense RNA molecules that have the RNA sequence tag joined to their 5'-termini, which are synthesized in step (F) of the method, are used in a second or subsequent round to synthesize additional sense RNA molecules that have the RNA sequence tag joined to their 5'-termini, each of which exhibits a sequence that is substantially the same as the sequence exhibited by an RNA molecule of interest in the sample. In this way, the invention provides methods for further amplifying the RNA molecules of interest in the sample. Since the sense RNA molecules already have the RNA sequence tag joined to their 5'-termini, it is not necessary to use an RNA-dependent DNA polymerase or a terminal tagging oligoribonucleotide during the second round of the method; the DNA sequence tag is added to the first-strand cDNA molecules in the second round by extension of the second-round first-strand cDNA synthesis primers using the sense RNA molecules that have the RNA sequence tag joined to their 5'-termini. After degrading or removing the RNA (e.g., using RNase H and, optionally, the single-strand-specific RNase), the double-stranded cDNA molecules that have a functional double-stranded RNA polymerase promoter are synthesized by extension of the second-round second-strand cDNA synthesis primers that anneal to the second-round first-strand cDNA molecules by the DNA-template-specific DNA polymerase.

The RNA sequence tag that is joined to the 5'-termini of the sense RNA molecules serves to fix or maintain the length of the sense RNA molecules obtained in step (F) that are provided in step (G) for synthesis of additional sense RNA molecules during a second or subsequent round of amplification. Thus, in some preferred embodiments, the sizes of the sense RNA molecules obtained in step (K) after the second round of synthesis of sense RNA molecules that have the RNA sequence tag joined to their 5'-termini are substantially the same sizes as the sense RNA molecules that have the RNA sequence tag joined to their 5'-termini obtained in step (F), which, in turn, are substantially the same sizes as the RNA molecules of interest provided in step (A).

In some preferred embodiments, the portion of the first-strand cDNA molecules derived from the RNA first-strand cDNA synthesis primers remains annealed to the 3'-termini of the RNA molecules of interest and is not digested by the RNase H and single-strand-specific RNase (e.g., RNase I) in step (C) of the method; thus, in these embodiments, the first-strand cDNA molecules that have the DNA sequence tag joined to their 3'-termini after step (D) of the method, also retain the sequence exhibited by the RNA first-strand cDNA synthesis primer, thereby also fixing the lengths of the double-stranded cDNA molecules that are synthesized in step (E) and the sense RNA molecules that have the RNA sequence tag joined to their 5'-termini that are synthesized in step (F). The lengths of the products in the second round are fixed by the sequence to which the second-round first-strand cDNA synthesis primers anneal and the RNA sequence tag to which the second-round second-strand cDNA synthesis primers anneal. Therefore, if the sense RNA molecules that have the RNA sequence tag joined to their 5'-termini from step (F) are provided in step (G) for use in a second round, the sense RNA molecules that have the RNA sequence tag joined to their 5'-termini that are synthesized in step (K) of the second round will exhibit substantially the same sequences and be substantially the same sizes. In some embodiments of the first round of the method, wherein the RNA first-strand cDNA synthesis primers-portion of the first-strand cDNA molecules that have the DNA sequence tag joined to their 3'-termini are not digested in step (C), the sequences exhibited by the second-round first-strand cDNA synthesis primers provided in step (G) are the same as the sequences exhibited by the RNA first-strand cDNA synthesis primers provided in step (A).

In other embodiments, wherein the RNA portions of the first-strand cDNA molecules derived from the RNA first-strand cDNA synthesis primers are digested in step (C), the sense RNA molecules that have the RNA sequence tag joined to their 5'-termini, which are synthesized in step (F), lack the 3'-termini to which the RNA first-strand cDNA synthesis primers annealed in step (B). Thus, in some of these embodiments, a new annealing site is joined to the 3'-termini of the sense RNA molecules that have the RNA sequence tag joined to their 5'-termini prior to providing them for a second round in step (G). Thus, in some embodiments, step (G) additionally comprises the sub-steps of providing an enzyme that is capable of joining a 3'-tag to the 3'-termini of the sense RNA molecules that have the RNA sequence tag joined to their 5'-termini and, prior to step (H), contacting the sense RNA molecules that have the RNA sequence tag joined to their 5'-termini with the enzyme that is capable of joining a 3'-tag to the 3'-termini in a reaction mixture and under conditions and for sufficient time wherein the 3'-tag, to which at least one of the second-round first-strand cDNA synthesis primers is capable of annealing, is joined to their 3'-termini. In some preferred embodiments, the enzyme that is capable of joining the 3'-tag to the 3'-termini of the sense RNA molecules that have the RNA sequence tag joined to their 5'-termini is poly (A) polymerase, and the 3'-tag is a poly(A) tail. Thus, in some embodiments, the method further comprises the sub-steps of providing poly(A) polymerase and ATP, and incubating the sense RNA molecules that have the RNA sequence tag joined to their 5'-termini with the poly(A) polymerase and the ATP in a reaction mixture and under conditions and for sufficient time wherein a a poly(A) tail is joined to their 3'-termini; in some of these embodiments, the method further comprises the sub-step of: inactivating the poly(A) polymerase. In some embodiments wherein a poly(A) tail is joined to their 3'-termini, the second-round first-strand cDNA synthesis primer provided in step (G) is selected from among an oligo(U)n primer, oligo(U)nN primer, an oligo(U)nV primer; an oligo (dT)n primer, an oligo(dT)nN primer, an oligo(dT)nV primer, an oligo(dU)n primer, an oligo(dU)nN primer, and an oligo (dU)nV primer, wherein n is an integer between about 6 and about 50, more preferably between about 12 and about 24. These poly(A)-tailed sense RNA molecules that have the RNA sequence tag joined to their 5'-termini are then provided in step (G) for synthesizing: a second round of first-strand cDNA molecules that have the DNA sequence tag joined to their 3'-termini; a second round of double-stranded cDNA molecules that contain the RNA polymerase promoter; or a second round of sense RNA molecules that have the RNA sequence tag joined to their 5'-termini. Thus, in some embodiments, the second-round first-strand cDNA synthesis primers are capable of annealing to a 3'-tag consisting of a poly(A) tail.

In some other embodiments, the enzyme that is capable of joining a 3'-tag to the 3'-termini of the sense RNA molecules that have the RNA sequence tag joined to their 5'-termini is an RNA-dependent DNA polymerase and the method additionally comprises the sub-steps of providing a second terminal tagging oligoribonucleotide and an RNA-dependent DNA polymerase; and, prior to step (H), incubating the sense RNA polymerase; molecules that have the RNA sequence tag joined to their 5'-termini with the second terminal tagging oligoribonucleotide and the RNA-dependent DNA polymerase under conditions and for sufficient time wherein the 3'-portion of the second terminal tagging oligoribonucleotide anneals to the 3'-terminal portion of the sense RNA molecules that have the RNA sequence tag joined to their 5'-termini and the 3'-termini of said sense RNA molecules that have the RNA sequence tag joined to their 5'-termini are extended by the RNA-dependent DNA polymerase using the 5'-portion of the second terminal tagging oligoribonucleotide as a template, thereby joining the 3'-tag to the 3'-termini of the sense RNA molecules that have the RNA sequence tag joined to their 5'-termini; in some of these embodiments, the method additionally comprises the sub-step of: inactivating the RNA-dependent DNA polymerase. In these embodiments, the 5'-portion of the second terminal tagging oligoribonucleotide exhibits a sequence that is different from the 5'-portion of the terminal tagging oligoribonucleotide provided in step (D) of the method. In some of these embodiments, the second-round first-strand cDNA synthesis primer exhibits a sequence in at least its 3'-terminal portion that is substantially the same as the sequence exhibited by the 5'-portion of the second terminal tagging oligoribonucleotide.

In other embodiments, wherein the portion of the first-strand cDNA molecules derived from the RNA first-strand cDNA synthesis primers is digested in step (C) of the method, the invention includes other embodiments for joining an annealing site for a second-round first-strand cDNA synthesis primer to the 3'-termini of the sense RNA molecules that have an RNA sequence tag joined to their 5'-termini. For example, but without limitation, in some embodiments, the sense RNA molecules that have an RNA sequence tag joined to their 5'-termini are incubated with the RNA-dependent DNA polymerase and the second terminal tagging oligoribonucleotide, under conditions and for sufficient time wherein a 3'-tag is joined to the 3'-termini of the sense RNA molecules that have an RNA sequence tag joined to their 5'-termini, which terminal tagging oligoribonucleotide: has a 5'-portion that is complementary to the sequence of a 3'-tag that it is desired to join to the 3'-termini of the sense RNA molecules that have an RNA sequence tag joined to their 5'-termini from step (F); has a 3'-portion that is capable of annealing to the 3'-terminal portion of said sense RNA molecules that have an RNA sequence tag joined to their 5'-termini; and has a 3'-terminal nucleotide that is not capable of being extended by a DNA polymerase.

In some preferred embodiments, the second-round first-strand cDNA synthesis primers provided in step (G) are the same as the RNA first-strand cDNA synthesis primers provided in step (A). In some preferred embodiments, the second-round first-strand cDNA synthesis primers provided in step (G) are identical to the RNA first-strand cDNA synthesis primers provided in step (A) of the first round of the method. In other embodiments, the second-round first-strand cDNA synthesis primers provided in step (G) exhibit the same sequences as the RNA first-strand cDNA synthesis primers provided in step (A), but the second-round first-strand cDNA synthesis primers consist of deoxyribonucleotides. In other embodiments, the second-round first-strand cDNA synthesis primers provided in step (G) exhibit sequences that are different from the sequences exhibited by the RNA first-strand cDNA synthesis primers provided in step (A); in some of these embodiments, the second-round first-strand cDNA synthesis primers consist of a deoxyribonucleotide rather than a ribonucleotide composition. In some embodiments, the second-round first-strand cDNA synthesis primers consist entirely or primarily of deoxyribonucleotides. In some embodiments, step (G) additionally comprises: providing a single-strand-specific DNase (e.g., exonuclease I; exonuclease VII; and/or Rec J exonuclease); and the method additionally comprises, after step (H), the sub-step of: contacting the reaction mixture with the single-strand-specific DNase under conditions and for sufficient time wherein the second-round first-strand cDNA synthesis primers are digested.

In some preferred embodiments, the second-round second-strand cDNA synthesis primer provided in step (G) is identical to the second-strand cDNA synthesis primer provided in step (A). In other embodiments, the second-round second-strand cDNA synthesis primer provided in step (G) is different from the second-strand cDNA synthesis primer provided in step (A). In some embodiments, the 5'-portion of the second-round second-strand cDNA synthesis primer provided in step (G) exhibits a different anti-sense promoter sequence from the sequence exhibited by the 5'-portion of the second-strand cDNA synthesis primer provided in step (A); in those embodiments, the second-round RNA polymerase provided in step (G) is one that recognizes and binds the RNA polymerase promoter for which the 5'-portion of the second-round second-strand cDNA synthesis primer exhibits an anti-sense promoter sequence.

In some preferred embodiments, the second-round RNA-dependent DNA polymerase provided in step (G) is the same as the RNA-dependent DNA polymerase provided in step (A). In some embodiments, the second-round RNA-dependent DNA polymerase provided in step (G) is different from the RNA-dependent DNA polymerase provided in step (A).

In some preferred embodiments, the second-round DNA-template-specific DNA polymerase provided in step (G) is the same as the DNA-template-specific DNA polymerase provided in step (A). In some embodiments, the second-round DNA-template-specific DNA polymerase provided in step (G) is different from the DNA-template-specific DNA polymerase provided in step (A).

In some preferred embodiments, the second-round RNA polymerase provided in step (G) is the same as the RNA polymerase provided in step (A). In some embodiments, the second-round RNA polymerase provided in step (G) is different from the RNA polymerase provided in step (A).

In embodiments of the method comprising step (D) in the first round of synthesis, the DNA-template-specific DNA polymerase and the terminal tagging oligoribonucleotide are not needed in the second or subsequent rounds since the sense RNA molecules synthesized in step (F) have the RNA sequence tag joined to their 5'-termini.

In some preferred embodiments, step (J) of the method further comprises the sub-step of: inactivating the DNA-template-specific DNA polymerase.

In some preferred embodiments, step (G) additionally comprises: providing an RNase H; step (I) additionally comprises the sub-step of: incubating the reaction mixture with the RNase H under conditions and for sufficient time wherein RNA that is annealed to DNA is degraded; after which, the method additionally comprises the sub-step of: inactivating the RNase H.

In some preferred embodiments, the RNase H used in the second-round is the same as the RNase H used in the first round of the method. In other embodiments, the RNase H used in the second-round is different from the RNase H used in the first round of the method.

Those with knowledge in the art will understand that this method for obtaining additional amplification of sense RNA molecules that exhibit sequences that are substantially the same as the sequence exhibited by RNA molecules of interest in the sample can be repeated for one or more additional rounds by using the sense RNA molecules that have the RNA sequence tag joined to their 5'-termini synthesized in each round for making additional rounds of first-strand cDNA molecules, double-stranded cDNA molecules, and additional sense RNA molecules that have the RNA sequence tag joined to their 5'-termini.

In some embodiments, an RNA first-strand cDNA synthesis primer that has a 5'-flap is used, wherein the 5'-flap is used to create an annealing site for another oligonucleotide or primer to accomplish an intended purpose. For example, but without limitation, in some embodiments, RNA first-strand cDNA synthesis primers that have a 5'-flap are used to synthesize double-stranded cDNA molecules wherein the second-strand cDNA molecules exhibit a sequence on their 3'-termini that is complementary to the sequence exhibited by the 5'-flap of the RNA first-strand cDNA synthesis primers. In some embodiments, the method additionally comprises amplifying the first-strand cDNA molecules or the double-stranded cDNA molecules by performing the polymerase chain reaction (PCR) using a first PCR primer that is complementary to a sequence exhibited by the DNA sequence tag that is joined to the 3'-termini of the first-strand cDNA molecules (e.g., using step (D) of the method) and a second PCR primer that exhibits a sequence that is identical to at least a portion of the sequence exhibited by the 5'-flap of the RNA first-strand cDNA synthesis primer. In some such embodiments, the first PCR primer also has a 5'-flap that exhibits an arbitrary sequence, which can be the same or different than the arbitrary sequence exhibited by the 5'-flap of the RNA first-strand cDNA synthesis primers. In some preferred embodiments, the first PCR primer has a 5'-flap that exhibits an anti-sense promoter sequence for an RNA polymerase promoter.

Modes of Performance and Additional Methods of the Invention

Depending on the application and its requirements and constraints, the methods of the invention can be performed in a stepwise fashion, with one set of reactions being performed, followed by purification of a reaction product or removal of reagents or inactivation of enzymes or addition of reagents before proceeding to the next set of reactions, or, in other embodiments for other applications, the steps of a method can be performed as a continuous set of multiple reactions in a single reaction mixture. By way of example, but not of limitation, in some embodiments, the reactions can be carried out in a single reaction mixture and the products of the reaction may be detected, without ever being isolated.

The invention also comprises parts or subsets of the methods and compositions of the invention. Thus, the invention comprises all of the individual steps of the methods of the invention that are enabled thereby, in addition to the overall methods.

Reaction Conditions for Steps of the Method

Appropriate reaction media and conditions for carrying out the methods of the present invention are those that permit in vitro RNA- and DNA-dependent DNA synthesis, transcription, and other reactions according to the methods of the present invention. With respect to transcription reactions of the invention with a wild-type or mutant T7 RNAP enzymes, in preferred embodiments, the reaction conditions for in vitro transcription are those provided with the AmpliScribe™ T7-Flash™ Transcription Kit, or the AmpliScribe™ T7 High Yield Transcription Kit, in each case according to the instructions of the manufacturer (EPICENTRE Biotechnologies, Madison, Wis.). If a T3 or SP6 RNAP is used, the reaction conditions for in vitro transcription are those provided with the AmpliScribe™ T3 High Yield Transcription Kit or with the AmpliScribe™ T3-Flash™ High Yield Transcription Kit, or with the AmpliScribe™ SP6 High Yield Transcription Kit (EPICENTRE Biotechnologies, Madison, Wis.). If mini-vR-NAP or mini-vRNAP Y678F enzymes are used in vitro transcription of a single-stranded DNA template having a single-stranded promoter, the following in vitro transcription reaction is prepared by setting up a reaction mixture containing the following final concentrations of components, added in the order given: 0.1 micromolar of a N4 vRNAP promoter-containing DNA oligo; 1.0 micromolar EcoSSB Protein; 1× transcription buffer comprising 40 mM Tris-HCl (pH 7.5), 6 mM $MgCl_2$, 2 mM spermidine, and 10 mM NaCl; 1 mM DTT; 0.5 mM of each NTP (ATP, CTP, GTP and UTP; and 0.1 micromolar of mini-vRNAP enzyme, and then incubated at about 37° C. Other modified nucleoside triphosphates can be used in place of or in addition to the canonical NTPs for specific applications. The reaction can be followed by gel electrophoresis on an agarose or PAGE gel. Reaction conditions for in vitro transcription using other RNA polymerases are well known in the art and can be obtained from the public literature. Those with skill in the art will know that other suitable reaction conditions under which an RNA polymerase of the invention can be used can be found by simple experimentation, and any of these reaction conditions are also included within the scope of the invention.

The invention is not limited to these reaction conditions or concentrations of reactants for in vitro transcription or for another enzymatic or other reaction used in the method. Such reaction mixtures and conditions are known to persons of skill in the art, and are described in various publications, such as U.S. Pat. No. 5,679,512 and PCT Publication No. WO99/42618. For example, a buffer can be Tris buffer, although other buffers can also be used as long as the buffer components are non-inhibitory to enzyme components of the methods of the invention. The pH is preferably from about 5 to about 11, more preferably from about 6 to about 10, even more preferably from about 7 to about 9, and most preferably from about 7.5 to about 8.5. The reaction mixture can also include bivalent metal ions such as $Mg^{+2}$ or $Mn^{+2}$, at a final concentration of free ions that is within the range of from about 0.01 to about 10 mM, and most preferably from about 1 to 6 mM. The reaction mixture can also include other salts, such as KCl, that contribute to the total ionic strength of the mixture. For example, the range of a salt such as KCl is preferably from about 0 to about 100 mM, more preferably from about 0 to about 75 mM, and most preferably from about 0 to about 50 mM. However, in some reactions, a higher or lower concentration of KCl is used. For example, in some preferred embodiments of step (B), wherein a RNA-dependent DNA polymerase comprising wild-type AMV reverse transcriptase is used, the KCl is preferably from about 75 mM to about 200 mM in the reaction mixture, and most preferably from about 100 mM to about 160 mM. The reaction mixture can further include additives that could affect performance of the reactions, but that are not integral to the activity of the enzyme components of the methods. Such additives include proteins such as BSA, and non-ionic detergents such as NP40 or Triton X100. Reagents, such as DTT, that are capable of maintaining activities of enzymes with sulfhydryl groups can also be included. Such reagents are known in the art. Where appropriate, an RNase inhibitor, such as, but not limited to ScriptGuard™ RNase Inhibitor (EPICENTRE Biotechnologies, Madison, Wis., USA), a placental ribonuclease inhibitor (e.g., RNasin®, Promega Corporation, Madison, Wis., USA), or an antibody RNase inhibitor, that does not inhibit the activity of an RNase employed in the method can also be included. Any aspect of the methods of the present invention can occur at the same or varying temperatures. In some preferred embodiments, the reactions are performed isothermally, which avoids the cumbersome thermocycling process. The reactions are carried out at temperatures that permit hybridization of complementary primers, oligonucleotides, or other nucleic acids during the steps of the methods of the present invention and that are optimal for activity (and that do not substantially inhibit the desired activity) of the enzymes employed. Temperatures are chosen which are optimal for each particular reaction of the method. In some embodiments, a reaction is incubated at a temperature in the range of about 20° C. to about 85° C. In some embodiments, a reaction is incubated at a temperature of about 20° C., about 30° C., about 40° C., about 50° C., or about 60° C. The temperatures of various reactions in one preferred embodiments of a method of the invention comprising steps (A) through (F) are presented in Example 5 herein. However, the invention is not limited to this example and other temperatures and reaction times can also be used for those reactions, or for other reactions that use different particular enzymes in the steps of the method. In general, optimal or near-optimal temperatures for an enzymatic or other reaction can be identified or easily determined based on information known in the art.

As disclosed in U.S. Pat. Nos. 6,048,696 and 6,030,814, as well as in German Patent No. DE4411588C1, it is preferred in some embodiments to use a final concentration of about 0.25 M, about 0.5 M, about 1.0 M, about 1.5 M, about 2.0 M, about 2.5 M or between about 0.25 M and 2.5 M betaine (trimethylglycine) in DNA polymerase or reverse transcriptase reactions in order to decrease DNA polymerase stops and increase the specificity of reactions which use a DNA polymerase.

Nucleotide and/or nucleotide analogs, such as deoxyribonucleoside triphosphates, that can be employed for synthesis of reverse transcription or primer extension products in the methods of the invention are provided in an amount that is determined to be optimal or useful for a particular intended use.

The oligonucleotide components of reactions of the invention are generally in excess of the number of RNA molecules of interest to be amplified. They can be provided at about or at least about any of the following: 2, 5, 10, $10^2$, $10^4$, $10^6$, $10^8$, $10^{10}$, $10^{12}$ times the amount of RNA molecules of interest in the sample. RNA first-strand cDNA synthesis primers, terminal tagging oligoribonucleotides, second-strand cDNA synthesis primers, and the like, can each be provided at about or at least about any of the following concentrations: 1 nM, 2 nM, 10 nM, 50 nM, 100 nM, 500 nM, 1250 nM, 2500 nM, 5000 nM, 10,000 nM, 20,000 nM, or, 50,000 nM, but higher or lower concentrations can also be used. By way of example, but not of limitation, a concentration of one or more oligonucleotides may be desirable for synthesizing multiple copies of sense RNA that exhibits substantially the same sequences as the one or more RNA molecules of interest. In some preferred embodiments wherein the one or more RNA molecules of interest comprise a multiplicity of all mRNA molecules in a sample comprising total RNA from a eukaryote (e.g., human, animal or plant cells), RNA first-strand cDNA synthesis primers (e.g., oligo$(U)_{20}$), terminal tagging oligoribonucleotides, and second-strand cDNA synthesis primers are each provided at a final concentration in each respective reaction mixture of about 1 micromolar to about 50 micromolar. However, the invention is not limited to a particular concentration of an oligonucleotide, so long as the concentration is effective in a particular method of the invention.

In some embodiments, the foregoing components are added simultaneously at the initiation of the process. In other embodiments, components are added in any order prior to or after appropriate time points during the process, as required and/or permitted by the reaction. Such time points can readily be identified by a person of skill in the art. The enzymes used for nucleic acid reactions according to the methods of the present invention are generally added to the reaction mixture following a step for denaturing the one or RNA molecules of interest in or from a sample, and/or following hybridization of primers and/or oligos in a reaction to a denatured single-stranded nucleic acid molecule to form a nucleic acid complex, as determined by their thermal stability and/or other considerations known to the person of skill in the art.

The reactions can be stopped at various time points, and resumed at a later time. The time points can readily be identified by a person of skill in the art. Methods for stopping the reactions are known in the art, including, for example, cooling the reaction mixture to a temperature that inhibits enzyme activity, or heating the reaction mixture to inactivate the enzyme activity. Methods for resuming the reactions are also known in the art, including, for example, raising the temperature of a reaction mixture that has been cooled to inhibit activity to a temperature that permits enzyme activity. In some embodiments, one or more of the components of the reactions is replenished prior to, at, or following the resumption of the reactions. Alternatively, the reaction can be allowed to proceed (i.e., from start to finish) without interruption.

Detection, Identification and Uses of First-Strand cDNA Molecules, Double-Stranded cDNA Molecules, and Sense RNA Molecules Synthesized Using the Method In some embodiments, the detection of the multiple copies of sense RNA product molecules is indicative of the presence, quantity, and/or relative quantity of the one or more RNA molecules of interest in the sample. Quantitative analysis, including analysis in real time, can also be performed in some embodiments. Direct and indirect detection methods (including quantification) are well known in the art. For example, by comparing the amount of product amplified from a test sample containing an unknown amount of one or more RNA molecules of interest to the product of a reference sample that has a known quantity of the one or more RNA molecules of interest, the amount of the one or more RNA molecules of interest in the test sample can be determined.

The methods of the present invention can also be extended to analysis of sequence alterations and sequencing of the sense RNA molecules. The amplified sense RNA molecules can be sequenced using any suitable procedure. In some preferred embodiments, the amplified sense RNA molecules are first coverted to single-stranded cDNA by reverse transcription prior to sequencing. Further, detection could be effected by, for example, examination of translation products from the one or more sense RNA product molecules.

In some preferred embodiments, the one or more sense RNA molecules are capped using a capping enzyme system and polyadenylated using a poly(A) polymerase, and the capped and polyadenylated molecules obtained are translated in vivo in a eukaryotic cell. In some preferred embodiments the capped and polyadenylated sense RNA molecules are translated in vivo in an antigen-presenting cell. In some preferred embodiments, the antigen-presenting cell is selected from the group consisting of a dendritic cell, a macrophage, an epithelial cell, or an artificially generated antigen-presenting cell from a human or an animal. In some preferred embodiments, the capped and polyadenylated sense RNA molecules are derived from RNA molecules of interest from a tumor cell, from a cell that is infected with a pathogen, or from a cell that has a pathological condition. In some preferred embodiments, both the antigen-presenting cell and the cell from which the RNA molecules of interest are obtained are from a human or animal patient with the tumor, pathogenic infection, or pathological condition. In some preferred embodiments, the capped and polyadenylated sense RNA molecules are translated in vivo in an embryonic stem cell or in an induced pluripotent cell from a human or animal. In some embodiments, the capped and polyadenylated sense RNA molecules are obtained using the methods of the invention for amplification of one or more RNA molecules from one or more differentiated human or animal cells, wherein the capped and polyadenylated sense RNA molecules are used to transfect an animal or human embryonic stem cell or induced pluripotent cell in order to induce differentiation by in vivo expression of one or more of the capped and polyadenylated sense RNA molecules in said embryonic stem cell or induced pluripotent cell in culture.

In some embodiments, the sense RNA molecules are translated in vitro in a cell-free system (e.g., a cell-free lysate, such as a reticulocyte cell lysate or a wheat germ lysate). In one embodiment, the cell-free lysate is a human reticulocyte cell lysate made from reticulocytes obtained from human stem cells.

In some embodiments, first-strand cDNA molecules, double-stranded cDNA molecules, and/or sense RNA molecules are synthesized in situ in cells or tissue in a tissue section using methods of the invention. Examples of ways to introduce the reagents for performing the steps of the method in situ are described in U.S. Pat. Nos. 5,168,038; 5,021,335; and 5,514,545. Thus, in some embodiments, the first-strand cDNA molecules are synthesized in a stepwise manner by contacting the cells or tissue in the tissue section under hybridizing conditions with the first-strand cDNA synthesis primer and other reagents and oligonucleotides, wherein the first-strand cDNA synthesis primer hybridizes to the one or more RNA molecules of interest in the sample comprising the cell or tissue, and the first-strand cDNA molecules, double-stranded cDNA molecules, and/or sense RNA molecules are synthesized using the steps of the method. By way of example, an RNA molecule of interest present in a sample can be cleaved in situ using a ribonuclease H in regions to which complementary oligonucleotides comprising at least three-to-four deoxynucleotides are annealed.

In embodiments in which the RNA molecules of interest comprise mRNA, whether of a single species of mRNA or all of the mRNA in a particular sample, the sense RNA molecules that are the transcription products can subsequently be used for a variety of applications. By way of example, but not of limitation, transcription products can be used for in vitro or in vivo translation, for use as RNAi to silence one or more genes in vivo, for spotting on a surface to make expression arrays or microarrays, or for making hybridization probes for arrays or microarrays for gene expression profiling or other uses. In still other embodiments, methods of the invention can be used to make first-strand cDNA molecules from mRNA, which in turn can be used for techniques such as random amplification of cDNA ends (RACE) or to make hybridization probes.

DEFINITIONS AND GENERAL ASPECTS OF THE INVENTION

If the same terms or similar terms have been used with different meaning by others, including those cited in the section entitled "Background to the Invention" herein, the terms when used to describe the present invention, shall nevertheless be interpreted to have the meanings presented below and in the sections related to the specification and claims, unless otherwise expressly stated to the contrary.

The terms "anneal" or "hybridize" and "annealing" or "hybridization" refer to the formation of complexes between nucleotide sequences that are sufficiently complementary to form complexes via Watson-Crick base pairing. With respect to the present invention, nucleic acid sequences that are "complementary to" or "complementary with" or that "hybridize" or "anneal" to or with each other should be capable of forming or form "hybrids" or "complexes" that are sufficiently stable to serve the intended purpose. It is not required that every nucleic acid base within a sequence exhibited by one nucleic acid molecule is capable of basepairing or is paired with or is complexed with every nucleic acid base within a sequence exhibited by a second nucleic acid molecule in order for the two nucleic acid molecules or the respective sequences exhibited therein to be "complementary" or "annealed" or "hybridized" to or with each other. By way of example, where a primer, such as a RNA first-strand cDNA synthesis primer, is complementary to, or hybridizes or anneals with an RNA molecule of interest in a sample, or an oligonucleotide, such as an terminal tagging oligoribonucleotide, is complementary to, or hybridizes or anneals with a first-strand cDNA molecule, respectively, each respective complex or hybrid should be sufficiently stable to serve the respective priming and/or template functions required (e.g., for a DNA polymerase to copy the RNA molecule of interest by extension of the complementary annealed RNA first-strand cDNA synthesis primer, or to extend the 3'-end of the first-strand cDNA molecule using a complementary annealed terminal tagging oligoribonucleotide, respectively, as a template.

In general, "cDNA" or a "cDNA molecule" refers to "complementary DNA" that is synthesized by RNA-dependent DNA polymerase- or reverse transcriptase-catalyzed extension of a primer that anneals to an RNA molecule of interest using at least a portion of the RNA molecule of interest as a template (which process is also called "reverse transcription"). The cDNA molecules synthesized are "homologous to" or "base pair with" or "form a complex with" at least a portion of the template. Most methods in the art comprise synthesis of double-stranded cDNA molecules.

"Double-stranded cDNA molecules" are obtained by synthesizing "second-strand cDNA molecules" or "second-strand cDNA" by DNA-template-specific DNA polymerase-catalyzed extension of "second-strand cDNA synthesis primers" that anneal to and use the first-strand cDNA molecules as templates.

The word "derived", such as for an RNA that is "derived" from a condition, biological sample, sample, tumor, pathogen, or the like, means that the RNA either was present in the condition, biological sample, sample, tumor, or pathogen, or was made using the RNA in the condition, biological sample, sample, tumor, or pathogen by a process such as, but not limited to, an RNA amplification reaction, wherein the RNA is either encoded by or a copy of all or a portion of the RNA molecules in the original condition, biological sample, sample, tumor, or pathogen. By way of example, but without limitation, such RNA can be from an in vitro transcription or an RNA amplification reaction, with or without cloning of cDNA, rather than being obtained directly from the condition, biological sample, sample, tumor, or pathogen, so long as the original RNA used for the in vitro transcription or an RNA amplification reaction was from the condition, biological sample, sample, tumor, or pathogen.

A "DNA-dependent DNA polymerase" or "DNA-template-specific DNA polymerase" is an enzyme that synthesizes a complementary DNA ("cDNA") copy by extension of a primer that is annealed to a DNA template. All known DNA-template-specific DNA polymerases require a complementary primer to initiate synthesis. It is known that under suitable conditions, some DNA-template-specific DNA polymerases may also synthesize (i.e., "reverse transcribe") a complementary DNA copy from an RNA template, a process that is also referred to as "reverse transcription," for which application the DNA polymerase can also be referred to as a "reverse transcriptase." Some DNA polymerases are able to displace the strand complementary to the template strand as a new DNA strand is synthesized by the polymerase. This process is called "strand displacement" and the DNA polymerases that have this activity are referred to herein as "strand-displacing DNA polymerases." The template for strand displacement DNA synthesis can be a linear or circular ssDNA. If the DNA template is a single-stranded circle, primed DNA synthesis procedes around and around the circle, with continual displacement of the strand ahead of the replicating strand, a process called "rolling circle replication." Rolling circle replication results in synthesis of tandem copies of the circular template. In general, it is preferred that a DNA-template-specific DNA polymerase used for a method of the invention efficiently synthesizes DNA of a suitable length for the intended purpose without "falling off" of the template (or terminating synthesis of the DNA), which is referred to as the enzyme's processivity. The capability of a DNA polymerase to strand displace can be readily determined using the polymerase in a rolling circle replication assay as described by Fire and Xu (Proc. Natl. Acad. Sci. USA 92:4641-4645, 1995. Strand displacement and DNA polymerase processivity can also be assayed using methods described in Kong et al. (J. Biol. Chem. 268:1965-1975). In general, a DNA-template-specific DNA polymerase used for a method of the invention lacks 5'-to-3' exonuclease activity. In some embodiments, a DNA-template-specific DNA polymerase used for a method of the invention has 3'-to-5' exonuclease activity, which can improve fidelity of the enzyme (i.e., it synthesizes DNA with fewer nucleotides that are not complementary to the template). However, in other embodiments, the DNA-template-specific DNA polymerase used for the method lacks 3'-to-5' exonuclease activity. Fidelity and/or error rates of many DNA polymerases under particular conditions are known, as are methods for measuring fidelity (e.g., by sequencing).

A "first-strand cDNA molecule" or a "first-strand cDNA primer extension product," when used herein, means the product obtained by primer extension of a first-strand cDNA synthesis primer, such as, but not limited to, an RNA first-strand cDNA synthesis primer, by the RNA-dependent DNA polymerase using an RNA molecule of interest as a template.

"First-strand cDNA synthesis primers," when used herein, means the primers used for synthesis of first-strand cDNA molecules by primer extension using an RNA-dependent DNA polymerase or a reverse transcriptase and RNA as a template. When used herein, "RNA first-strand cDNA synthesis primers" mean first-strand cDNA synthesis primers comprising ribonucleotides that are capable of being extended by the RNA-dependent DNA polymerase using RNA as a template. In preferred embodiments, RNA first-strand cDNA synthesis primers, upon being digested by a suitable single-strand-specific RNase, are converted to mononucleotides or short oligonucleotides that are not capable of being extended by the RNA-dependent DNA polymerase under the conditions used in the method.

"In vitro" refers to an artificial environment and to processes or reactions that occur within an artificial environment.

In vitro environments can consist of, but are not limited to, processes or reactions that occur in a test tube. The term "in vivo" refers to the natural environment and to processes or reactions that occur within a natural environment (e.g., in an animal or a cell).

"Nucleic Acids," "Polynucleotides" and "Oligonucleotides" Used in the Method

A "nucleic acid" or "polynucleotide" of the invention is a polymer molecule comprising a series of "mononucleosides," also referred to as "nucleosides," in which the 3'-position of the pentose sugar of one nucleoside is linked by an internucleoside linkage, such as, but not limited to, a phosphodiester bond, to the 5'-position of the pentose sugar of the next nucleoside. A nucleoside linked to a phosphate group is referred to as a "nucleotide." The nucleotide that is linked to the 5'-position of the next nucleotide in the series is referred to as "5' of" or the "5'nucleotide" and the nucleotide that is linked to the 3'-position of the 5' nucleotide is referred to as "3' of" or the "3' nucleotide." The terms "3'- of" and "5'- of" are used herein with respect to the present invention to refer to the position or orientation of a particular nucleic acid sequence or genetic element, such as, but not limited to, an RNA polymerase promoter (or the anti-sense promoter sequence or the sense promoter sequence exhibited by the RNA polymerase promoter), relative to other sequences or genetic elements within the DNA or RNA strand of the particular nucleic acid, polynucleotide, or oligonucleotide being discussed. Thus, although the synthesis of RNA in a 5'-to-3' direction during transcription is thought of as proceeding in a "downstream" direction, the sense promoter sequence exhibited by an RNA polymerase promoter is referred to herein as being 3'- of the transcribed template sequence on the template strand. Those with knowledge in the art will understand these terms in the context of nucleic acid chemistry and structure, particularly related to the 3'- and 5'-positions of sugar moieties of canonical nucleic acid nucleotides. By way of further example, an anti-sense promoter sequence that is "5'- of another sequence" in a second-strand cDNA synthesis primer refers to an anti-sense promoter sequence that is exhibited at or closer to the 5'-terminus of the second-strand cDNA synthesis primer relative to the other sequence. If a first nucleic acid sequence is 3'- of a second sequence on one strand, the complement of the first sequence will be 5'- of the complement of the second sequence on the complementary strand. The description of the invention will be understood with respect to the relative 5' or 3' position and orientation of a sequence or genetic element within a particular nucleic acid strand, unless explicitly stated to the contrary.

The pentose sugar of the nucleic acid can be ribose, in which case, the nucleic acid or polynucleotide is referred to as "RNA," or it can be 2'-deoxyribose, in which case, the nucleic acid or polynucleotide is referred to as "DNA." Alternatively, especially if the nucleic acid is synthesized chemically, the nucleic acid can be composed of both DNA and RNA mononucleotides. In both RNA and DNA, each pentose sugar is covalently linked to one of four common or "canonical" nucleic acid bases (each also referred to as a "base"). Three of the predominant naturally-occurring bases that are linked to the sugars (adenine, cytidine and guanine) are common for both DNA and RNA, while one base is different; DNA has the additional base thymine, while RNA has the additional base uridine. In some cases, uridine can be present as a base in DNA. Those in the art commonly think of a small polynucleotide as an "oligonucleotide." The term "oligonucleotide" as used herein is defined as a molecule comprising of two or more deoxyribonucleotides or ribonucleotides, preferably about 6 to 100 nucleotides, but there is no defined limit to the length of an oligonucleotide. The exact size will depend on many factors, which in turn depends on the ultimate function or use of the oligonucleotide.

Also, for a variety of reasons, a nucleic acid or polynucleotide of the invention may comprise one or more modified nucleic acid bases, sugar moieties, or internucleoside linkages. By way of example, some reasons for using nucleic acids or polynucleotides that contain modified bases, sugar moieties, or internucleoside linkages include, but are not limited to: (1) modification of the $T_m$; (2) changing the susceptibility of the polynucleotide to one or more nucleases; (3) providing a moiety for attachment of a label; (4) providing a label or a quencher for a label; or (5) providing a moiety, such as biotin, for attaching to another molecule which is in solution or bound to a surface. For example, in some embodiments, an oligonucleotide, such as the terminal tagging oligoribonucleotide, may be synthesized so that the random 3'-portion contains one or more conformationally restricted ribonucleic acid analogs, such as, but not limited to one or more ribonucleic acid analogs in which the ribose ring is "locked" with a methylene bridge connecting the 2'-O atom with the 4'-C atom (e.g., as available from Exiqon, Inc. under the trademark of "LNA™"); these modified nucleotides result in an increase in the $T_m$ or melting temperature by about 2 degrees to about 8 degrees centigrade per nucleotide monomer. If the $T_m$ is increased, it might be possible to reduce the number of random nucleotides in the random 3'-portion of the terminal tagging oligoribonucleotide. However, a modified nucleotide, such as an LNA must be validated to function in the method for its intended purpose, as well as satisfying other criteria of the method; for example, in some embodiments, one criterium for using the modified nucleotide in the method is that the oligonucleotide that contains it can be digested by a single-strand-specific RNase.

In order to accomplish the goals of the invention, by way of example, but not of limitation, the nucleic acid bases in the mononucleotides may comprise guanine, adenine, uracil, thymine, or cytidine, or alternatively, one or more of the nucleic acid bases may comprise a modified base, such as, but not limited to xanthine, allyamino-uracil, allyamino-thymidine, hypoxanthine, 2-aminoadenine, 5-propynyl uracil, 5-propynyl cytosine, 4-thiouracil, 6-thioguanine, aza and deaza uracils, thymidines, cytosines, adenines, or guanines. Still further, they may comprise a nucleic acid base that is derivatized with a biotin moiety, a digoxigenin moiety, a fluorescent or chemiluminescent moiety, a quenching moiety or some other moiety. The invention is not limited to the nucleic acid bases listed; this list is given to show an example of the broad range of bases which may be used for a particular purpose in a method.

With respect to nucleic acids or polynucleotides of the invention, one or more of the sugar moieties can comprise ribose or 2'-deoxyribose, or alternatively, one or more of the sugar moieties can be some other sugar moiety, such as, but not limited to, 2'-fluoro-2'-deoxyribose or 2'-O-methyl-ribose, which provide resistance to some nucleases, or 2'-amino-2'-deoxyribose or 2'-azido-2'-deoxyribose, which can be labeled by reacting them with visible, fluorescent, infrared fluorescent or other detectable dyes or chemicals having an electrophilic, photoreactive, alkynyl, or other reactive chemical moiety.

The internucleoside linkages of nucleic acids or polynucleotides of the invention can be phosphodiester linkages, or alternatively, one or more of the internucleoside linkages can comprise modified linkages, such as, but not limited to, phosphorothioate, phosphorodithioate, phosphoroselenate, or phosphorodiselenate linkages, which are resistant to some nucleases Oligonucleotides and polynucleotides, including chimeric (i.e., composite) molecules and oligonucleotides with modified bases, sugars, or internucleoside linkages are commercially available (e.g., TriLink Biotechnologies, San Diego, Calif., USA or Integrated DNA Technologies, Coralville, Iowa).

"Poly(A) polymerase" ("PAP"), when used herein, means a template-independent RNA polymerase found in most eukaryotes, prokaryotes, and eukaryotic viruses that selectively uses ATP to incorporate AMP residues to 3'-hydroxylated ends of RNA. Since PAP enzymes that have been studied from plants, animals, bacteria and viruses all catalyze the same overall reaction (e.g., see Edmonds, M, Methods Enzymol., 181; 161-180, 1990), are highly conserved structurally (e.g., see Gershon, P, Nature Structural Biol. 7: 819-821, 2000), and lack intrinsic specificity for particular sequences or sizes of RNA molecules if the PAP is separated from proteins that recognize AAUAAA polyadenylation signals (Wilusz, J and Shenk, T, Cell 52: 221, 1988), purified wild-type and recombinant PAP enzymes from any of a variety of sources can be used in the kits and methods of the present invention.

A "portion" or "region," used interchangeably herein, of a polynucleotide or oligonucleotide (including a primer) is a contiguous sequence of 2 or more bases. In other embodiments, a region or portion is at least about any of 1, 2, 3, 5, 10, 15, 20, 25, 50, 75, or even more contiguous nucleotides.

A "primer" is an oligonucleotide ("oligo"), generally with a free 3'-OH group, for which at least the 3'-portion of the oligo is complementary to a portion of a template nucleic acid, and which oligo "binds" (or "complexes," "anneals," or "hybridizes"), by hydrogen bonding and other molecular forces, to the template to give a primer/template complex for initiation of synthesis by a DNA polymerase, and which is extended (i.e., "primer extended") by the addition of covalently bonded bases linked at its 3'-end which are complementary to the template in the process of DNA synthesis. The result is a primer extension product. Template-dependent DNA polymerases (including reverse transcriptases) generally require complexing of an oligonucleotide primer to a single-stranded template to initiate DNA synthesis ("priming"), but RNA polymerases generally do not require a primer for synthesis of RNA that is complementary to a DNA template (transcription).

The term "purified" or "to purify" herein refers to the removal of components (e.g., contaminants) from a sample. For example, nucleic acids are purified by removal of contaminating cellular proteins or other undesired nucleic acid species. The removal of contaminants results in an increase in the percentage of desired nucleic acid in the sample.

As used herein, "RNase H" or "ribonuclease H" means a ribonuclease enzyme that degrades the RNA portion of an RNA:DNA duplex. An RNase H can be an endonuclease or an exonuclease. Most wild-type reverse transcriptase enzymes have an RNase H activity in addition to their polymerase activity. Other sources of the RNase H are available without an associated polymerase activity.

An "RNA amplification reaction" or an "RNA amplification method" means a method for increasing the amount of RNA corresponding to one or multiple desired RNA sequences in a sample. For example, in some embodiments, the RNA amplification method comprises: (a) synthesizing first-strand cDNA molecules complementary to the one or more desired RNA molecules by RNA-dependent DNA polymerase extension of one or more primers that anneal to the RNA molecules; (b) synthesizing double-stranded cDNA molecules from the first-strand cDNA molecules using a process wherein a functional RNA polymerase promoter is joined thereto; and (c) contacting the double-stranded cDNA with an RNA polymerase that binds to said RNA polymerase promoter under transcription conditions whereby RNA corresponding to the one or more RNA molecules is synthesized. Unless otherwise stated related to a specific embodiment of the invention, an RNA amplification reaction according to the present invention means a sense RNA amplification reaction, meaning an RNA amplification reaction that synthesizes sense RNA (e.g., RNA having the same sequence as an mRNA or other primary RNA transcript, rather than the complement of that sequence). Sense RNA amplification reactions known in the art, which are encompassed within this definition include, but are not limited to, the methods which synthesize sense RNA described in U.S. Patent Application No. 20050153333 of Sooknanan; U.S. Patent Application No. 20030186237 of Ginsberg, Stephen; U.S. Patent Application No. 20040197802 of Dahl and Jendrisak; U.S. Patent Application Nos. 20060281153; 20070048741; and 20070105124 of Getts, et al.; U.S. Patent Application No. 20040171041 of Dahl et al.; and in Ozawa, T et al. (Biotechniques 40: 469-478, 2006).

An "RNA-dependent DNA polymerase" or "reverse transcriptase" is an enzyme that is capable of extending the 3'-end of a nucleic acid that is annealed to an RNA template to synthesize DNA that is complementary to the template ("complementary DNA" or "cDNA"). The 3'-end of the nucleic acid that is extended can be the 3'-end of the same RNA template, in which case cDNA synthesis is primed intramolecularly, or the 3'-end of the nucleic acid that is extended can be the 3'-end of another nucleic acid that is different from the RNA template and that is annealed to the RNA template, in which case cDNA synthesis is primed intermolecularly. All known reverse transcriptases also have the ability to make a complementary DNA copy from a DNA template; thus, they are both RNA- and DNA-dependent DNA polymerases.

An "RNA polymerase promoter" or "promoter," as used herein, means a segment of DNA that exhibits a nucleotide sequence to which an RNA polymerase that recognizes said sequence is capable of binding and initiating synthesis of RNA. Most, but not all, RNA polymerase promoters are double-stranded. If an RNA polymerase promoter is double-stranded, the RNA polymerase promoter exhibits (or has) a "sense promoter sequence" and an "anti-sense promoter sequence." As used herein, the "sense promoter sequence" is defined as the sequence of an RNA polymerase promoter that is joined to the template strand, in which case the sense promoter sequence is 3'- of the DNA sequence in the template strand that serves to specify the sequence of nucleotides exhibited by the RNA that is synthesized by the RNA polymerase that recognizes and binds to the RNA polymerase promoter. As used herein, the "anti-sense promoter sequence" is defined as the sequence of an RNA polymerase promoter that is complementary to the sense promoter sequence. If an RNA polymerase (e.g., phage N4 RNA polymerase) can synthesize RNA using a single-stranded RNA polymerase promoter, then the RNA polymerase promoter exhibits only the sense promoter sequence. It should be noted that the definitions of a "sense promoter sequence" and "anti-sense promoter sequence" may be the opposite of what would be expected by some people with knowledge in the art, but the terminology used herein was developed in the relatively new context of single-stranded RNA polymerase promoters. It is more easily understood and remembered by noting that a sense promoter sequence in the template strand (i.e., joined to the 3'-termini of the first-strand cDNA molecules) results in synthesis of sense RNA using the methods of the invention.

An RNA polymerase "pseudopromoter" or "synthetic promoter" of the present invention means a single-stranded sequence that is identified and/or selected to be functional as a promoter for in vitro transcription by an RNA polymerase that binds the promoter with specificity and functions as a promoter for the RNA polymerase in a transcription reaction. If a nucleic acid that contains a pseudopromoter or synthetic promoter is used in the method of the invention, then the corresponding RNA polymerase for which the pseudopromoter or synthetic promoter was identified and/or selected is used in the method. By way of example, but not of limitation, a sense promoter comprising a ssDNA pseudopromoter can be obtained as described by Ohmichi et al. (Proc. Natl. Acad. Sci. USA 99:54-59, 2002) and used as a sense promoter in a composition of a method of the invention that uses E. coli RNAP or a T7-type phage RNAP.

As used herein, a "single-strand-specific DNase" means a DNase that specifically digests single-stranded DNA, but that does not digest single-stranded RNA or RNA or DNA that is annealed to or complexed with complementary RNA or DNA, whether said complementary RNA or DNA is part of another nucleic acid molecule (e.g., by intermolecular base-pairing) or a portion of the same nucleic acid molecule (e.g., by intramolecular base-pairing). The single-strand-specific DNase can be an endonuclease or an exonuclease, so long as it is active in specifically digesting single-stranded DNA to monomers or short oligodeoxyribonucleotides. In preferred embodiments, the products of digestion using the single-strand-specific DNase do not serve as primers in the presence of a single-stranded nucleic acid molecule that is capable of serving as a template under the reaction conditions used in the method. Exonuclease I, exonuclease VII, and Rec J exonuclease are exemplary single-strand-specific DNases.

As used herein, a "single-strand-specific RNase" means an RNase that specifically digests single-stranded RNA, but that does not digest single-stranded DNA or RNA or DNA that is annealed to or complexed with complementary RNA or DNA, whether said complementary RNA or DNA is part of another nucleic acid molecule (e.g., by intermolecular base-pairing) or a portion of the same nucleic acid molecule (e.g., by intramolecular basepairing). The single-strand-specific RNase can be an endonuclease or an exonuclease, so long as it is active in specifically digesting single-stranded RNA to monomers or short oligoribonucleotides that do not serve as primers in the presence of a single-stranded nucleic acid molecule that is capable of serving as a template under the reaction conditions used in the method. E. coli RNase I is an exemplary single-strand-specific RNase.

A "T7-type RNA polymerase" (RNAP) herein means T7 RNA polymerase (e.g., see Studier, F W et al., pp. 60-89 in Methods in Enzymology, Vol. 185, ed. by Goeddel, D V, Academic Press, 1990) or an RNAP derived from a "T7-type" bacteriophage, meaning a bacteriophage that has a similar genetic organization to that of bacteriophage T7. The genetic organization of all T7-type phages that have been examined has been found to be essentially the same as that of T7. Examples of T7-type bacteriophages according to the invention include, but are not limited to *Escherichia coli* phages T3, phi I, phi II, W31, H, Y, A1, 122, cro, C21, C22, and C23; *Pseudomonas putida* phage gh-1; *Salmonella typhimurium* phage SP6; *Serratia marcescens* phages IV; *Citrobacter* phage ViIII; and *Klebsiella* phage No. 11 (Hausmann, Current Topics in Microbiology and Immunology 75:77-109, 1976; Korsten et al., J. Gen. Virol. 43:57-73, 1975; Dunn, et al., Nature New Biology 230:94-96, 1971; Towle, et al., J. Biol. Chem. 250:1723-1733, 1975; Butler and Chamberlin, J. Biol. Chem. 257:5772-5778, 1982), as well as mutant forms of such RNAPs (e.g., Sousa et al., U.S. Pat. No. 5,849,546; Padilla, R and Sousa, R, Nucleic Acids Res., 15: e138, 2002; Sousa, R and Mukherjee, S, Prog Nucleic Acid Res Mol Biol., 73: 1-41, 2003; Guillerez, J, et al., U.S. Patent Application No. 20040091854).

A "template" is a nucleic acid molecule that serves to specify the sequence of nucleotides exhibited by a nucleic that is synthesized by a DNA-dependent or RNA-dependent nucleic acid polymerase. If the nucleic acid comprises two strands (i.e., is "double-stranded"), and sometimes even if the nucleic acid comprises only one strand (i.e., is "single-stranded"), the strand that serves to specify the sequence of nucleotides exhibited by a nucleic that is synthesized is the "template" or "the template strand." The nucleic acid synthesized by the nucleic acid polymerase is complementary to the template. Both RNA and DNA are always synthesized in the 5'-to-3' direction, beginning at the 3'-end of the template strand, and the two strands of a nucleic acid duplex always are aligned so that the 5' ends of the two strands are at opposite ends of the duplex (and, by necessity, so then are the 3' ends). A primer is required for both RNA and DNA templates to initiate synthesis by a DNA polymerase, but a primer is not required to initiate synthesis by a DNA-dependent RNA polymerase, which is usually called simply an "RNA polymerase."

"Terminal transferase", also referred to as "terminal deoxyribonucleotidyl transferase" or "TdT", is a DNA polymerase that catalyzes template-independent addition (or "tailing") of deoxyribonucleoside triphosphates (dNTPs) or a single dideoxyribonucleoside triphosphate to the 3'-hydroxyl termini of DNA. A common terminal transferase used in the art, which is commercially available, is produced in an E. coli strain that expresses the recombinant gene from calf thymus.

"Transcription" means the formation or synthesis of an RNA molecule by an RNA polymerase using a DNA molecule as a template.

EXAMPLES

The following examples are provided in order to demonstrate and further illustrate certain preferred embodiments and aspects of the present invention and are not to be construed as limiting the scope thereof.

Example 1

Amplified Sense RNA Molecules Produced Using a First-Strand cDNA Synthesis Primer (oligo($dT_{20}V$)) and a Terminal Tagging Oligonucleotide Consisting of Deoxyribonucleotides (dTTO), without Purification Steps Prior to In Vitro Transcription (IVT)

Total RNA (100 ng) from HeLa cells (Clontech) was used as template to synthesize first-strand cDNA molecules in a standard first-strand cDNA synthesis reaction containing 50 pmoles of first-strand cDNA synthesis primer (Seq. ID. No. 1): ($dT_{20}V$), 5 mM Tris-HCl (pH 8.3), 10 mM $MgCl_2$, 75 mM KCl, 5 mM DTT, 1 mM dATP, 1 mM dGTP, 1 mM dCTP, 1 mM TTP and 25 units MMLV reverse transcriptase (EPICENTRE Biotechnologies) in a final volume of 5 μL. Corresponding reactions, but with no total RNA template (no template controls), were also included. The reactions were incubated at 37° C. for 60 minutes for first-strand cDNA synthesis. The RNA templates were then removed by enzymatic digestion with RNase H and RNase I simultaneously at 30° C. for 15 min. The two RNases were then inactivated by incubating at 95° C. for 5 min.

Next, a 2.5 µL terminal tagging mixture comprising 250 pmoles of the deoxyribonucleotide terminal tagging oligonucleotide (dTTO; Seq. ID. No. 2):

```
GACGAAGACAGTAGACAN6(N(2'-O-methyl))(3'-O-propyl-phosphate),
```

DTT (7.5 mM final concentration), and 25 units MMLV reverse transcriptase to each reaction at 37° C. The reactions were incubated at 37° C. for 30 min followed by 95° C. for 5 min. One set of template and no-template reactions was then purified using Minelute PCR purification columns (Qiagen, Mississauga, ON) while, the other set was used directly for second-strand cDNA synthesis.

The samples that were purified were then reconstituted in the equivalent reaction mixtures to those used prior to purification with the exception of the first-strand cDNA synthesis primer and the terminal tagging oligonulcleotide and MMLV RT, and placed at 37° C. along with the unpurified samples. Next, a 2.5 µL second-strand cDNA synthesis reaction mixture, comprising 20 pmoles of the second-strand cDNA synthesis primer (P3; Seq. ID. No. 3):

```
AATTCTAATACGACTCACTATAGGGAGACGAAGACAGTAGACA,
```

DTT (5 mM final concentration) and 25 units MMLV RT, was added to each reaction. Incubation was performed at 37° C. for 30 min followed by 80° C. for 3 min to inactivate the MMLV RT.

Only those samples that were previously purified after terminal tagging were again purified using Minelute PCR purification columns (Qiagen, Mississauga, ON) and eluted in 10 µL RNase-free water. The purified and unpurified samples were placed at 42° C. and a 40 µL of in vitro transcription (IVT) mixture comprising 1× AmpliScribe T7-Flash™ reaction buffer (EPICENTRE Biotechnologies), 9 mM ATP, 9 mM CTP, 9 mM GTP, 9 mM UTP and AmpliScribe T7-Flash™ RNA polymerase (EPICENTRE Biotechnologies) was added to each and incubated for 4 hours. Following in vitro transcription, 2 µL pancreatic RNase-free DNase I was added to each reaction and incubated at 37° C. for 15 min. The DNase I digestion step is optional if the entire reaction is to be used directly for second-round amplification. The amplified RNA from each was purified using Illustra™ RNAspin mini RNA isolation columns (GE Healthcare, Baie d'Urfé, QC) and the concentration determined at $A260_{nm}$.

The following 1-round terminal tagging/IVT reactions were performed:

1) 100 ng HeLa RNA template with two purification steps prior to IVT
2) no template with two purification steps prior to IVT
3) 100 ng HeLa RNA template with no purification step prior to IVT
4) no template with no purification step prior to IVT The first-round reactions yielded 1.4 µg, 0.2 µg, 1.3 µg, and 1.3 µg IVT-amplified sense RNA, respectively. An equal aliquot representing 25% of each transcription reaction was analyzed by ethidium bromide stained agarose gel electrophoresis.

FIG. 7, Lane 1 shows the IVT-amplified sense RNA from 100 ng HeLa RNA template with two purification steps prior to IVT, Lane 2 shows the IVT-amplified sense RNA from no template with two purification steps prior to IVT, Lane 3 shows the IVT-amplified sense RNA from 100 ng HeLa RNA template with no purification steps prior to IVT and Lane 4 shows the IVT-amplified sense RNA from no template with no purification steps prior to IVT. In addition to the template-specific products in Lane 1, there was a lower molecular weight product that was also observed in the no template reaction (Lane 2). Nevertheless, there was marked difference between the template-specific and no template reactions. On the other hand, both the template and no template reactions that did not include any purification steps prior to IVT gave very similar products with no discernible difference between the two (Lanes 3 and 4). These results suggest that the purification steps prior to IVT were important in helping to remove primer-related secondary products that would otherwise impeded the specific reaction and increase the non-specific background.

FIG. 7 contains the following:
Lane 1—10 µL of 1-round IVT-amplified sense RNA from the 100 ng HeLa RNA template reaction with two purification steps prior to IVT
Lane 2—10 µL of 1-round IVT-amplified sense RNA from the no template reaction with two purification steps prior to IVT
Lane 3—10 µL of 1-round IVT-amplified sense RNA from the 100 ng HeLa RNA template reaction with no purification step prior to IVT
Lane 4—10 µL of 1-round IVT-amplified sense RNA from the no template reaction with no purification step prior to IVT Example 2

Amplified Sense RNA Molecules Synthesized after 2-Rounds Using a First-Strand cDNA Synthesis Primers (dT) and Terminal Tagging Oligonucleotide Consisting of Deoxyribonucleotides (dTTO) and Mini-Column Purification Steps Prior to Synthesis of Sense RNA Molecules in the First Round of In Vitro Transcription An aliquot (20%) of the first-round IVT-amplified sense RNA molecules synthesized using each template and no-template control, corresponding to reactions #1 and #2, respectively, of Example 1, were used for 2-round IVT-amplification. Since the samples that were not purified in Example 1 contained predominantly non-specific products, they were not used for 2-round IVT-amplification. Each first-round-amplified RNA sample chosen for second-round amplification was used to synthesize first-strand cDNA molecules in a standard first-strand cDNA synthesis reaction containing 50 pmoles oligo($dT_{20}$)V first-strand cDNA synthesis primer (Seq. ID. No. 1; ($dT_{20}$)V), 5 mM Tris-HCl (pH 8.3), 10 mM $MgCl_2$, 50 mM KCl, 5 mM DTT, 1 mM dATP, 1 mM dGTP, 1 mM dCTP, 1 mM TTP and 25 units MMLV reverse transcriptase in a final volume of 5 µL. The reactions were incubated at 37° C. for 60 minutes for first-strand cDNA synthesis. The RNA templates were then removed by enzymatic digestion with RNase H and RNase I simultaneously at 30° C. for 15 min. The two RNases were then inactivated by incubating at 95° C. for 5 min.

Using a second-strand cDNA synthesis primer that was complementary to the DNA sequence tag joined to the 3'-termini of the first-strand cDNA molecules synthesized from the first-round amplified RNA, second-strand cDNA synthesis was performed by adding a 2.5 µL second-strand cDNA synthesis reaction mixture, comprising 20 pmoles of the second-strand cDNA synthesis primer (P3: Seq. ID. No. 3):

AATTCTAATACGACTCACTATAGGGAGACGAAGACAGTAGACA,

DTT (5 mM final concentration) and 25 units MMLV RT, to each reaction. Incubation was performed at 37° C. for 30 min followed by 80° C. for 3 min to inactivate the MMLV RT.

All samples were then purified using Minelute PCR purification columns (Qiagen, Mississauga, ON) and eluted in 10 µL RNase-free water. The purified samples were placed at 42° C. and a 40 µL in vitro transcription (IVT) mixture, comprising 1× AmpliScribe T7-Flash™ reaction buffer (EPICENTRE Biotechnologies), 9 mM ATP, 9 mM CTP, 9 mM GTP, 9 mM UTP and AmpliScribe T7-Flash™ RNA polymerase (EPICENTRE Biotechnologies) was added to each and incubated for 4 hours. Following IVT, 2 µL pancreatic RNase-free DNase I was added to each reaction and incubated at 37° C. for 15 min. The amplified RNA from each was purified using an Illustra™ RNAspin mini RNA isolation column (GE Healthcare, Baie d'Urfé, QC) and the concentration determined at A260$_{nm}$. The amplified RNA yields for the template and no template second-round reactions were 100 µg and 12.9 µg, respectively.

A 300-ng aliquot of sense RNA molecules obtained from each second-round IVT-amplification reaction was analyzed by ethidium bromide stained agarose gel electrophoresis.

FIG. 8, Lane 1 and Lane 2 show the second-round IVT-amplified sense RNA molecules produced using the sense RNA molecules from first-round reaction (reaction #1) and from the no-template reaction (reaction #2), respectively, as the RNA molecules of interest. It is evident from FIG. 8 that the no-template reaction (Lane 2) now contained higher molecular weight products in addition to the lower molecular weight products seen in the first-round (FIG. 7, Lane 2). Similar high molecular weight products were also seen in reaction #1, which used the sense RNA molecules from the first-round as templates for the second round (Lane 1). Nevertheless, the amount of amplified sense RNA molecules synthesized in reaction #1 was at least 7-fold higher than the no-template reaction, indicating that a majority of the product was template-dependent, rather than template-independent background.

FIG. 8 contains the following:

Lane 1—300 ng of second-round amplified RNA from the first-round template reaction with two purification steps prior to IVT Lane 2—300 ng of second-round amplified RNA from the first-round no template reaction with two purification steps prior to IVT Example 3

Amplified Sense RNA Molecules Synthesized after 2-Rounds Using a First-Strand cDNA Synthesis Primer (dT$_{20}$)V) Consisting of Deoxyribonucleotides and an Terminal Tagging Oligoribonucleotide Consisting of Ribonucleotides (rTTO) and Either 1 or 2 Mini-Column Purification Steps Prior to Synthesis of Sense RNA Molecules in the First Round of In Vitro Transcription Four first-strand cDNA synthesis reactions (2× template and 2× no-template) were performed as described in Example 1 with the exception that 5 ng of HeLa total RNA template was used in the appropriate reactions. The terminal tagging reactions were also performed as in Example 1 but with the following exceptions: (1) a terminal tagging oligoribonucleotide comprising ribonucleotides (rTTO; Seq. ID. No. 4):

GACGAAGACAGUAGACAN$_6$(N(2'-O-methyl))(3'-O-propyl-phosphate) was used instead of the terminal tagging oligonucleotide comprising deoxyribonucleotides (dTTO) and (2), one set of template and no-template reactions corresponding to reactions #3 and #4 were purified following the terminal tagging step using Minelute PCR purification columns (Qiagen, Mississauga, ON). Prior to the mini-column purification, the purified first-strand cDNA molecules that have a DNA sequence tag joined to their 3'-termini were reconstituted in the first-strand cDNA synthesis reaction mixture that lacked the first-strand cDNA synthesis primers, the terminal tagging oligoribonucleotide and MMLV RT.

The samples were heated to 95° C. for 5 min and placed then at 37° C. along with the unpurified samples. Then, the second-strand DNA synthesis reactions were performed exactly as described in Example 1.

All four samples were then purified using Minelute PCR purification columns (Qiagen, Mississauga, ON) and reconstituted in 10 µL RNase-free water. In vitro transcription (IVT) reactions were performed exactly as described in Example 1. The samples were then purified using Minelute RNA purification columns (Qiagen, Mississauga, ON) without DNase I digestion.

The following 1-round terminal tagging/IVT reactions were performed:

1) 100 ng HeLa RNA template with one purification step prior to IVT 2) no template with one purification step prior to IVT 3) 100 ng HeLa RNA template with two purification steps prior to IVT 4) no template with two purification steps prior to IVT The entire sample containing IVT-amplified sense RNA molecules from each first-round reaction using a template or no-template control was used for 2nd-round IVT-amplification. The second-round IVT-amplification reaction was performed exactly as described in Example 2. The second-round IVT-amplified sense RNA from each reaction was purified using Illustra™ RNAspin mini RNA isolation columns (GE Healthcare, Baie d'Urfé, QC) and the concentrations determined at A260$_{nm}$. The reactions yielded 72 µg, 38 µg, 94 µg, and 3.6 µg of IVT-amplified sense RNA, respectively. An equal aliquot representing 300 ng of each IVT amplification reaction was analyzed by ethidium bromide stained agarose gel electrophoresis.

FIG. 9, Lane 1 shows the IVT-amplified sense RNA produced using the ribonucleotide rTTO (Seq. ID. No. 4) from 5 ng HeLa RNA template with one purification step prior to IVT in the first-round, Lane 2 shows the IVT-amplified sense RNA from the corresponding no-template reaction, Lane 3 shows the IVT-amplified sense RNA using the ribonucleotide rTTO (Seq. ID. No. 4) from 5 ng HeLa RNA template with two purification steps prior to IVT and Lane 4 shows the IVT-amplified sense RNA from the corresponding no-template reaction.

Although the second-round no-template reaction products (Lane 2 and Lane 4) from the first-round IVT reactions with one and two purification steps, respectively, appeared to be similar in size distribution, the no-template reaction with only one purification step (reaction #2) yielded approximately 10-fold more non-specific products compared to two purification steps (reaction #4). In addition, the specific products formed with two purification steps was lacking the low molecular weight non-specific product (Lane 3) compared to using only one purification step (Lane 1). It was evident that by using the ribonucleotide-containing rTTO oligonucleotide instead of the deoxyribonucleotide-containing dTTO oligonucleotide, there was still a need for a purification step following terminal tagging, most likely to remove deoxyribonucleotide first-strand cDNA synthesis primers that were also terminally tagged. Since the ribonucleotide-containing rTTO oligonucleotides were digested by RNase I following terminal tagging, without being bound by theory, it appears that the non-specific background products result, at least in part, from first-strand cDNA synthesis primers that have the DNA sequence tag joined to their 3'-termini. Consequently, the use of a ribonucleotide first-strand cDNA synthesis primer for first-strand cDNA synthesis instead of a deoxyribonucleotide first-strand cDNA synthesis primer, followed by its removal using RNase I prior to terminal tagging, prevents background due to terminal tagging of the first-strand cDNA synthesis primers.

FIG. 9 contains the following:
Lane 1—300 ng of 2-round IVT-amplified RNA from the 5 ng HeLa RNA template reaction with one purification step prior to IVT in the first-round
Lane 2—300 ng of 2-round IVT-amplified RNA from the no-template reaction with one purification step prior to IVT in the first-round
Lane 3—300 ng of 2-round IVT-amplified RNA from the 5 ng HeLa RNA template reaction with two purification steps prior to IVT in the first-round
Lane 4—300 ng of 2-round IVT-amplified RNA from the no-template reaction with two purification step prior to IVT in the first-round Example 4

Comparing the Use of Different Combinations of Ribo (rU and rTTO) and Deoxy (dT and dTTO) Oligonucleotides in Terminal Tagging to Eliminate or Reduce Non-Specific Background in the Absence of Purification Steps Prior to First-Round IVT Total RNA (100 ng) from HeLa cells (Clontech) was used as template to synthesize first-strand cDNA molecules in a standard cDNA synthesis reaction as described in Example 1 with the exception that either 50 pmoles oligonucleotide rU (Seq. ID. No. 5): $(rU_{20})V$ or dT primer (Seq. ID. No. 1): $(dT_{20})V$. Corresponding no template reactions were also included.

Next, a 2.5 µL terminal tagging mixture comprising either the terminal tagging oligoribonucleotide (rTTO; Seq. ID. No. 4):

GACGAAGACAGUAGACAN$_6$(N(2'-O-methyl))(3'-O-propyl-phosphate)

or the deoxynucleotide terminal tagging oligonucleotide (dTTO; Seq. ID. No. 2):

GACGAAGACAGTAGACAN$_6$(N(2'-O-methyl))(3'-O-propyl-phosphate),

DTT (7.5 mM final concentration) and 25 units MMLV reverse transcriptase to each reaction at 37° C. The reactions were incubated at 37° C. for 30 min followed by 95° C. for 5 min.

The following three combinations of ribo (r) and deoxy (d) oligonucleotides were used in the 1-round amplification reactions:

1) $rU_{20})V$ and rTTO for first-strand cDNA synthesis and terminal tagging, respectively
2) $rU_{20})V$ and dTTO for first-strand cDNA synthesis and terminal tagging, respectively
3) $dT_{20})V$ and dTTO for first-strand cDNA synthesis and terminal tagging, respectively $rU_{20})V$ and $dT_{20})V$ were used at 50 pmoles per reaction whereas, rTTO and dTTO were used at either 250 pmoles or 750 pmoles per reaction.

Following terminal tagging, the reactions were then used directly for second-strand DNA synthesis by adding a 2.5 µL second-strand DNA synthesis mixture comprising 20 pmoles of second-strand cDNA synthesis primer (P3 oligonucleotide; Seq. ID. No. 3):

AATTCTAATACGACTCACTATAGGGAGACGAAGACAGTAGACA,

DTT (5 mM final concentration) and 25 units MMLV RT. Incubation was performed at 37° C. for 30 min followed by 80° C. for 3 min to inactivate the MMLV RT.

Next, the reactions were placed directly at 42° C. and a 40 µL in vitro transcription (IVT) mixture comprising 1× AmpliScribe T7-Flash™ reaction buffer (EPICENTRE Biotechnologies), 9 mM ATP, 9 mM CTP, 9 mM GTP, 9 mM UTP and AmpliScribe T7-Flash™ RNA polymerase (EPICENTRE Biotechnologies) was added to each and incubated for 4 hours. Following IVT, 2 µL pancreatic RNase-free DNase I was added to each reaction and incubated at 37° C. for 15 min. The amplified RNA from each was purified using Illustra™ RNAspin mini RNA isolation columns (GE Healthcare, Baie d'Urfé, QC) and the concentration determined at $A260_{nm}$. The different reactions yielded various amounts of 1-round amplified RNA, which are shown in Table 1. An equal aliquot representing 25% of each IVT reaction, with the exception of reaction #1 and reaction #7 (Table 1) for which only 1% of each reaction products were used due to the higher yields of amplified RNA), were analyzed by ethidium bromide stained agarose gel electrophoresis.

TABLE 1

Shows the 1-round amplified RNA yields and the ratio of non-specific to specific products with the different ribo- and deoxyribo- first-strand cDNA synthesis primers and terminal tagging oligonucleotide combinations.

| | Reaction # | Input total RNA (ng) | $rU_{20})V$ (pmoles) | rTTO (pmoles) | dT (pmoles) | dTTO (pmoles) | 1-round Amplified RNA Yields (µg) | Non-specific:Specific Products Ratio (%) |
|---|---|---|---|---|---|---|---|---|
| A | 1 | 100 | 50 | 250 | — | — | 58.5 | — |
| | 2 | 0 | 50 | 250 | — | — | 0 | 0 |
| | 3 | 100 | — | 250 | 50 | — | 3.2 | — |
| | 4 | 0 | — | 250 | 50 | — | 0.83 | 25.9 |
| | 5 | 100 | — | — | 50 | 250 | 1.1 | — |
| | 6 | 0 | — | — | 50 | 250 | 0.93 | 84.5 |
| B | 7 | 100 | 50 | 750 | — | — | 51.8 | — |
| | 8 | 0 | 50 | 750 | — | — | 0 | 0 |
| | 9 | 100 | — | 750 | 50 | — | 4.4 | — |
| | 10 | 0 | — | 750 | 50 | — | 1.3 | 29.5 |
| | 11 | 100 | — | — | 50 | 750 | 1.3 | — |
| | 12 | 0 | — | — | 50 | 750 | 1.3 | 100 |

FIG. 10, Lane 1 shows the 1-round IVT-amplified sense RNA produced using the $rU_{20}V$ RNA first-strand cDNA synthesis primer (Seq. ID. No. 5) and terminal tagging oligoribonucleotide (rTTO; Seq. ID. No. 4) from 5 ng HeLa RNA template without purification steps prior to first-round IVT, and Lane 2 shows the 1-round IVT-amplified sense RNA from the corresponding no-template reaction; Lane 3 shows the 1-round IVT-amplified sense RNA produced using the $dT_{20}V$ first-strand cDNA synthesis primer (Seq. ID. No. 1) and terminal tagging oligoribonucleotide (rTTO; Seq. ID. No. 4) from 5 ng HeLa RNA template without purification steps prior to first-round IVT, and Lane 4 shows the 1-round IVT-amplified sense RNA from the corresponding no-template reaction; Lane 5 shows the 1-round IVT RNA produced using the $dT_{20}V$ first-strand cDNA synthesis primer (Seq. ID. No. 1) and terminal tagging oligonucleotide (dTTO; Seq. ID. No. 2) from 5 ng HeLa RNA template without purification steps prior to first-round IVT, and Lane 6 shows the IVT-amplified sense RNA from the corresponding no-template reaction. Panels A and B show the results obtained using 250 pmoles and 750 pmoles ribo- or deoxyribo-terminal tagging oligonucleotide per reaction, respectively.

These results show that, when $rU_{20}V$ first-strand cDNA synthesis primer was used for first-strand cDNA synthesis in combination with either 250 pmoles or 750 pmoles of terminal tagging oligoribonucleotide (rTTO) for terminal tagging, there was excellent template-dependent amplification (Table 1) with the appropriate products formed (FIG. 10: Lanes 1A-B). At the same time, there were no measurable ($A260_{nm}$) non-specific amplification products in the corresponding no-template control reactions (Table 1). Also, no products were detectable for the no-template reactions by agarose gel analysis (FIG. 10: Lanes 2A-B). Increasing the amount of terminal tagging oligoribonucleotide (rTTO) for terminal tagging by 3-fold did not lead to an increase in non-specific product formation. No-template 2-round IVT-amplification reactions using the combination of $rU_{20}V$ first-strand cDNA synthesis primer and terminal tagging oligoribonucleotide (rTTO) also did not result in any ($A260_{nm}$) signal due to non-specific IVT-amplification products (data not shown).

However, when $rU_{20}V$ first-strand cDNA synthesis primer was used for first-strand cDNA synthesis in combination with either 250 pmoles or 750 pmoles of dTTO terminal tagging oligonucleotide for terminal tagging, the yield in template-dependent amplification decreased dramatically—by more than 90% compared to reactions that used both the $rU_{20}V$ first-strand cDNA synthesis primer and the terminal tagging oligoribonucleotide (rTTO) (Table 1). In addition, the use of the dTTO terminal tagging oligonucleotide resulted in measurable ($A260_{nm}$) signals in the no-template reactions due to non-specific IVT-amplification (see Table 1). Following electrophoresis, both low- and high-molecular-weight products were evident in the IVT reactions with template (FIG. 10: Lanes 3A-B), as well as in the no-template IVT reactions (FIG. 10: Lanes 4A-B). In fact, the non-specific products seen in the no-template reactions (Lanes 4A-B) were also evident in the IVT reactions with template (Lanes 3A-B). The non-specific products produced represented between 25%-30% of the yields seen for the IVT reactions with template (Table 1).

Furthermore, when $dT_{20}V$ first-strand cDNA synthesis primer was used for first-strand cDNA synthesis in combination with either 250 pmoles or 750 pmoles of dTTO terminal tagging oligonucleotide for terminal tagging, the template-dependent specific product yields decreased even further (>98%) (Table 1) compared to the $rU_{20}V$+rTTO combination. Also, similar low- and high-molecular-weight products were observed in the IVT reactions with template and the no-template reactions (FIG. 10: Lanes 5A-B and 6A-B). In addition, the ratio of non-specific-to-specific products synthesized increased to between 84%-100% (Table 1), indicating that the majority of IVT-amplified products are of the non-specific nature in both the IVT reactions with template and no-template reactions.

Clearly, without the use of any purification steps prior to IVT, the elimination or reduction of background was only observed when the combination of $rU_{20}V$ and rTTO was used for first-strand cDNA synthesis and terminal tagging, respectively.

FIG. 10 contains the following:
Lane 1—Amplified RNA produced using $rU_{20}V$/rTTO with 100 ng total RNA input
Lane 2—Amplified RNA produced using $rU_{20}V$/rTTO with no total RNA input
Lane 3—Amplified RNA produced using $dT_{20}V$/rTTO with 100 ng total RNA input
Lane 4—Amplified RNA produced using $dT_{20}V$/rTTO with no total RNA input
Lane 5—Amplified RNA produced using $dT_{20}V$/dTTO with 100 ng total RNA input
Lane 6—Amplified RNA produced using $dT_{20}V$/dTTO with no total RNA input
A—250 pmoles of the respective terminal tagging oligonucleotide per reaction
B—750 pmoles of the respective terminal tagging oligonucleotide per reaction
M—double-stranded DNA molecular weight marker

Example 5

Exemplary Protocol for a Method for Improved Amplification of Copy DNA and Sense RNA To perform Sense RNA amplification, program a thermocycler as follows (Program A):

| | |
|---|---|
| 65° C. | 5 min |
| 25° C. | 10 min* |
| 45° C. | 60 min* |
| 95° C. | 3 min |
| 30° C. | 15 min |
| 95° C. | 5 min |
| 37° C. | 30 min |
| 95° C. | 3 min |
| 30° C. | 15 min |
| 95° C. | 5 min |
| 37° C. | 30 min |
| 80° C. | 3 min |
| 42° C. | 4 hr |
| 4° C. | Hold |

*Note:
The 25° C. step is only required if random hexamers are used in the first-strand cDNA synthesis reaction. With only the oligo(U)$_n$ first-strand cDNA synthesis primer, skip the 25° C. step and add the 2 μL of the First-strand cDNA Synthesis Premix directly at 45° C.

In a 0.2 mL PCR reaction tube, prepare each reaction mixture comprising 0.5 μL of 10 mM dNTPs, 0.5 μL Oligo (U)$_n$ first-strand cDNA synthesis primer, 0.5 μL ribonucleotide random hexamer first-strand cDNA synthesis primers when the RNA samples is fragmented (otherwise, replace it with RNase-free water), and 1.5 μL sample containing the RNA of interest in RNase-free H$_2$O. Gently mix the reaction components by flicking the tube, spin briefly and place the reaction tube in the thermocycler. Start Program A.

During the 65° C./5 min incubation step, prepare a First-strand cDNA Synthesis Premix for all reactions on ice comprising 1.0 μL of 5×AMV buffer (250 mM Tris-HCl, pH 8.3, 500 mM KCl, 20 mM DTT and 50 mM MgCl$_2$) (Life Sciences, St. Petersburg, Fla.), 0.1 μL ScriptGuard™ RNase Inhibitor (40 U/μL) (EPICENTRE Biotechnologies, Madison, Wis.), 0.75 μL RNase-free H$_2$O and 0.15 μL AMV reverse transcriptase (35 U/μL) (Life Sciences, St. Petersburg, Fla.) for each reaction. It is important to prepare sufficient First-strand cDNA Synthesis Premix for at least 1 extra reaction. If random hexamer first-strand cDNA synthesis primers are used, pause Program A at the start of the 25° C. step and add 2 μL of the First-strand cDNA Synthesis Premix to each reaction on the thermocycler. Continue incubation followed by the 45° C. for 60 min and 95° C. for 3 min. Alternatively, if only oligo(U), first-strand cDNA synthesis primer is used, pause Program A at the start of the 45° C. step and add 2 μL of the First-strand cDNA Synthesis Premix to each reaction on the thermocycler. Incubate at 45° C. for 60 min and 95° C. for 3 min. Then, pause Program A at the start of the 30° C. step and add 0.5 μL RNase Mix (1:1 vol RNase H and RNase I) (EPICENTRE Biotechnologies, Madison, Wis.) to each reaction on the thermocycler. Continue Program A at 30° C. for 15 min and 95° C. for 5 min.

During the 95° C./5 min incubation step, prepare a Tagging Premix for all reactions on ice comprising 1.0 μL rTTO (Seq. ID No. 4), 0.5 μL 100 mM DTT and 0.5 μL MMLV (50 U/μL) for each reaction. It is important to prepare sufficient Tagging Premix for at least 1 extra reaction. Pause Program A at the start of the 37° C. step and add 2 μL of the Tagging Premix to each reaction on the thermocycler. Continue Program A at 37° C. for 30 min and 95° C. for 3 min. Then, pause Program A at the start of 30° C. and add 0.5 μL RNase Mix to each reaction on the thermocycler. Continue Program A at 30° C. for 15 min and 95° C. for 5 min.

During the 95° C./5 min incubation step, prepare a Second-strand cDNA Synthesis Premix for all reactions on ice comprising 1.0 μL Primer 3, 0.5 μL 100 mM DTT and 0.5 μL MMLV (50 U/μL) for each reaction. It is important to prepare sufficient Second-strand Premix for at least 1 extra reaction. Pause Program A at the start of 37° C. and add a 2 μL of the Second-strand cDNA Synthesis Premix to each reaction on the thermocycler. Continue Program A at 37° C. for 30 min and 80° C. for 3 min.

During the 80° C./3 min incubation step, prepare an IVT Premix for all reactions comprising 13.6 μL RNase-free H$_2$O, 4.0 μL AmpliScribe™ T7-Flash™ 10× reaction buffer (EPICENTRE Biotechnologies, Madison, Wis.), 3.6 μL 100 mM ATP, 3.6 μL 100 mM CTP, 3.6 μL 100 mM GTP, 3.6 μL 100 mM UTP, 4.0 μL 100 mM DTT and 4.0 μL AmpliScribe™ T7-Flash™ RNA polymerase enzyme (EPICENTRE Biotechnologies, Madison, Wis.) for each reaction. It is important to prepare sufficient IVT Premix for at least 0.5 extra reaction. Pause Program A at the start of the 42° C. step and add 40 μL of the IVT Premix to each reaction on the thermocycler. Continue Program A for 4 hours at 42° C. and then at 4° C. (HOLD) if necessary.

For one-round RNA amplification, proceed to treat the samples with RNase-free DNase I as follows: Program Thermocycler for 15 min at 37° C. and place completed IVT reaction tubes on thermocycler. Add 2 μL RNase-free DNase I (EPICENTRE Biotechnologies, Madison, Wis.) to each reaction and incubate for 15 min at 37° C. Purify amplified RNA using RNA spin columns.

Example 6

3'/5' Sequence Ratios of Amplified Sense RNA Produced Using the Exemplary Protocol Described in Example 5 Compared to Eberwine's cRNA The exemplary 1-round protocol described in Example 5 but with MMLV RT instead of AMV RT was used to synthesize amplified sense RNA from 100 ng input of universal human reference total RNA (Stratagene). A similar quantity of the total RNA was used in a 1-round TargetAmp™ Eberwine procedure (EPICENTRE Biotechnologies) to generate amplified cRNA. Random primed cDNA was then synthesized from one microgram each of the sense RNA and cRNA, and the samples were diluted 100-fold with distilled water and 1-μl aliquots were used in 25-μl qPCR reactions with TAQurate™ Green PCR MasterMix (EPICENTRE Biotechnologies) and primer pairs specific to several genes (see Table 2). The cycle threshold (CT) values obtained with each primer pair were used to calculate the 3'/5' ratio for each cDNA produced using the equation 3'/5' ratio=2(CT5'-CT3'). The 3'/5' sequence ratios for the different reactions using either cDNA from sense RNA or cRNA are shown in Table 2.

TABLE 2

Shows the 3'/5' sequence ratios obtained by QPCR analysis of cDNA synthesized from either 1-round sense RNA or 1-round cRNA.

| Gene Symbol | Transcript Length (nt) | 3'/5' ratio (1-round) | |
|---|---|---|---|
| | | Sense RNA | cRNA |
| GUSB | 2245 | 0.8 | 36.8 |
| TUBA | 1706 | 0.9 | 223 |
| ENSA | 2512 | 0.9 | 24.3 |
| ACTB | 1792 | 0.3 | 73.5 |
| TFRC | 5010 | 0.3 | 256 |
| GAPDH | 1310 | 1.2 | 181 |
| PKG1 | 2338 | 0.4 | 24.3 |

TABLE 2-continued

Shows the 3'/5' sequence ratios obtained by QPCR analysis of cDNA synthesized from either 1-round sense RNA or 1-round cRNA.

| Gene Symbol | Transcript Length (nt) | 3'/5' ratio (1-round) Sense RNA | cRNA |
|---|---|---|---|
| H3F3A | 1117 | 1.6 | 12.1 |
| ALB | 2215 | 1.5 | 9.8 |
| HPRT | 1331 | 0.3 | 6.1 |

In general, 3'/5' ratio values around 1.0 were seen for the sense RNA sample, which was significantly better than the corresponding cRNA sample, demonstrating that both 5' and 3' transcript information are preserved using the sense RNA amplification process. The cRNA sample exhibited very high 3' sequence bias for all genes studied with 3'/5' ratio values much greater than one.

Example 7

Performance of cDNA Targets Prepared from 1-Round Amplified Sense RNA and Unamplified Total RNA on NimbleGen Gene Expression Microarrays The performance of the 1-round sense RNA compared to unamplified total RNA was assessed on NimbleGen Systems gene expression microarrays. Replicate 100 nanograms total RNA samples of Human Brain RNA (Ambion) and Human Universal Reference RNA (Stratagene) were independently amplified using the sense RNA amplification procedure as described in Example 5. A 10-µg aliquot of each sense RNA sample was then converted to dsDNA by performing first- and then second-strand primer-directed cDNA synthesis. Unamplified RNA was used as a control in the experiment, and a 10 µg aliquot of each of unamplified Human Brain RNA and unamplified Human Universal Reference RNA were converted to dsDNA using NimbleGen's protocol for gene expression analysis. Cy3™-labeled DNA targets were produced from each amplified and unamplified dsDNA preparation by the standard labeling procedure as recommended by NimbleGen Systems. The labeled targets were hybridized to a NimbleGen Systems HG18 4-Plex Array and data analysis was performed by NimbleGen Systems, using the Bioconductor package.

In order to assess reproducibility of the sense RNA, $\log_2$ signal values obtained with microarray targets generated from independently amplified sense-RNA batches were plotted (FIG. 12A). For comparison, we also showed reproducibility of technical replicates obtained with unamplified total RNA targets. The high $r^2$ values of 0.985 for sense RNA amplified targets and 0.993 for unamplified targets demonstrated excellent reproducibility of the sense RNA amplification process essentially similar to unamplified total RNA targets.

Figure 12B:
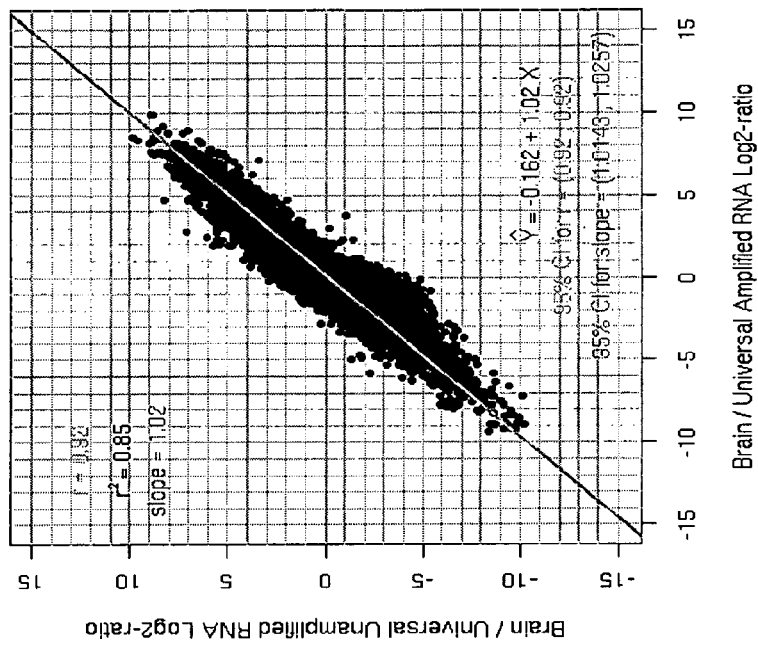
FIG. 12B—Shows the correlation between expression ratios obtained using labeled cDNA targets prepared from amplified 5'-tagged sense RNA prepared using the method and from unamplified brain RNA from reference RNA and universal human reference RNA. The signal ratios obtained using the labeled cDNA targets were analyzed following hybridization to microarrays by NimbleGen Systems. A correlation value of $r=0.92$ between the expression ratios obtained with labeled cDNA targets prepared using amplified 5'-tagged sense RNA and unamplified total RNA targets indicated that the linearity of differential gene expression is very well preserved in the amplified 5'-tagged sense RNAs compared to unamplified total RNAs. Thus, the expression profiles of the original samples are faithfully preserved during the sense RNA amplification process.

Next, the $\log_2$ signal ratios of brain RNA versus universal human reference RNA were compared for each transcript for the amplified sense RNA and unamplified total RNA labeled DNA targets hybridized to the microarrays from NimbleGen Systems. FIG. 12B shows the correlation between gene expression ratios obtained with amplified and unamplified targets. A correlation value of r=0.92 between the expression ratios obtained with amplified sense RNA and unamplified total RNA targets indicated that the linearity of differential gene expression is very well preserved in the amplified sense RNA compared to unamplified total RNA. Thus, the differential expression profiles of the original samples are being faithfully preserved during the sense RNA amplification process.

Figure 12C:
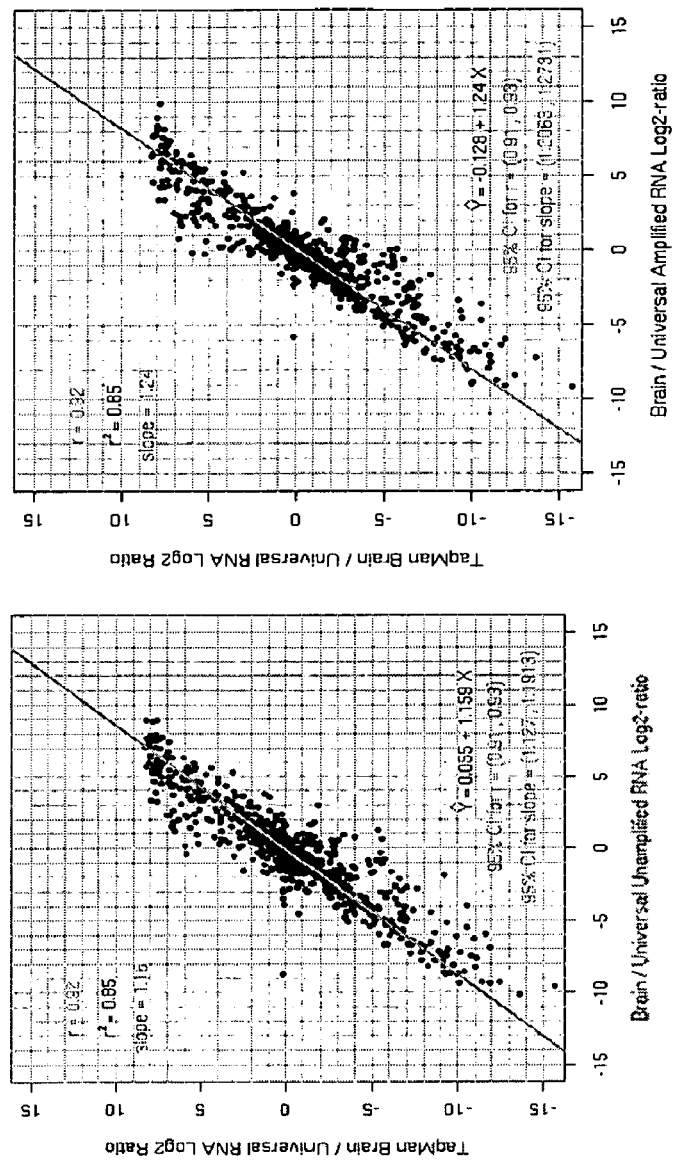
FIG. 12C—Shows the correlation between $\log_2$ expression ratios correlation between the microarray data from Nimble-Gen gene expression arrays of labeled double-stranded cDNA targets prepared from the amplified sense RNA and unamplified total RNA from Human Brain Reference RNA and Universal Human Reference RNA and TaqMan® Data from The Microarray Quality Control Consortium (MAQC) for a panel of approximately 1,000 transcripts. The correlation coefficient that was obtained ($r=0.92$) for both sense RNA and unamplified total RNA cDNA targets is equal to the highest values published by the MAQC Consortium, indicating that both sense RNA-derived and unamplified RNA derived targets produced microarray results that correlate very well with the TaqMan results. Thus, there was a high "true positive rate" of differential expression for sense RNA, similar to unamplified RNA, when compared to the MAQC TaqMan assay results.

Next, the differential gene expression ratios obtained for the amplified sense RNA and unamplified total RNA were compared with TaqMan® Data from The Microarray Quality Control Consortium (MAQC) for a panel of ~1,000 transcripts, for human brain RNA and universal human reference RNA. These MAQC data is publicly available from the MAQC website (http://edkb.fda.gov/MAQC/MainStudy/upload/). FIG. 12C shows the correlation between $\log_2$ gene expression ratios from the MAQC TaqMan assays and the microarray differential expression data for the amplified sense RNA and unamplified total RNA obtained using NimbleGen gene expression arrays. The correlation coefficient obtained (r=0.92) is equal to the highest values published by the MAQC Consortium, indicating that both sense RNA-derived and unamplified RNA-derived DNA targets produced microarray results that correlate very well with the published TaqMan results. Thus, there was a high "true positive rate" of differential expression for sense RNA, similar to unamplified RNA, when compared to the known MAQC TaqMan assay results for similar RNA samples.

Example 8

First-Round Sense RNA is Efficiently Amplified in a 2-Round Sense RNA Amplification Procedure First-round sense RNA from 100 ng input human reference total RNA was produced using the exemplary procedure described in Example 5. Aliquots comprising 1000 ng, 100 ng and 10 ng of the first-round sense RNA were amplified in a second-round sense RNA amplification procedure. An equivalent volume of a first-round no template reaction corresponding to the volume used for the 1000 ng template amount in second-round was also included in order to evaluate any non-specific background amplification after 2-rounds.

In a 0.2 mL PCR reaction tube, prepare each reaction mixture comprising 0.4 µL of 25 mM dNTPs, 0.5 µL (50 pmoles) Oligo(U)$_n$ first-strand cDNA synthesis primer and the first-round sense RNA sample in a final volume of 8.9 µL. Gently mix the reaction components by flicking the tube, spin briefly and place the reaction tube in the thermocycler. Start Program B outlined below.

To perform second-round sense RNA amplification, program a thermocycler as follows (Program B):

| | |
|---|---|
| 65° C. | 5 min |
| 45° C. | 60 min |
| 95° C. | 3 min |
| 30° C. | 15 min |
| 95° C. | 5 min |
| 37° C. | 30 min |
| 80° C. | 3 min |
| 42° C. | 4 hr |
| 4° C. | Hold |

During the 65° C./5 min incubation step, prepare a First-strand cDNA Synthesis Premix for all reactions on ice comprising 2.0 µL of 5×AMV buffer (250 mM Tris-HCl, pH 8.3, 500 mM KCl, 25 mM DTT and 50 mM MgCl$_2$) (Life Sciences, St. Petersburg, Fla.), 0.1 µL ScriptGuard™ RNase Inhibitor (40 U/μL) (EPICENTRE Biotechnologies, Madison, Wis.), 0.55 μL RNase-free H$_2$O and 5 U AMV reverse transcriptase (Life Sciences, St. Petersburg, Fla.) in a final volume of 2.8 μL for each reaction. It is important to prepare sufficient First-strand cDNA Synthesis Premix for at least 1 extra reaction. Pause Program B at the start of the 45° C. step and add 2.8 μL of the First-strand cDNA Synthesis Premix to each reaction on the thermocycler. Incubate at 45° C. for 60 min and 95° C. for 3 min. Then, pause Program B at the start of the 30° C. step and add 0.5 μL RNase Mix (RNase H and RNase I) (EPICENTRE Biotechnologies, Madison, Wis.) to each reaction on the thermocycler. Continue Program B at 30° C. for 15 min and 95° C. for 5 min.

During the 95° C./5 min incubation step, prepare a Second-strand cDNA Synthesis Premix for all reactions on ice comprising 1.0 μL Primer 3 (20 μM), 0.5 μL 100 mM DTT, 0.8 μL water and 0.5 μL MMLV (50 U/μL) for each reaction. It is important to prepare sufficient Second-strand Premix for at least 1 extra reaction. Pause Program B at the start of 37° C. and add a 2.8 μL of the Second-strand cDNA Synthesis Premix to each reaction on the thermocycler. Continue Program B at 37° C. for 30 min and 80° C. for 3 min.

During the 80° C./3 min incubation step, prepare an IVT Premix for all reactions comprising 8.6 μL RNase-free H$_2$O, 4.0 μL AmpliScribe T7-Flash™ 10× reaction buffer (EPICENTRE Biotechnologies, Madison, Wis.), 3.6 μL 100 mM ATP, 3.6 μL 100 mM CTP, 3.6 μL 100 mM GTP, 3.6 μL 100 mM UTP, 4.0 μL 100 mM DTT and 4.0 μL AmpliScribe™ T7-Flash™ RNA polymerase enzyme (EPICENTRE Biotechnologies, Madison, Wis.) for each reaction. It is important to prepare sufficient IVT Premix for at least 0.5 extra reaction. Pause Program B at the start of the 42° C. step and add 35 μL of the IVT Premix to each reaction on the thermocycler. Continue Program B for 4 hours at 42° C. and then at 4° C. (HOLD) if necessary.

Following the second-round RNA amplification, proceed to treat the each reaction with RNase-free DNase I as follows: Program Thermocycler for 15 min at 37° C. and place completed IVT reaction tubes on thermocycler. Add 2 μL RNase-free DNase I (EPICENTRE Biotechnologies, Madison, Wis.) to each reaction and incubate for 15 min at 37° C. Purify amplified RNA using RNA spin columns and quantify using a spectrophotometer at A260 μm. The 2-round amplified sense RNA yields are shown in Table 3.

TABLE 3

Two-round sense RNA yields.

| 1-round sRNA Inputs (ng) | 2-round sense RNA Yields (μg) |
|---|---|
| 1000 | 272 |
| 100 | 53 |
| 10 | 4 |
| 0 | 0 |

The 2-round sense RNA yields from 10 ng and 100 ng 1-round sense RNA inputs appear to be in the linear range compared to the 1000 ng input, which may be the result of limits of the purification column used. Nevertheless, it is clear that the 1-round sense RNA can be further amplified in a second-round sense RNA amplification procedure using oligo(U)$_n$ for first-strand cDNA synthesis. In addition, the 1-round no template sample gave no measureable non-specific background RNA even after 2-round of amplification.

Example 9

Preservation of Full-Length Sequences Between First- and Second-Round Sense RNA Amplification First-round sense RNA from 25 ng input universal human reference total RNA was synthesized using the exemplary procedure described in Example 5. The 1-round sense RNA yield was 25 μg and from this, an aliquot comprising 500 ng was amplified in a modified second-round sense RNA amplification procedure from that described in Example 8 as follows:

In a 0.2 mL PCR reaction tube, prepare each reaction mixture comprising, 0.5 μL (50 pmoles) oligo(U)$_n$ first-strand cDNA synthesis primer and the first-round RNA sample in a final volume of 12.5 μL. Gently mix the reaction components by flicking the tube, spin briefly and place the reaction tube in the thermocycler. Start Program B of Example 8.

During the 65° C./5 min incubation step, prepare a First-strand cDNA Synthesis Premix for all reactions on ice comprising 2.5 μL of 5×AMV buffer (250 mM Tris-HCl, pH 8.3, 500 mM KCl, 20 mM DTT and 50 mM MgCl$_2$) (Life Sciences, St. Petersburg, Fla.), 1.0 μL of 25 mM dNTPs, 0.25 μL ScriptGuard™ RNase Inhibitor (40 U/μL) (EPICENTRE Biotechnologies, Madison, Wis.), and 5 U AMV reverse transcriptase (Life Sciences, St. Petersburg, Fla.) in a final volume of 4.0 μL for each reaction. It is important to prepare sufficient First-strand cDNA Synthesis Premix for at least 1 extra reaction. Pause Program B at the start of the 45° C. step and add 4.0 μL of the First-strand cDNA Synthesis Premix to each reaction on the thermocycler. Incubate at 45° C. for 60 min and 95° C. for 3 min. Then, pause Program B at the start of the 30° C. step and add 0.5 μL RNase Mix (RNase H and RNase I) (EPICENTRE Biotechnologies, Madison, Wis.) to each reaction on the thermocycler. Continue Program B at 30° C. for 15 min and 95° C. for 5 min.

During the 95° C./5 min incubation step, prepare a Second-strand cDNA Synthesis Premix for all reactions on ice comprising 0.5 μL Primer 3 (40 μM), 1.0 μL 100 mM DTT, 1.0 μL water and 0.5 μL MMLV (50 U/μL) for each reaction. It is important to prepare sufficient Second-strand Premix for at least 1 extra reaction. Pause Program B at the start of 37° C. and add a 3.0 μL of the Second-strand cDNA Synthesis Premix to each reaction on the thermocycler. Continue Program B at 37° C. for 30 min and 80° C. for 3 min.

During the 80° C./3 min incubation step, prepare an IVT Premix for all reactions comprising 13.6 μL RNase-free H$_2$O, 4.0 μL AmpliScribe T7-Flash™ 10× reaction buffer (EPICENTRE Biotechnologies, Madison, Wis.), 3.6 μL 100 mM ATP, 3.6 μL 100 mM CTP, 3.6 μL 100 mM GTP, 3.6 μL 100 mM UTP, 4.0 μL 100 mM DTT and 4.0 μL AmpliScribe™ T7-Flash™ RNA polymerase enzyme (EPICENTRE Biotechnologies, Madison, Wis.) for each reaction. It is important to prepare sufficient IVT Premix for at least 0.5 extra reaction. Pause Program B at the start of the 42° C. step and add 40 μL of the IVT Premix to each reaction on the thermocycler. Continue Program B for 4 hours at 42° C. and then at 4° C. (HOLD) if necessary.

Following the two-round sense RNA amplification procedure, proceed to treat each reaction with RNase-free DNase I as follows: Program Thermocycler for 15 min at 37° C. and place completed IVT reaction tubes on thermocycler. Add 2 μL RNase-free DNase I (EPICENTRE Biotechnologies, Madison, Wis.) to each reaction and incubate for 15 min at 37° C. Purify amplified RNA using RNA spin columns and quantify using a spectrophotometer at A260$_{nm}$. The 2-round sense RNA amplification yield from 500 ng input of 1-round sense RNA was approximately 174 µg.

Figure 13:
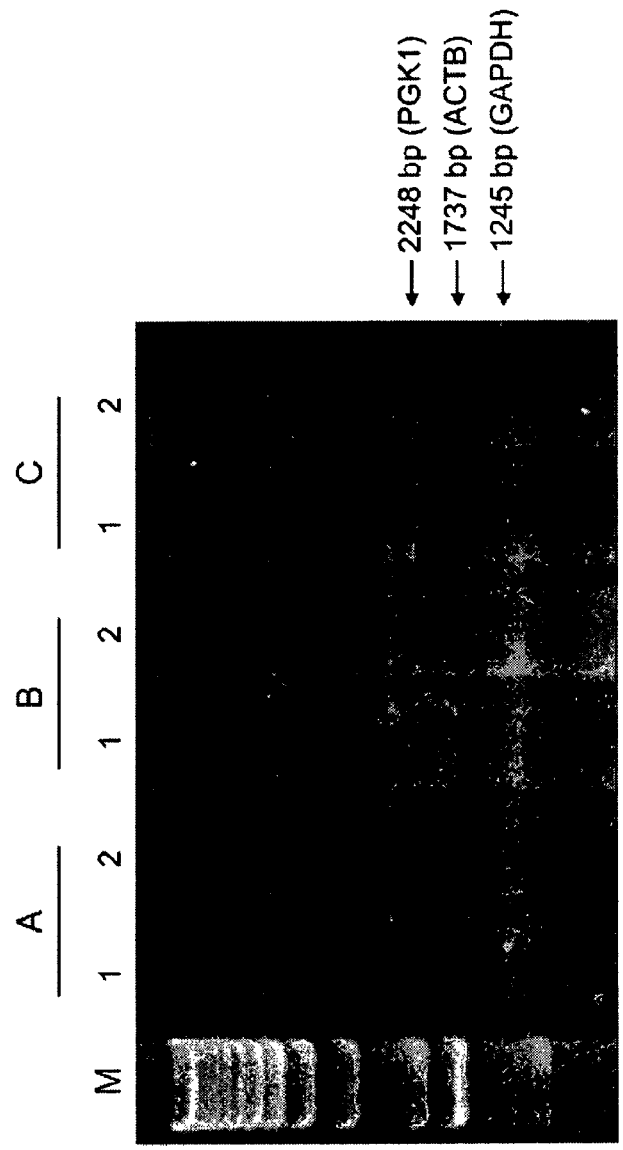
FIG. 13—Shows the results of RT-PCR amplification of specific genes present in the amplified sense RNA obtained after one round and two rounds of sense RNA amplification using the methods of the present invention. The gel photo shows very similar representation of full-length transcripts for GAPDH, ACTB and PGK1 in the sense RNA samples obtained after either one round (Lanes A1, B1 and C1) or two rounds (Lanes A2, B2 and C2) of sense RNA amplification using the methods of the present invention, indicating that the quality of the amplified sense RNA is conserved between rounds of amplification.

First-strand cDNA was then synthesized from 1000 ng of either of the first- or second-round sense RNA and 10% used as template in each PCR reaction (30 cycles) with primers specific for full-length GAPDH, ACTB and PGK1 as shown below. FIG. 13 shows the RT-PCR amplification results obtained.

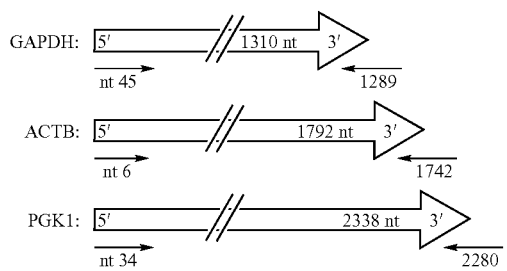

Clearly, primers specific for full-length GAPDH, ACTB and PGK1 showed very similar representation of each full-length gene in both the first- (Lanes A1, B1 and C1) and second-round (Lanes A2, B2 and C2) sense RNA samples indicating that the quality of the amplified sense RNA is conserved between the rounds of amplification.

FIG. 13 contains the following:
Lane M—1 Kb ladder
Lane 1—RT-PCR amplicons using cDNA from first-round sense RNA as template
Lane 2—RT-PCR amplicons using cDNA from second-round sense RNA as template
Panel A—GAPDH
Panel B—ACTB
Panel C—PGK1

Example 10

Optimized Two-Round Sense RNA Amplification Procedure for Low Inputs of Total RNA (≦500 Cells)

In order to obtain increased sensitivity for the two-round amplification from low inputs of total RNA (≦500 cells), a modified one- and two-round procedure was as follows was developed.

The first-round sense RNA procedure described in Example 5 is performed but with the following modifications:
1) 2.5 pmoles of the oligo(U)$_n$ is used instead of 50 pmoles
2) 125 pmoles of rTTO is used instead 250 pmoles
3) 4 pmoles of Primer 3 is used instead of 20 pmoles
4) 1 U AMV RT is used instead of 5 U and,
5) 20 µL of IVT mixture is used instead of 40 µL Following the first-round sense RNA amplification reaction, the synthesized RNA is purified using for example, RNA Clean Up Columns-5 (ZYMO Research) and eluted in a total of 14-µL water. Typically, the recovery following purification is approximately 11.5 µL and this entire volume is then used in the second-round sense RNA amplification procedure as follows:

In a 0.2 mL PCR reaction tube, prepare each reaction mixture comprising 0.5 µL (50 moles) oligo(U)$_n$ first-strand cDNA synthesis primer, 0.5 µL (25 pmoles) ribonucleotide random hexamer first-strand cDNA synthesis primers and the first-round sense RNA sample in a final volume of 12.5 µL.

Gently mix the reaction components by flicking the tube, spin briefly and place the reaction tube in the thermocycler. Start Program C as outlined below:

To perform the two-round sense RNA amplification procedure, program a thermocycler as follows (Program C):

| | |
|---|---|
| 65° C. | 5 min |
| 4° C. | Pause |
| 25° C. | 10 min |
| 45° C. | 50 min |
| 95° C. | 3 min |
| 30° C. | 15 min |
| 95° C. | 5 min |
| 37° C. | 30 min |
| 80° C. | 3 min |
| 42° C. | 4 hr |
| 4° C. | Hold |

During the 65° C./5 min incubation step, prepare a First-strand cDNA Synthesis Premix for all reactions on ice comprising 2.5 µL of 5×AMV buffer (250 mM Tris-HCl, pH 8.3, 500 mM KCl, 25 mM DTT and 50 mM MgCl$_2$) (Life Sciences, St. Petersburg, Fla.), 1.0 µL 25 mM dNTPs, 0.25 µL ScriptGuard™ RNase Inhibitor (40 U/µL) (EPICENTRE Biotechnologies, Madison, Wis.), 2.5 U AMV reverse transcriptase (Life Sciences, St. Petersburg, Fla.) in a final volume of 4.0 µL for each reaction. It is important to prepare sufficient First-strand cDNA Synthesis Premix for at least 1 extra reaction. Pause Program C at the start of the 4° C. step and add 4.0 µL of the First-strand cDNA Synthesis Premix to each reaction on the thermocycler. Incubate at 25° C. for 10 min followed by 45° C. for 50 min and 95° C. for 3 min. Then, pause Program C at the start of the 30° C. step and add 0.5 µL RNase Mix (RNase H and RNase J) (EPICENTRE Biotechnologies, Madison, Wis.) to each reaction on the thermocycler. Continue Program C at 30° C. for 15 min and 95° C. for 5 min.

During the 95° C./5 min incubation step, prepare a Second-strand cDNA Synthesis Premix for all reactions on ice comprising 0.5 µL Primer 3 (40 µM), 1.0 µL 100 mM DTT, 1.0 µL water and 0.5 µL MMLV (50 U/µL) for each reaction. It is important to prepare sufficient Second-strand Premix for at least 1 extra reaction. Pause Program C at the start of 37° C. and add a 3.0 µL of the Second-strand cDNA Synthesis Premix to each reaction on the thermocycler. Continue Program C at 37° C. for 30 min and 80° C. for 3 min.

During the 80° C./3 min incubation step, prepare an IVT Premix for all reactions comprising 13.6 µL RNase-free H$_2$O, 4.0 µL AmpliScribe T7-Flash™ 10× reaction buffer (EPICENTRE Biotechnologies, Madison, Wis.), 3.6 µL 100 mM ATP, 3.6 µL 100 mM CTP, 3.6 µL 100 mM GTP, 3.6 µL 100 mM UTP, 4.0 µL 100 mM DTT and 4.0 µL AmpliScribe™ T7-Flash™ RNA polymerase enzyme (EPICENTRE Biotechnologies, Madison, Wis.) for each reaction. It is important to prepare sufficient IVT Premix for at least 0.5 extra reaction. Pause Program C at the start of the 42° C. step and add 40 µL of the IVT Premix to each reaction on the thermocycler. Continue Program C for 4 hours at 42° C. and then at 4° C. (HOLD) if necessary.

Following the two-round sense RNA amplification procedure, proceed to treat the each reaction with RNase-free DNase I as follows: Program Thermocycler for 15 min at 37° C. and place completed IVT reaction tubes on thermocycler. Add 2 µL RNase-free DNase I (EPICENTRE Biotechnologies, Madison, Wis.) to each reaction and incubate for 15 min at 37° C. Purify amplified RNA using RNA spin columns and quantify using a spectrophotometer at A260$_{nm}$. The two-round sense RNA amplification yields obtained from the low inputs of total RNA are shown in Table 4.

| Human Reference Total RNA Inputs (pg) | Approximate # of cells | Average 2-round sense RNA Yeilds (µg) |
|---|---|---|
| 500 | 50 | 49.3 |
| 100 | 10 | 5.9 |
| 50 | 5 | 2.5 |
| 10 | 1 | 0.4 |
| 0 | 0 | 0.09 |

Using the optimized two-round sense RNA procedure described herein, the amplified sense RNA produced from low inputs of total RNA were further tested in RT-PCR reactions for a number of genes (GAPDH, ACTB, TFRC and PGK1) and the 3' and 5' regions of the transcripts from as little as 10 pg input total RNA were detected (data not shown). Clearly, the two-round sense RNA amplification procedure described herein is capable of sensitive amplification of input total RNA from only a small number of cells.

Example 11

Exemplary Protocol for Producing Amplified Anti-Sense RNA Containing a 3'Terminal Tag Sequence In order to synthesize amplified anti-sense RNA, which contains a fixed sequence tag on its 3'-end, perform the following procedure:
Program a thermocycler as follows (Program D):

| | |
|---|---|
| 65° C. | 5 min |
| 45° C. | 60 min |
| 95° C. | 3 min |
| 30° C. | 15 min |
| 95° C. | 5 min |
| 37° C. | 30 min |
| 95° C. | 3 min |
| 30° C. | 15 min |
| 95° C. | 5 min |
| 37° C. | 30 min |
| 80° C. | 3 min |
| 42° C. | 4 hr |
| 4° C. | Hold |

In a 0.2 mL PCR reaction tube, prepare each reaction mixture comprising 0.5 µL (either 2.5 pmoles or 50 pmoles) T7-Oligo(dT) first-strand cDNA synthesis primer and the total RNA of interest in RNase-free H$_2$O to a final volume of 3 µL. In this example, 100 ng Universal Human Reference RNA was used. For no template control reactions, replace the total RNA sample with RNase-free water. Gently mix the reaction components by flicking the tube, spin briefly and place the reaction tube in the thermocycler. Start Program D. The following reactions were performed:

1, 2—100 ng total RNA sample with 2.5 pmoles T7-oligo (dT)

3, 4—no template with 2.5 pmoles T7-oligo(dT)

5, 6—100 ng total RNA sample with 50 pmoles T7-oligo (dT)

7, 8—no template with 50 pmoles T7-oligo(dT)

During the 65° C./5 min incubation step, prepare a First-strand cDNA Synthesis Premix for all reactions on ice comprising 1.0 µL of 5×AMV buffer (250 mM Tris-HCl, pH 8.3, 500 mM KCl, 20 mM DTT and 50 mM MgCl$_2$) (Life Sciences, St. Petersburg, Fla.), 0.5 µL of 10 mM dNTPs, 0.25 µL ScriptGuard™ RNase Inhibitor (40 U/µL) (EPICENTRE Biotechnologies, Madison, Wis.) and 5 U AMV reverse transcriptase (Life Sciences, St. Petersburg, Fla.) in a final volume of 2 µL for each reaction. It is important to prepare sufficient First-strand cDNA Synthesis Premix for at least 1 extra reaction. Pause Program D at the start of the 45° C. step and add 2 µL of the First-strand cDNA Synthesis Premix to each reaction on the thermocycler. Incubate at 45° C. for 60 min and 95° C. for 3 min. Then, pause Program D at the start of the 30° C. step and add 0.5 µL RNase Mix (RNase H and RNase I) (EPICENTRE Biotechnologies, Madison, Wis.) to each reaction on the thermocycler. Continue Program D at 30° C. for 15 min and 95° C. for 5 min.

During the 95° C./5 min incubation step, prepare a Tagging Premix for all reactions on ice comprising 1.0 µL (250 pmoles) rTTO (Seq. ID No. 4), 0.5 µL 100 mM DTT and 0.5 µL MMLV (50 U/µL) for each reaction. It is important to prepare sufficient Tagging Premix for at least 1 extra reaction. Pause Program D at the start of the 37° C. step and add 2 µL of the Tagging Premix to each reaction on the thermocycler. Continue Program D at 37° C. for 30 min and 95° C. for 3 min. Then, pause Program D at the start of 30° C. and add 0.5 µL RNase Mix to each reaction on the thermocycler. Continue Program D at 30° C. for 15 min and 95° C. for 5 min.

During the 95° C./5 min incubation step, prepare a Second-strand cDNA Synthesis Premix for all reactions on ice comprising 1.0 µL (20 pmoles) Primer 4, 0.5 µL 100 mM DTT and 0.5 µL MMLV (50 U/µL) for each reaction. It is important to prepare sufficient Second-strand Premix for at least 1 extra reaction. Pause Program D at the start of 37° C. and add a 2 µL of the Second-strand cDNA Synthesis Premix to each reaction on the thermocycler. Continue Program D at 37° C. for 30 min and 80° C. for 3 min.

During the 80° C./3 min incubation step, prepare an IVT Premix for all reactions comprising 13.6 µL RNase-free H$_2$O, 4.0 µL AmpliScribe™ T7-Flash™ 10× reaction buffer (EPICENTRE Biotechnologies, Madison, Wis.), 3.6 µL 100 mM ATP, 3.6 µL 100 mM CTP, 3.6 µL 100 mM GTP, 3.6 µL 100 mM UTP, 4.0 µL 100 mM DTT and 4.0 µL AmpliScribe™ T7-Flash™ RNA polymerase enzyme (EPICENTRE Biotechnologies, Madison, Wis.) for each reaction. It is important to prepare sufficient IVT Premix for at least 0.5 extra reaction. Pause Program D at the start of the 42° C. step and add 40 µL of the IVT Premix to each reaction on the thermocycler. Continue Program D for 4 hours at 42° C. and then at 4° C. (HOLD) if necessary.

Following the one-round RNA amplification procedure, proceed to treat each reaction with RNase-free DNase I as follows: Program Thermocycler for 15 min at 37° C. and place completed IVT reaction tubes on thermocycler. Add 2 µL RNase-free DNase I (EPICENTRE Biotechnologies, Madison, Wis.) to each reaction and incubate for 15 min at 37° C. Purify amplified RNA using RNA spin columns. The one-round amplification yields for the 100 ng of total RNA inputs and no template reactions with either 2.5 pmoles or 50 pmoles of T7-oligo(dT) are shown in Table 5.

| Total RNA Input (ng) | T7-oligo(dT) (pmoles) | Average anti-sense RNA Yeilds (µg) |
|---|---|---|
| 100 | 2.5 | 7.6 |
| 0 | 2.5 | 0 |

-continued

| Total RNA Input (ng) | T7-oligo(dT) (pmoles) | Average anti-sense RNA Yeilds (µg) |
|---|---|---|
| 100 | 50 | 6 |
| 0 | 50 | 0.9 |

Using the one-round anti-sense RNA amplification procedure described herein, it is possible synthesize amplified anti-sense RNA from total RNA, which contains a 3' terminal tag sequence. The specific anti-sense one-round RNA yield using 2.5 pmoles of the T7-oligo(dT) primer for first-strand cDNA synthesis was slightly higher than when 50 pmoles of the T7-oligo(dT) primer was used. But more importantly, the non-specific background yield was essentially zero with 2.5 pmoles of the T7-oligo(dT) compared to around one microgram with 50 pmoles of the T7-oligo(dT) primer, which is important for subsequent rounds of amplification to minimize RNA background.

All publications, patents and patent applications mentioned in the above specification are herein incorporated by reference. Various modifications and variations of the described methods, compositions, and kits of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method comprising:

(A) providing:

a sample containing one or more RNA molecules of interest;

at least one RNA-dependent DNA polymerase;

a terminal tagging oligoribonucleotide comprising ribonucleotides (rTTO), which terminal tagging oligoribonucleotide comprises a 5'-portion and 3'-portion, wherein the 5'-portion exhibits a sequence that is complementary to the sequence of a DNA sequence tag that it is desired to join to the 3'-termini of first-strand cDNA molecules, and wherein the 3'-portion comprises at least three random nucleotides, of which the 3'-terminal nucleotide is blocked so that it is not capable of being extended by a DNA polymerase;

a second-strand cDNA synthesis primer, comprising an oligodeoxyribonucleotide that comprises a 5'-portion and a 3'-portion, wherein the 5'-portion exhibits at least a portion of an anti-sense promoter sequence for a double-stranded RNA polymerase promoter, and the 3'-portion has a 3'-hydroxyl group and exhibits a sequence that is complementary to the DNA sequence tag that it is desired to be joined to the 3'-termini of the first-strand cDNA molecules; and an RNA polymerase that is capable of synthesizing RNA using a DNA template that is joined to a double-stranded RNA polymerase promoter, wherein the 3'-terminus of the template strand exhibits a sequence that is complementary to the anti-sense promoter sequence exhibited by the 5'-portion of the second-strand cDNA synthesis primer;

(B) incubating a solution containing the sample with the one or more RNA molecules of interest, plus at least one of the at least one RNA-dependent DNA polymerases, under conditions and for sufficient time wherein first-strand cDNA molecules that are complementary to the RNA molecules of interest are synthesized;

(C) incubating the solution from step (B) under conditions and for sufficient time wherein RNA that is annealed to DNA and single-stranded RNA are degraded;

(D) incubating the solution from step (C) containing the first-strand cDNA molecules, plus the terminal tagging oligoribonucleotide and at least one of the at least one RNA-dependent DNA polymerases, under conditions and for sufficient time wherein the terminal tagging oligoribonucleotide anneals to the first-strand cDNA molecules and the 3'-termini of the first-strand cDNA molecules are extended using the terminal tagging oligoribonucleotide as a template, wherein first-strand cDNA molecules that have the DNA sequence tag joined to their 3'-termini are synthesized, and then incubating the solution under conditions and for sufficient time wherein RNA that is annealed to DNA and single-stranded RNA are degraded;

(E) incubating the solution from step (D) containing the first-strand cDNA molecules that have the DNA sequence tag joined to their 3'-termini, plus the second-strand cDNA synthesis primer and either at least one of the at least one RNA-dependent DNA polymerases or the DNA-template-specific DNA polymerase, under conditions and for sufficient time wherein double-stranded cDNA molecules that contain a double-stranded RNA polymerase promoter that is recognized by the RNA polymerase are synthesized; and (F) incubating the solution from step (E) containing double-stranded cDNA molecules, plus the RNA polymerase that recognizes and binds the double-stranded RNA polymerase promoter, under conditions and for sufficient time wherein multiple copies of sense RNA molecules are synthesized, each of which exhibits substantially the same sequence as one of the one or more RNA molecules of interest in the sample and has an RNA sequence tag joined to its 5'-terminus.

2. The method of claim 1, wherein, in step (C), said RNA that is annealed to DNA and single-stranded RNA are degraded in the presence of RNase H and a single-strand-specific RNase, after which the RNase H and the single-strand-specific RNase are inactivated.

3. The method of claim 1, wherein, in step (D), said RNA that is annealed to DNA and single-stranded RNA are degraded in the presence of RNase H and a single-strand-specific RNase, after which the RNase H and the single-strand-specific RNase are inactivated.

4. The method of claim 1, wherein said at least one RNA-dependent DNA polymerase provided in step (A) consists of only one RNA-dependent DNA polymerase, which RNA-dependent DNA polymerase is used in step (B) and in step (D).

5. The method of claim 1, wherein said RNA-dependent DNA polymerase is AMV reverse transcriptase or RNase H-minus AMV reverse transcriptase.

6. The method of claim 1, wherein the at least one RNA-dependent DNA polymerase comprises two different RNA-dependent DNA polymerases.

7. The method of claim 1, wherein the RNA-dependent DNA polymerase that is used in step (D) is different from the RNA-dependent DNA polymerase used in step (B).

8. A method comprising:
 (A) providing:
  a sample containing one or more RNA molecules of interest;
  at least one RNA-dependent DNA polymerase;
  a terminal tagging oligoribonucleotide comprising ribonucleotides (rTTO), which terminal tagging oligoribonucleotide comprises a 5'-portion and 3'-portion, wherein the 5'-portion exhibits a sequence that is complementary to the sequence of a DNA sequence tag that it is desired to join to the 3'-termini of first-strand cDNA molecules, and wherein the 3'-portion comprises at least three random nucleotides, of which the 3'-terminal nucleotide is blocked so that it is not capable of being extended by a DNA polymerase;
  a second-strand cDNA synthesis primer, comprising an oligodeoxyribonucleotide that comprises a 5'-portion and a 3'-portion, wherein the 5'-portion exhibits at least a portion of an anti-sense promoter sequence for a double-stranded RNA polymerase promoter, and the 3'-portion has a 3'-hydroxyl group and exhibits a sequence that is complementary to the DNA sequence tag that it is desired to be joined to the 3'-termini of the first-strand cDNA molecules; and
  an RNA polymerase that is capable of synthesizing RNA using a DNA template that is joined to a double-stranded RNA polymerase promoter, wherein the 3'-terminus of the template strand exhibits a sequence that is complementary to the anti-sense promoter sequence exhibited by the 5'-portion of the second-strand cDNA synthesis primer;
 (B) incubating a solution containing the sample with the one or more RNA molecules of interest, plus at least one of the at least one RNA-dependent DNA polymerases, under conditions and for sufficient time wherein first-strand cDNA molecules that are complementary to the RNA molecules of interest are synthesized;
 (C) incubating the solution from step (B) under conditions and for sufficient time wherein RNA that is annealed to DNA and single-stranded RNA are degraded;
 (D) incubating the solution from step (C) containing the first-strand cDNA molecules, plus the terminal tagging oligoribonucleotide and at least one of the at least one RNA-dependent DNA polymerases, under conditions and for sufficient time wherein the terminal tagging oligoribonucleotide anneals to the first-strand cDNA molecules and the 3'-termini of the first-strand cDNA molecules are extended using the terminal tagging oligoribonucleotide as a template, wherein first-strand cDNA molecules that have the DNA sequence tag joined to their 3'-termini are synthesized, and then incubating the solution under conditions and for sufficient time wherein RNA that is annealed to DNA and single-stranded RNA are degraded;
 (E) incubating the solution from step (D) containing the first-strand cDNA molecules that have the DNA sequence tag joined to their 3'-termini, plus the second-strand cDNA synthesis primer and either at least one of the at least one RNA-dependent DNA polymerases or the DNA-template-specific DNA polymerase, under conditions and for sufficient time wherein double-stranded cDNA molecules that contain a double-stranded RNA polymerase promoter that is recognized by the RNA polymerase are synthesized;
 (F) incubating the solution from step (E) containing double-stranded cDNA molecules, plus the RNA polymerase that recognizes and binds the double-stranded RNA polymerase promoter, under conditions and for sufficient time wherein multiple copies of sense RNA molecules are synthesized, each of which exhibits substantially the same sequence as one of the one or more RNA molecules of interest in the sample and has an RNA sequence tag joined to its 5'-terminus;
 (G) further providing:
  the sense RNA molecules that have the RNA sequence tag joined to their 5'-termini from step (F);
  a second-round first-strand cDNA synthesis primer comprising one or more oligonucleotides, at least one of which is complementary to each of the sense RNA molecules that have the RNA sequence tag joined to their 5'-termini that are provided in step (G);
  at least one RNA-dependent DNA polymerase;
  a second-round second-strand cDNA synthesis primer, comprising an oligodeoxyribonucleotide that has a 5'-portion and a 3'-portion, wherein the 5'-portion exhibits at least a portion of an anti-sense promoter sequence for a double-stranded RNA polymerase promoter, and the 3'-portion has a 3'-hydroxyl group and exhibits a sequence that is complementary to the DNA sequence tag that is joined to the 3'-termini of the first-strand cDNA molecules from step (D);
  an RNA polymerase that is capable of synthesizing RNA using a DNA template that is joined to a double-stranded RNA polymerase promoter that exhibits, on the 3'-terminus of the template strand, the sense promoter sequence of the double-stranded RNA polymerase promoter that, at least a portion of which, is complementary to the anti-sense promoter sequence exhibited by the 5'-portion of the second-round second-strand cDNA synthesis primer;
 (H) incubating a solution containing the sense RNA molecules that have the RNA sequence tag joined to their 5'-termini, plus the second-round first-strand cDNA synthesis primers and at least one of the at least one RNA-dependent DNA polymerases, under conditions and for sufficient time wherein the second-round first-strand cDNA synthesis primers anneal to the sense RNA molecules that have the RNA sequence tag joined to their 5'-termini and second-round first-strand cDNA molecules that have the DNA sequence tag joined to their 3'-termini are synthesized;

(I) incubating the solution from step (H) under conditions and for sufficient time wherein RNA that is annealed to DNA is degraded;

(J) incubating a solution containing the second-round first-strand cDNA molecules that have the DNA sequence tag joined to their 3'-termini, plus the second-round second-strand cDNA synthesis primer and either at least one of the at least one the RNA-dependent DNA polymerases or the DNA-template-specific DNA polymerase, under conditions and for sufficient time wherein second-round double-stranded cDNA molecules that contain a double-stranded RNA polymerase promoter are synthesized; and (K) incubating the solution from step (J), containing second-round double-stranded cDNA molecules, plus the second-round RNA polymerase, under conditions and for sufficient time wherein multiple copies of sense RNA molecules are synthesized, each of which, exhibits substantially the same sequence as one of the one or more RNA molecules of interest in the sample and has the RNA sequence tag joined to its 5'-terminus.

9. The method of claim 8, wherein the at least one RNA-dependent DNA polymerase used in step (H), is the same as at least one RNA-dependent DNA polymerase that is used in step (B) or in step (D).

10. The method of claim 8, wherein the at least one RNA-dependent DNA polymerase used in step (H) is AMV reverse transcriptase or RNase H-minus AMV reverse transcriptase.

11. The method of claim 8, wherein the DNA-template-specific DNA polymerase used in step (J) is a thermostable DNA polymerase.

12. The method of claim 8, wherein substantially no RNA molecules are synthesized in the absence of the sample containing the one or more RNA molecules of interest.

13. The method of claim 8, wherein an oligodeoxyribonucleotide is provided in step (A), and is included in the solution as a first-strand cDNA synthesis primer in step (B) and/or step (H).

14. The method of claim 8, wherein the 5'-portion of the terminal tagging oligoribonucleotide does not exhibit a sense promoter sequence or an anti-sense promoter sequence for an RNA polymerase promoter.

* * * * *